(12) United States Patent
Shi et al.

(10) Patent No.: US 12,156,889 B2
(45) Date of Patent: Dec. 3, 2024

(54) METHODS OF ADMINISTERING MESENCHYMAL STEM CELLS ACTIVATED BY CYTOKINES FOR ENHANCING IMMUNOSUPPRESSION

(71) Applicant: Rutgers, The State University of New Jersey, New Brunswick, NJ (US)

(72) Inventors: Yufang Shi, Belle Mead, NJ (US); Guangwen Ren, Bar Harbor, ME (US); Liying Zhang, Belle Mead, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 325 days.

(21) Appl. No.: 17/150,457

(22) Filed: Jan. 15, 2021

(65) Prior Publication Data
US 2021/0213067 A1   Jul. 15, 2021

Related U.S. Application Data

(62) Division of application No. 16/100,545, filed on Aug. 10, 2018, now Pat. No. 10,898,523, which is a division of application No. 14/652,324, filed as application No. PCT/US2013/075208 on Dec. 14, 2013, now Pat. No. 10,046,011.

(60) Provisional application No. 61/737,616, filed on Dec. 14, 2012.

(51) Int. Cl.

| A61K 35/28 | (2015.01) |
| A61K 38/18 | (2006.01) |
| A61K 38/19 | (2006.01) |
| A61K 38/20 | (2006.01) |
| A61K 38/21 | (2006.01) |
| A61P 37/04 | (2006.01) |
| A61P 37/06 | (2006.01) |
| C12N 5/00 | (2006.01) |
| C12N 5/074 | (2010.01) |
| C12N 5/0775 | (2010.01) |
| A61K 35/12 | (2015.01) |
| A61K 45/06 | (2006.01) |
| A61P 37/02 | (2006.01) |
| C07K 14/495 | (2006.01) |
| C07K 14/50 | (2006.01) |
| C07K 14/52 | (2006.01) |
| C07K 14/525 | (2006.01) |
| C07K 14/545 | (2006.01) |
| C07K 14/56 | (2006.01) |
| C07K 14/565 | (2006.01) |
| C07K 14/57 | (2006.01) |

(52) U.S. Cl.
CPC .......... *A61K 35/28* (2013.01); *A61K 38/1825* (2013.01); *A61K 38/1841* (2013.01); *A61K 38/191* (2013.01); *A61K 38/20* (2013.01); *A61K 38/2006* (2013.01); *A61K 38/212* (2013.01); *A61K 38/215* (2013.01); *A61K 38/217* (2013.01); *A61P 37/04* (2018.01); *A61P 37/06* (2018.01); *C12N 5/0018* (2013.01); *C12N 5/0607* (2013.01); *C12N 5/0662* (2013.01); *C12N 5/0663* (2013.01); *C12N 5/0665* (2013.01); *A61K 2035/122* (2013.01); *A61K 45/06* (2013.01); *A61P 37/02* (2018.01); *C07K 14/495* (2013.01); *C07K 14/50* (2013.01); *C07K 14/52* (2013.01); *C07K 14/525* (2013.01); *C07K 14/545* (2013.01); *C07K 14/56* (2013.01); *C07K 14/565* (2013.01); *C07K 14/57* (2013.01); *C12N 2500/05* (2013.01); *C12N 2501/10* (2013.01); *C12N 2501/115* (2013.01); *C12N 2501/15* (2013.01); *C12N 2501/2301* (2013.01); *C12N 2501/2317* (2013.01); *C12N 2501/24* (2013.01); *C12N 2501/25* (2013.01); *C12N 2502/1114* (2013.01)

(58) Field of Classification Search
CPC .... A61K 35/23; A61K 38/191; A61K 38/217; A61K 38/20; A61K 38/2006; A61K 35/28; C07K 14/52; C07K 14/525; C07K 14/545; C07K 14/57; C07K 14/54; C12N 5/0662; C12N 5/0063; C12N 5/0663; C12N 2501/04; C12N 2501/2301; C12N 2501/2317; C12N 2501/25; C12N 5/0665; A61P 37/06

See application file for complete search history.

(56) References Cited

U.S. PATENT DOCUMENTS

| 5,741,815 A | 4/1998 | Lai |
| 5,847,004 A | 12/1998 | Lai |
| 5,849,282 A | 12/1998 | Kawai et al. |
| 5,942,225 A | 8/1999 | Bruder et al. |
| 9,301,979 B2 | 4/2016 | Shi et al. |

(Continued)

OTHER PUBLICATIONS

Sivanathan et al., Abstract 108 on p. 52 of Nephrology, vol. 16, Issue S1, Sep. 2011.*

(Continued)

*Primary Examiner* — Zachary C Howard
(74) *Attorney, Agent, or Firm* — FOX ROTHSCHILD LLP

(57) ABSTRACT

The present invention provides methods or kits with inflammatory cytokines to pretreat 1-ISCs to augment their immune modulatory effect, in prevention and treatment of various diseases such as multiple sclerosis, arthritis, lupus, sepsis, hepatitis, cirrhosis, Parkinson's disease, chronic infections, and GvHD. The present invention relates to novel methods for enhancing the immunosuppressive or the immune stimulatory activities of mesenchymal stem cells (JvfSCs).

8 Claims, 22 Drawing Sheets

Specification includes a Sequence Listing.

(56) References Cited

U.S. PATENT DOCUMENTS

| | | |
|---|---|---|
| 2005/0233443 A1 | 10/2005 | Freyman |
| 2007/0128722 A1 | 6/2007 | Lin et al. |
| 2007/0160583 A1 | 7/2007 | Lange et al. |
| 2009/0202479 A1 | 8/2009 | Shi et al. |

OTHER PUBLICATIONS

Ren et al., "Concise Review Mesenchymal Stem Cells and Translational Medicine: Emerging Issues." Stem Cells Trans. Med., Dec. 7, 2011, pp. 51-58.
Ren et al., "Adhesion molecules. Key players in Mesenchymal stem cell-mediated immunosupresion." Cell Adhesion & Migration 5:1, Jan./Feb. 2011, pp. 20-22.
Cheng et al., 1994. Endocrinology. 134(1): pp. 277-286.
Dulbecco's Modified Eagle's Medium Product No. D5523 (Product Data Sheet), Sigma-Aldrich, 1 page, Apr. 2007.
Ren et al: "Mesenchymal stem cell-mediated immunosuppression occurs via concerted action of chemokines and nitric oxide", 2008, Cell Stem Cell. 2, pp. 141-150.
Keating et al., 2008, Cell Stem Cell. 2, pp. 106-107.
Rifas, Leonard: "T-cell cytokine induction of BMP-2 regulates human mesenchymal stromal cell differentiation and mineralization", 2006. Journal of Cellular Biochemistry, vol. 98, pp. 706-714.
Aggarwal et al., "Human mesenchymal stem cells modulate allogeneic immune cell responses", Blood 2005, 105 (4), pp. 1815-1822.
Dazzi et al., "The role of mesenchymal stem cells in haemopoiesis", Blood Reviews, 2006, 20, pp. 161-171.
Denham et al., "Inhibition of the reactive proliferation of lymphocytes by activated macrophages: the role of nitric oxide", Clin. Exp. Immunol., 1992, 87, 1 pp. 157-162.
Djouad et al., "Reversal of the immunosuppressive properties of mesenchymal stem cells by tumor necrosis factor alpha in collagen-induced arthritis", Arthritis & Rheumatism 2005, 52(5) pp. 1595-1603.
Halleux, et al: "Multi-Lineage Potential of Human Mesenchymal Stem Cells Following Clonal Expansion", J Musculoskel Neuron Interact, 2001, vol. 2, No. 1, pp. 71-76.
Hattori et al., "Differential effects of anti-fas ligand and anti-tumor necrosis factor alpha antibodies on acute graft-versus-host disease pathologies", Blood, 1998, 91 (11), pp. 4051-4055.
Inoue et al., "Immunomodulatory effects of mesenchymal stem cells in a rat organ transplant model", Transplantation 2006, 81 (11), pp. 1589-1595.
Isobe et al., "Nitric oxide production from a macrophage cell line:interaction with autologous and allogeneic lymphocytes", Journal of Cellular Biochemistry, 1993, 53, pp. 198-205.
Keating, Armand, "Mesenchymal stromal cells", Current Opinion in Hematology 2006, 3, pp. 419-425.
Koc et al., "Mesenchymal stem cells-Allogeneic mesenchymal stem cell infusion for treatment of metachromatic eukodystrophy (MLD) and Hurler syndrome (MPS-IH)", Bone Marrow Transplantation, 2002, 30, pp. 215-222.
Krampera et al., "Role for interferon-y in the immunomodulatory activity of human bone marrow mesenchymal stem cells", Stem Cells, 2006, 24, pp. 386-398.
Le Blanc et al., "Treatment of severe acute graft-versus-host disease with third party haploidentical mesenchymal stem cells", The Lancet, 2004, 363, pp. 1439-1441.
Le Blanc et al., "Mesenchymal stem cells:properties and role in clinical bone marrow transplantation", Current Opinion in Immunology, 2006, 18, pp. 586-591.
Meisel et al., "Human bone marrow stromal cells inhibit allogeneic T-cell responses by indoleamine 2,3-dioxygenase mediated tryptophan degradation", Blood, 2004, 103 (12), pp. 4619-4621.
McCarthy, Jr., et al., "Inhibition of interleukin-1 by an interleukin-1 receptor antagonist prevents graft-versus-host disease", Blood, 1991, 78 (8), pp. 1915-1918.
Miszta-Lane et al., Stem cell sources for clinical islet transplantation in type 1 diabetes:embryonic and adult stem cells, Medical Hypotheses, 2006, 67, pp. 909-913.
Plumas et al., "Mesenchymal stem cells induce apoptosis of activated T cells", Leukemia 2005, 19, pp. 1597-1604.
Rasmusson et al. 1 "Mesenchymal stem cells inhibit lymphocyte proliferation by mitogens and alloantigens by different mechanisms" I Experimental Cell Research , 2005, 305, pp. 33-41.
Sato et al., "Nitric oxide plays a critical role in suppression of T-cell proliferation by mesenchymal stem cells", Blood, 2007, 109(1), pp. 228-234.
Schenk et al., "Monocyte chemotactic protein-3 is a myocardial mesenchymal stem cell homing factor", Stem Cells, 2007, 25, pp. 245-251.
Zappla et al., "Mesenchymal stem cells ameliorate experimental autoimmune encephalomyelitis inducing T-cell anergy", Blood, 2005 , 106 (5), pp. 1755-1761.
Uccelli et al., "Immunoregulatory function of mesenchymal stem cells", Eur. J. Immunol., 2006, 36, pp. 2566-2573.
Van Laar et al., "Adult stem cells in the treatment of autoimmune diseases", Rheumatology, 2006, 45, pp. 1187-1193.
Xu et al., "Immunosuppressive properties of cloned bone marrow mesenchymal stem cells", Cell Research, 2007, 17, pp. 240-248.
David D. Chaplin, MD: "Overview of the human immune response", J Allergy Clin Immunol, 2006, vol. 117, No. 2, pp. s430-s435.
English, et al: "IFN-y and TNF-a differentially regulate immunomodulation by murine mesenchymal stem cells", Immunology Letters, 2007, vol. 110, pp. 91-100.

\* cited by examiner

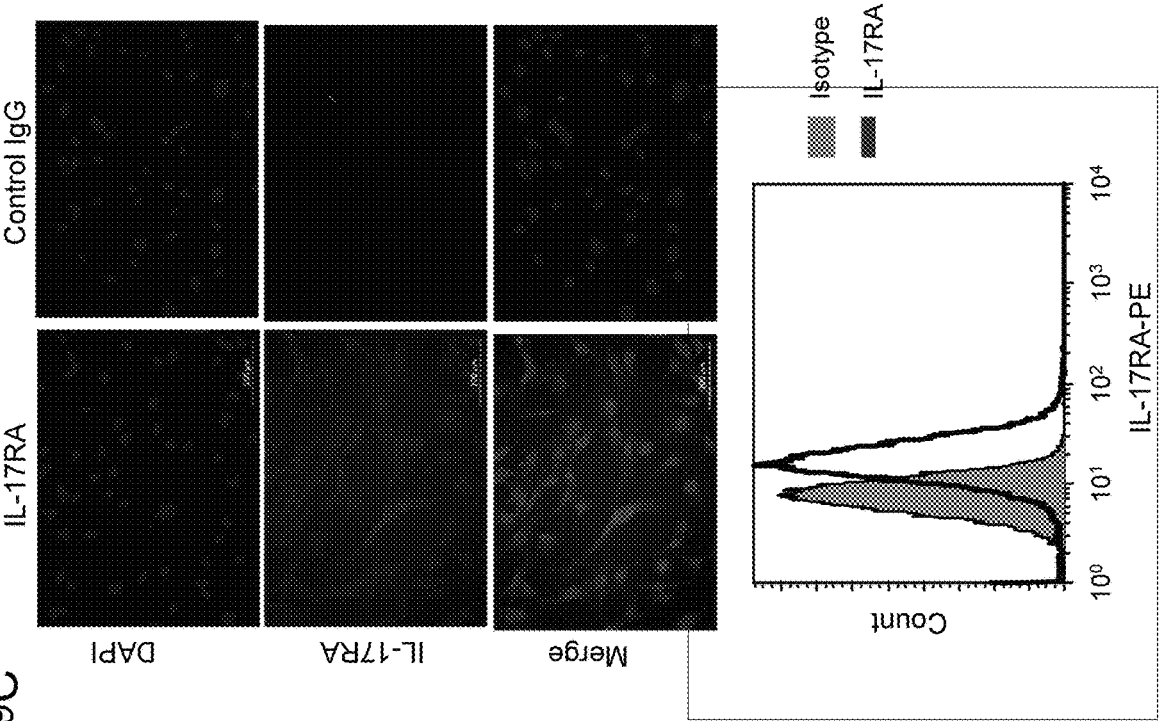
FIG. 9C
FIG. 9
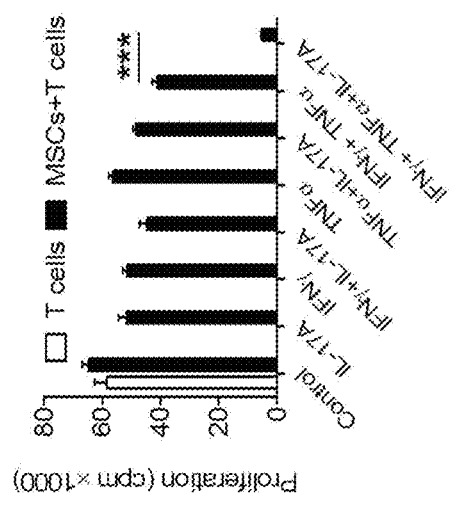
FIG. 9A
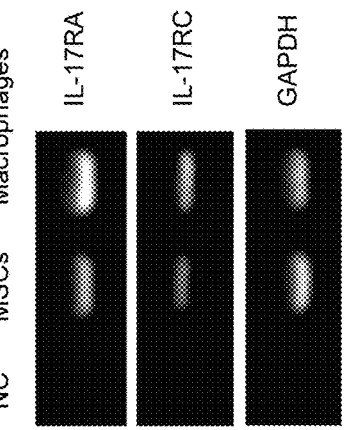
FIG. 9B

FIG. 9 (cont...)

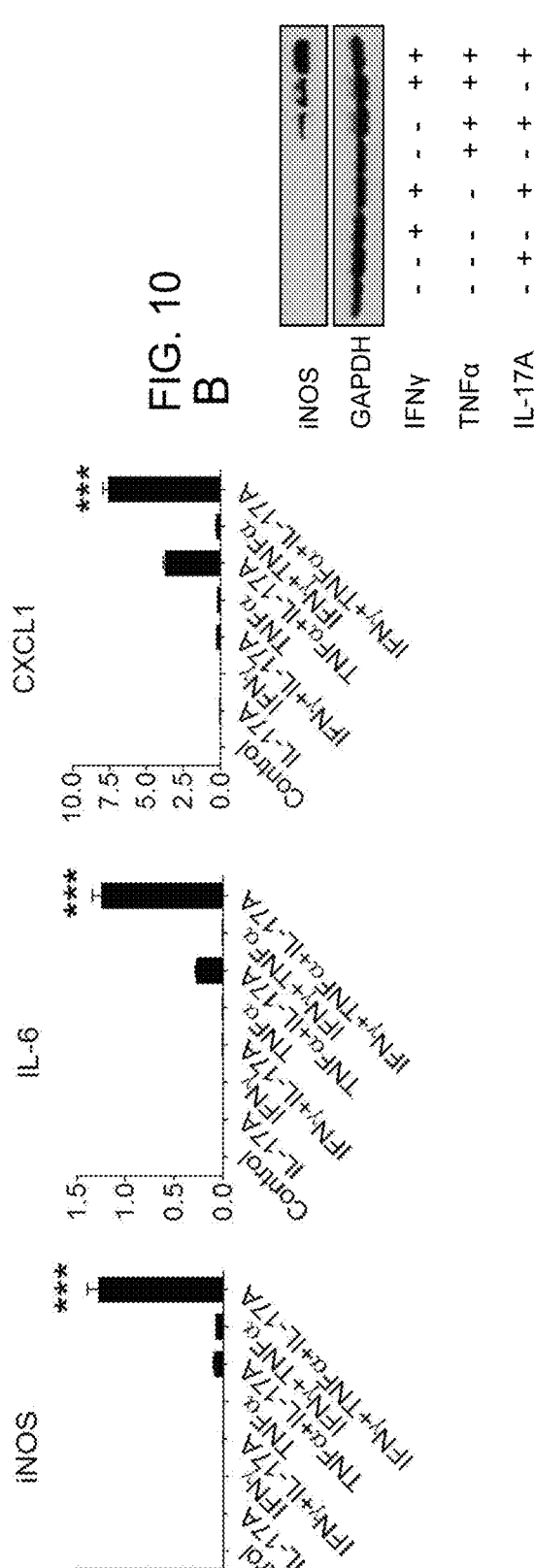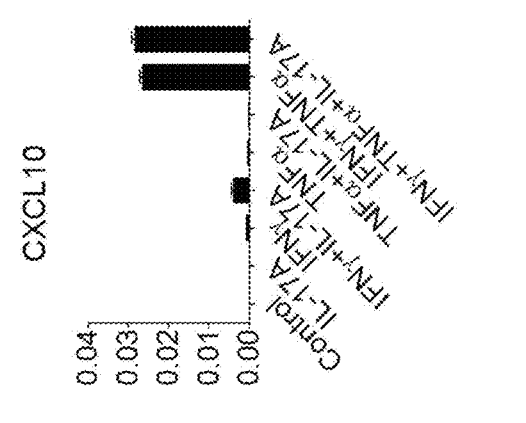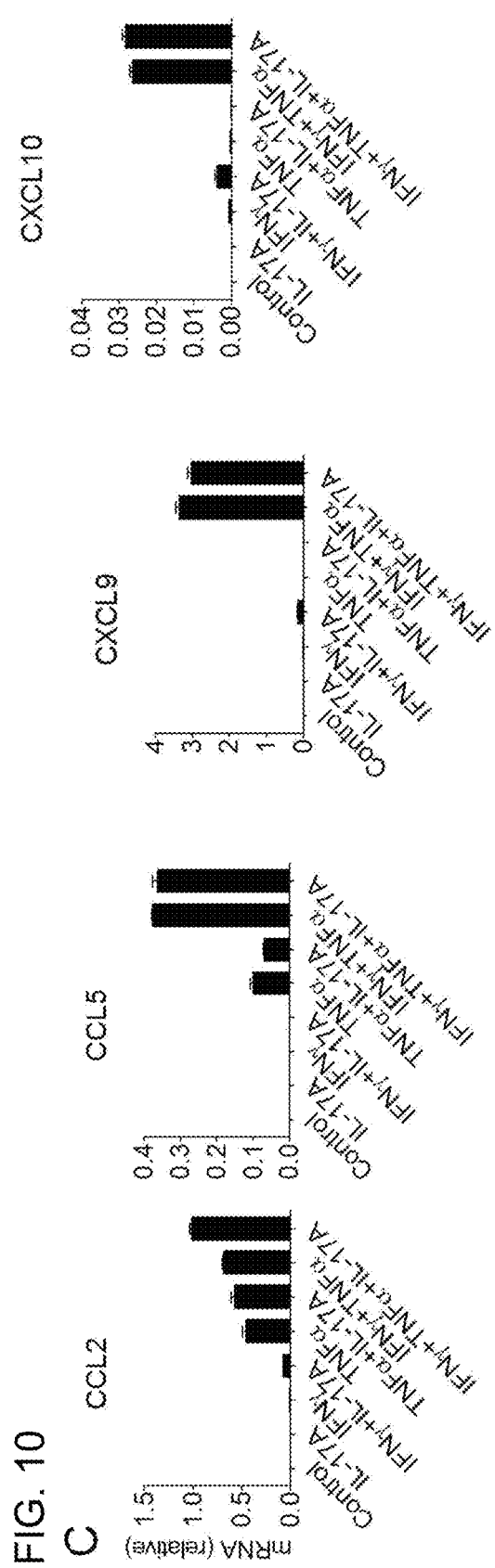
FIG. 10A
FIG. 10B
FIG. 10C

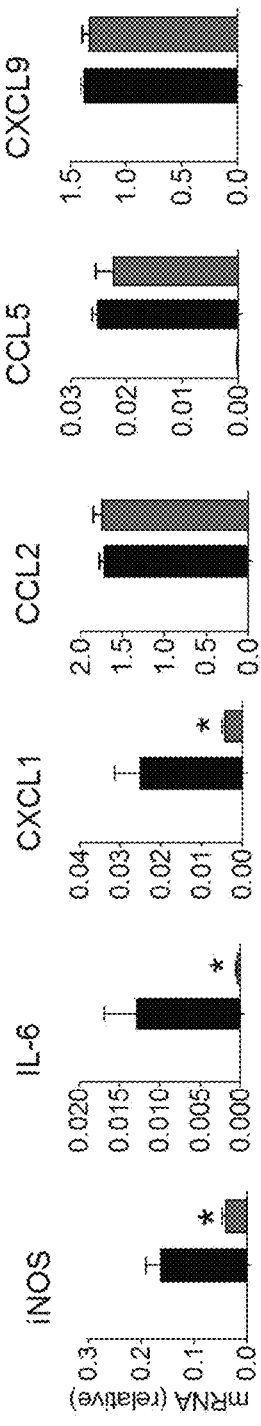
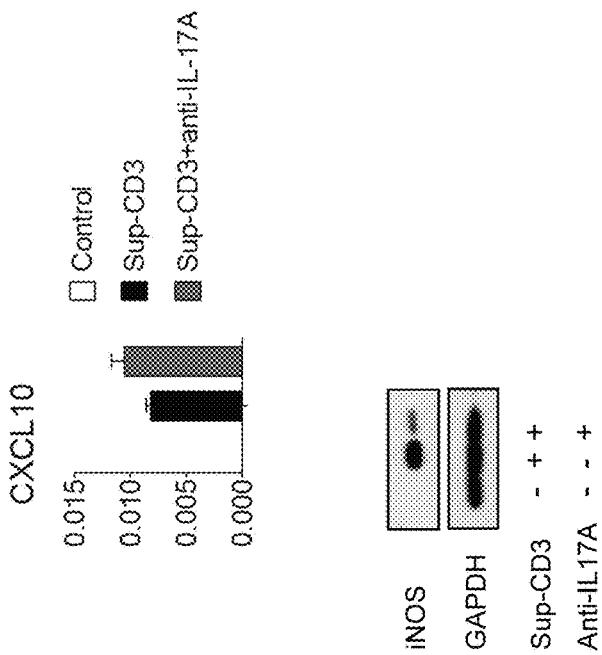
FIG. 10 (cont...)

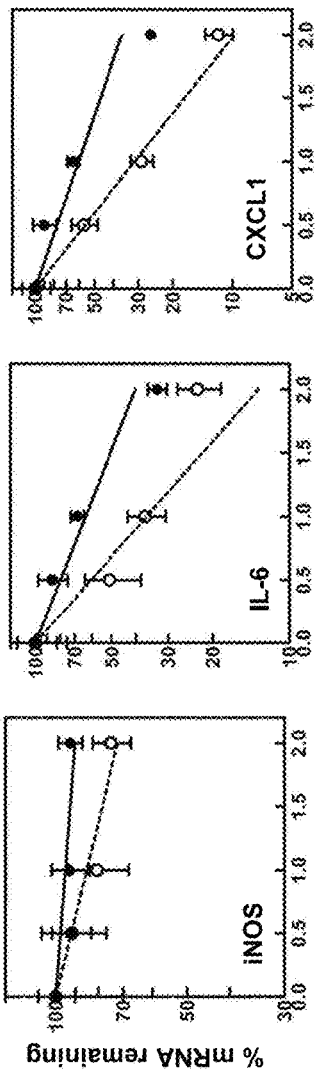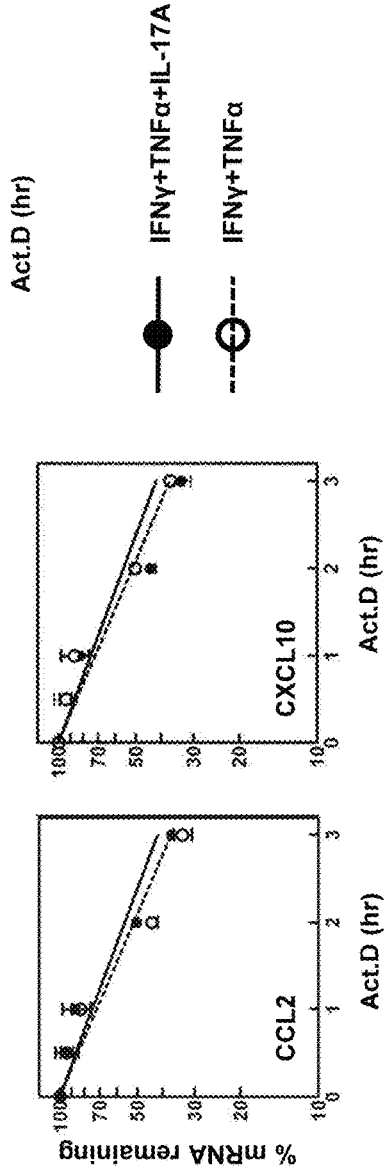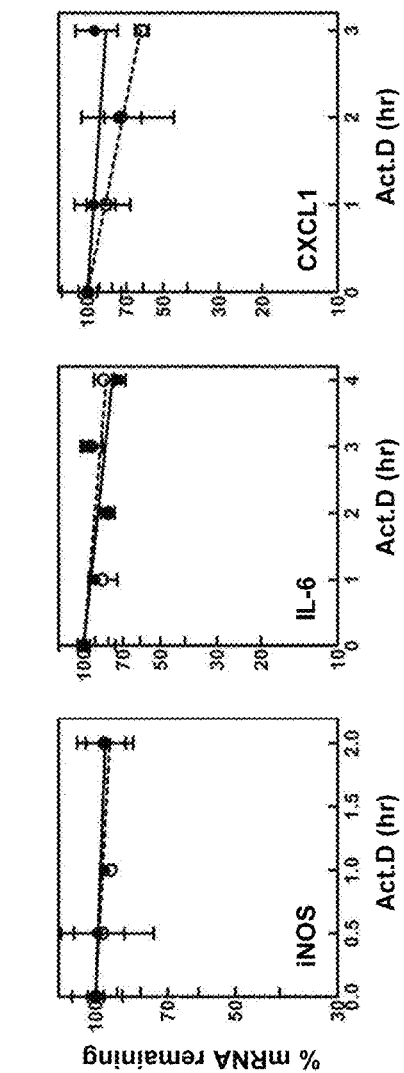
FIG. 13A
FIG. 13B

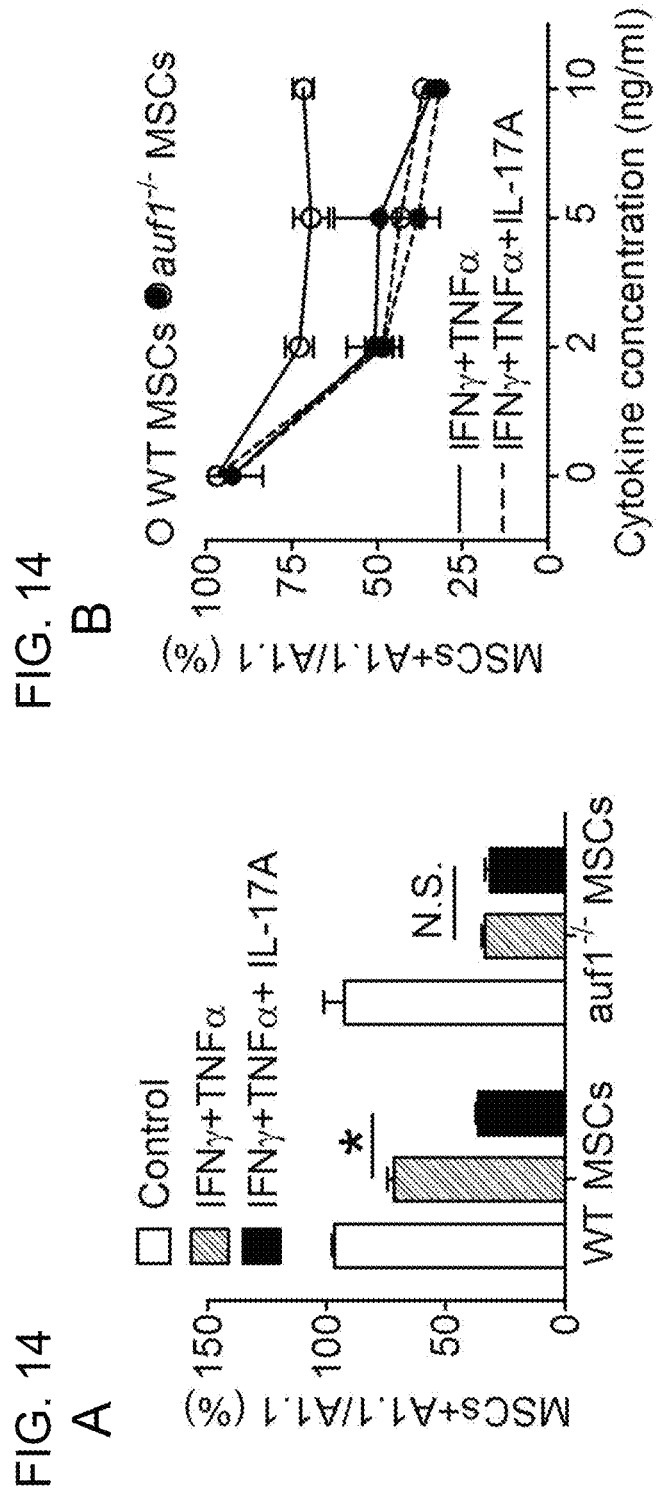

FIG. 15 (cont...)

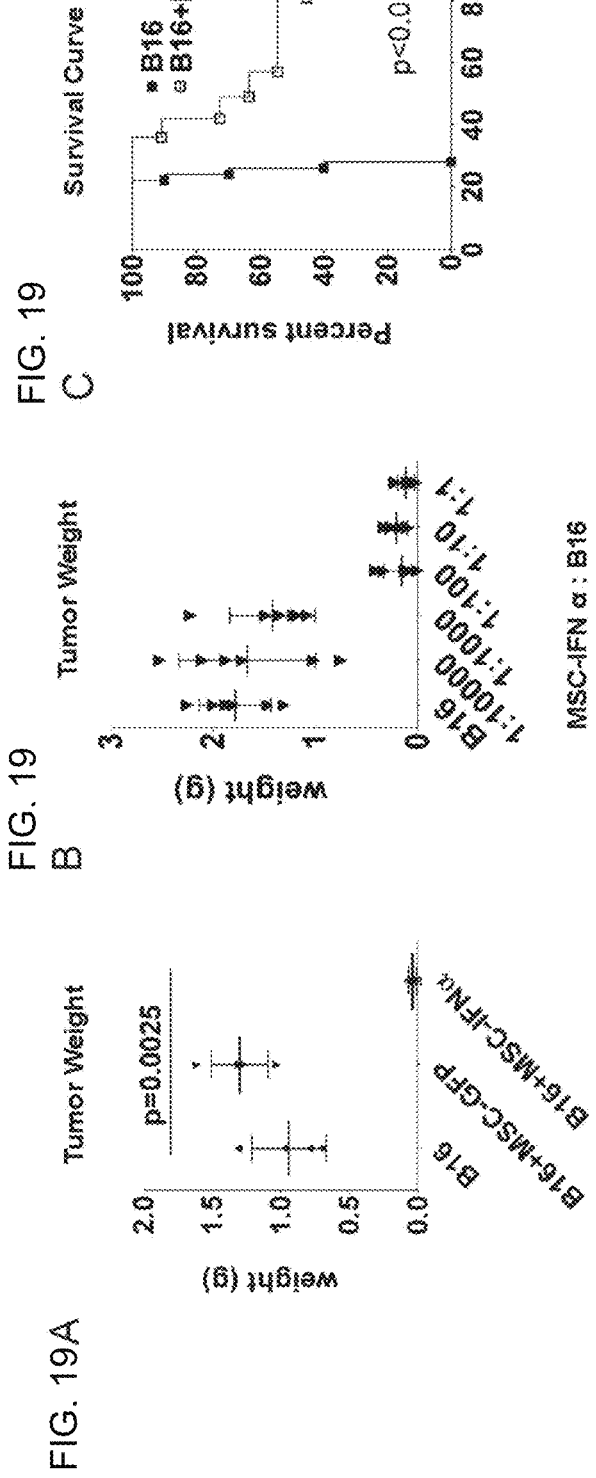
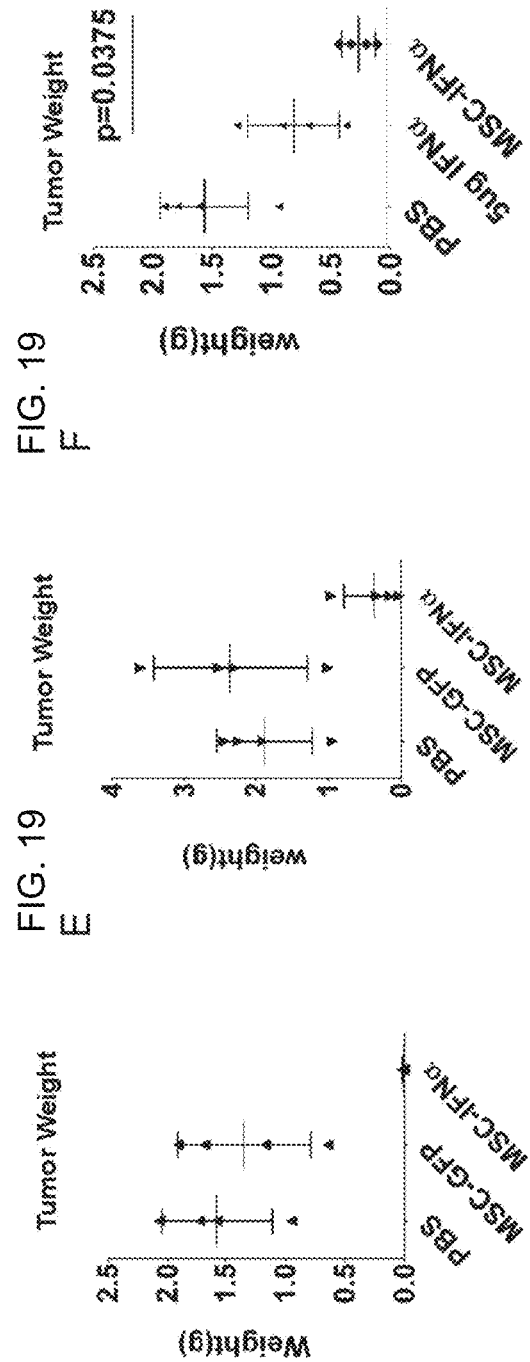
FIG. 19A, FIG. 19B, FIG. 19C, FIG. 19D, FIG. 19E, FIG. 19F ically migrate into tumors, and have been suggested as a tumor-specific vector to deliver anti-tumor agents. In fact, MSCs have been genetically engineered to express various anti-tumor factors, including type I interferon, TRAIL, IL-12, and LIGHT, and have been shown to possess potent anti-tumor effect in animal models. Thus, enhancing anti-tumor immune responses by using the MSC guided stimulatory effects holds great promise for further cancer therapy.
METHODS OF ADMINISTERING MESENCHYMAL STEM CELLS ACTIVATED BY CYTOKINES FOR ENHANCING IMMUNOSUPPRESSION

CROSS-REFERENCE TO RELATED APPLICATION

The present application is a divisional of U.S. patent application Ser. No. 16/100,545, filed Aug. 10, 2018, which is a divisional of U.S. patent application Ser. No. 14/652,324 filed Jun. 15, 2015, now U.S. Pat. No. 10,046,011 issued Aug. 14, 2018, which is the U.S. National Phase of International Patent Application Serial No. PCT/US13/75208, filed Dec. 14, 2013, which claims the benefit of priority under 35 U.S.C. § 119(e) of U.S. Provisional Application Ser. No. 61/737,616, filed Dec. 14, 2012. International Patent Application Serial No. PCT/US13/75208 is also a continuation-in-part of U.S. application Ser. No. 12/362, 847, filed Jan. 30, 2009, now U.S. Pat. No. 8,685,728 issued Apr. 1, 2014, which claims the benefit of priority under 35 U.S.C. § 119(e) of U.S. Provisional Application Ser. No. 61/063,288, filed Jan. 31, 2008. The entire disclosures of the applications noted above are incorporated herein by reference.

GOVERNMENT INTERESTS

This invention was made with government support under grant number GM866889, DE014913, and DE019932 from the National Institutes of Health, and stem cell grants from New Jersey Commission on Science and Technology (NJCST-2042-014-84)

CROSS-REFERENCE TO A SEQUENCE LISTING

This application includes a "Sequence Listing" which is provided as an electronic document having the file name "096738.00685_ST25.txt" (3416 bytes, created Jan. 14, 2021), which is herein incorporated by reference in its entirety.

FIELD OF THE INVENTION

The present invention relates to novel methods for enhancing the immunosuppressive or the immune stimulatory activities of mesenchymal stem cells (MSCs).

BACKGROUND OF THE INVENTION

Cellular therapy involves administration of living cells for any purpose including diagnostic or preventive purposes and of any condition, for example regenerative medicine, transplantation and even cancer. Stem cells are believed to have tremendous potential in cell therapy. However, its effective use in a clinical setting has been elusive for variety of reasons.

Stem cells have two distinct characteristics that distinguish them from other cell types. First, they are unspecialized and can self-renew for long periods without significant changes in their general properties. Second, under certain physiologic or experimental conditions, stem cells can be induced to differentiate into various specialized cell types. Thus, stem cells hold a great promise for regenerative medicine. There are two major types of stem cells: embryonic stem (ES) cells and adult stem cells.

Adult stem cells exist in many mature tissues, such as bone marrow, muscle, fat and brain. While most studies of adult stem cells have focused on CD34+ hematopoietic stem cells, the distinct lineage of CD34− fibroblast-like mesenchymal stem cells (MSCs), especially those derived from bone marrow, have attracted significant attention from basic and clinical investigators (Chen, et al. (2006) Immunol. Cell Biol. 84:413-421; Keating (2006) Curr. Opin. Hematol. 13:419-425; Pommey & Galipeau (2006) Bull. Cancer 93:901-907). Bone marrow-derived MSCs have been shown to differentiate into several different cell types of tissue, such as cartilage, bone, muscle, and adipose tissue (Barry & Murphy (2004) Int. J. Biochem. Cell Biol. 36:568-584; Le Blanc & Ringden (2006) Lancet 363:1439-1441).

Mesenchymal stem cells have great potential for regenerative medicine and autoimmune disorders, and have been evaluated in clinical trials to treat many different kinds of diseases, including liver fibrosis, diabetes, GvHD, and Crohn's disease. MSCs can help successful engraftment of transplanted bone marrow and cells differentiated from embryonic stem cells or induced pluripotent stem (iPS) cells. Accordingly, the immune suppressive behavior of MSCs can provide a beneficial method in combating such conditions.

From another angle, the immune system plays a key role in combating tumor development and progression. Tumors are always accompanied by an immunosuppressive microenvironment. MSCs have an intrinsic ability to specifically migrate into tumors, and have been suggested as a tumor-specific vector to deliver anti-tumor agents. In fact, MSCs have been genetically engineered to express various anti-tumor factors, including type I interferon, TRAIL, IL-12, and LIGHT, and have been shown to possess potent anti-tumor effect in animal models. Thus, enhancing anti-tumor immune responses by using the MSC guided stimulatory effects holds great promise for further cancer therapy.

The underlying in vivo mechanisms through which MSCs modulates immune response, suppression or inducement are largely unknown. More importantly, the clinical effects of MSCs vary significantly depending on the physiological and pathological status of the host and the microenvironment experienced by MSCs themselves. Thus, there exists a need to further understand and develop regimens to successfully employ the immune modulatory effects of MSCs in clinical settings.

SUMMARY OF THE INVENTION

The present invention describes methods for suppressing and inducing immune response by trained populations of MSC. The present invention also provides a new source of immune adjuvants using gene modified MSCs.

For use therapeutically, the pharmaceutical composition of the invention can be provided as a kit. A kit of the invention contains a pharmaceutically acceptable carrier; an isolated population of mesenchymal stem cells; isolated IFN gamma (IFNγ); isolated IL-1 alpha (IL-1 α); Type 1 interferons (IFN-I such as IFN-α (alpha), IFN-β (beta)), Transforming growth factor beta (TGF β), Fibroblast growth factor (FGF), isolated interleukin-17 A (IL17-A) and Tumor necrosis factor (TNF). In another aspect, the kit can contain instructions for using the kit in a method for attenuating an immune response and/or inducing or boosting an immune response. In yet another embodiment, the kit contains a pharmaceutically acceptable carrier, inhibitors of immunosuppressive molecules (such as NO synthases (iNOS)/indoleamine-2,3-dioxygenase (IDO) inhibitors), other cytokines or therapeutic formulations for boosting or suppressing an immune response.

In one aspect of the invention, composition containing isolated purified MSCs, IFNγ and IL-17A are described in admixture with a pharmaceutically acceptable carrier. The present invention also provides a composition comprising isolated MSCs, IFNγ, TNF α, IL-1 and IL-17 in admixture with a pharmaceutically acceptable carrier.

In another aspect of the present invention, methods for modulating an immune response are described by administering an effective amount of a composition containing isolated MSCs that have been treated with IFNγ and any one of the cytokines IL-1 α; an IFN-I, TGF β, FGF, TNF α or IL-17 and any combinations thereof to a subject in need of a treatment for suppressing or inducing the subject's immune response. In another embodiment, methods of enhancing immunosuppression in a subject by administering an effective amount of a composition containing isolated MSC that have been treated with IFNγ and any one of the cytokines IL-1 α, B; TNF α or IL-17 as compared to a subject that has not received such treatment or receives anti-inflammatory drugs including corticosteroids or non-steroidal anti inflammatory drugs to suppress immunity.

The preferred methods and materials are described below in examples which are meant to illustrate, not limit, the invention. Skilled artisans will recognize methods and materials that are similar or equivalent to those described herein, and that can be used in the practice or testing of the present invention. Other features and advantages of the invention will be apparent from the detailed description, and from the claims.

BRIEF DESCRIPTION OF THE FIGURES

(FIG. 8B) iNOS expression enhancing effect of IL-17A at different times after IFNγ and TNFα treatment.

FIGS. 9A, 9B, 9C, 9D, 9E, 9F and 9G. (FIG. 9A). Cloned MSCs were first treated with the indicated combinations of recombinant cytokines IFNγ, TNFα, IL-17A (2 ng/ml each) for 12 hr, then cocultured with CD4$^+$ T cell blasts at a 1:20 ratio (MSC:T cells), and proliferation was assessed by 3H-thymidine incorporation after an additional 12 hr. (FIG. 9B). The mRNA expression of IL-17 receptor family members in MSCs or Raw 264.7 (Macrophages) were examined by RT-PCR. NC: No RT. (FIG. 9C). Surface expression of IL-17RA was detected by immunofluoresence or flow cytometry in cloned MSCs. (FIGS. 9D and 9E). MSCs were first treated with IFNγ and TNFα with or without IL-17A (10 ng/ml), IFNγ and TNFα were supplemented at different cytokine concentrations, for 12 hr, and then cocultured with CD4$^+$ T cell blasts (FIG. 9D) or T cell hybridoma A1.1 cells (FIG. 9E) at a ratio of 1:20 for 12 hr. T cell proliferation was measured by 3H-Tdr incorporation. (FIG. 9F). MSCs were first treated with IFNγ and TNFα (2 ng/ml) with graded concentrations of IL-17A, for 12 hr, and then cocultured with T cell hybridoma A1.1 cells at a ratio of 1:10 for 12 hr. T cell proliferation was measured by 3H-thymidine incorporation. (FIG. 9G). MSCs were cocultured with fresh C57BL/6 splenocytes plus anti-CD3, anti-CD28, and antibodies against IL-17A, at a 1:20 or 1:40 ratio (MSCs:splenocytes), for 48 hr, and then cell proliferation was assessed by 3H-thymidine incorporation. Proliferation values represent means±SEM of three wells from a representative of three experiments.

FIGS. 10A, 10B, 10C, 10D and 10E. (FIGS. 10A and 10C). MSCs were cultured with different combinations of inflammatory cytokines IFNγ, TNFα, IL-17A (10 ng/ml) for 12 hr, and then cells were harvested for RNA extraction. The mRNA expression levels of inflammatory molecules iNOS, IL-6, CXCL1 (FIG. 10A) and chemokines CCL2, CCL5, CXCL9, CXCL10 (FIG. 10C) were detected by quantitative RT-PCR. (FIG. 10B). MSCs were cultured with different combinations of inflammatory cytokines IFNγ, TNFα, IL-17A (10 ng/ml) for 24 hr, and the protein level of iNOS was detected by Western Blot. (FIG. 10D). MSCs were supplemented with Sup-CD3 or Sup-CD3 pretreated with antibodies against IL-17A, and cells were collected for RNA extraction after 12 hr. The expression of iNOS, IL-6, CXCL1, CCL2, CCL5, CXCL9 and CXCL10 were measured by quantitative RT-PCR. Sup-CD3: supernatant from splenocytes activated by anti-CD3 and anti-CD28. (FIG. 10E). MSCs were treated with Sup-CD3 or Sup-CD3 pretreated with antibodies against IL-17A, and the protein level of iNOS was assessed by Western Blot after 24 hr. mRNA expression values are means±SEM of three wells from a representative of three independent experiments. Western Blot data is from a representative of three independent experiments.

(FIG. 11A) MSCs with Act1 knockdown or control were treated with IL-17A for different time and the phosphorylation levels of IκBα, ERK, p65, JNK were assessed by Western Blot. (FIG. 11B) MSCs with Act1 knockdown or control were treated with IFNγ and TNFα with or without IL-17A (all cytokines supplemented at 5 ng/ml) the protein levels of iNOS and Act1 were assessed by Western Blot. (FIG. 11C) MSCs (Act1 knockdown or control) were treated with different cytokines 12 hr, and iNOS expression was measured by quantitative RT-PCR. mRNA expression values are means±SEM. (FIG. 11D) MSCs (Act1 knockdown or control) were first treated with IFNγ and TNFα with or without IL-17A (all cytokines supplemented at 5 ng/ml) for 12 hr, and then cocultured with T cell hybridoma A1.1 cells at a ratio of 1:10 for 12 hr. T cell proliferation was measured by 3H-Tdr incorporation, taking the proliferation level of A1.1 alone as 100%.

(FIG. 12A). WT MSCs or auf1$^{-/-}$ MSCs were treated with IFNγ and TNFα, or together with IL-17A (all cytokines supplemented at 10 ng/ml) for 12 hr, and iNOS, IL-6 and CXCL1 expression was measured by quantitative RT-PCR. mRNA expression values are means±SEM of three wells from a representative of three independent experiments. (FIG. 12B). WT MSCs were treated with IFNγ and TNFα (10 ng/ml), or together with different concentrations of IL-17A; auf1$^{-/-}$-MSCs were treated with IFNγ and TNFα (10 ng/ml), or together with 10 ng/ml of IL-17A. After 24 hr, cells were harvested for detection of iNOS by Western Blot. Western blot is a representative of three independent experiments.

FIGS. 13A and 13B. Wild-type (FIG. 13A) or auf14-MSCs (FIG. 13B) were treated with IFNγ and TNFα, with or without IL-17A (all cytokines supplemented at 10 ng/ml), for 6 hr, and then actinomycin D (5 μg/ml) was added to stop transcription. At the indicated time points, mRNA levels were assayed by quantitative RT-PCR, taking the expression level at the time of actinomycin.D addition as 100%. mRNA expression values are means±SD of three wells from a representative of three independent experiments.

FIGS. 14A and 14B. (FIG. 14A). WT MSCs or auf1$^{-/-}$ MSCs were first treated with IFNγ and TNFα with or without IL-17A (all cytokines supplemented at 5 ng/ml) for 12 hr, and then cocultured with T cell hybridoma A1.1 cells at a ratio of 1:10 for 12 hr. T cell proliferation was measured by 3H-Tdr incorporation, taking the proliferation level of A1.1 alone as 100%. (FIG. 14B). WT MSCs or auf1$^{-/-}$ MSCs were first treated with IFNγ and TNFα with or without IL-17A (10 ng/ml), IFNγ and TNFα were supplemented at different cytokine concentrations, for 12 hr, and then cocultured with T cell hybridoma A1.1 cells at a ratio of 1:10 for 12 hr. T cell proliferation was measured by 3H-Tdr incorporation, taking the proliferation level of A1.1 alone as 100%.

(FIG. 15A). Serum levels of ALT were measured. (n=3-5 mice per group). (FIG. 15B). Calculation of absolute numbers of mononuclear cells (MNCs) in liver tissues. (FIG. 15C). Absolute numbers of CD3$^+$CD4$^+$ and CD3$^+$CD8$^+$ T cells were determined by Flow Cytometry. (FIG. 15D). H&E staining of liver sections at 8h after ConA administration. a. Untreated mice; b. ConA+PBS; c. ConA+wild-type MSCs; d. ConA+IFNγ+TNFα pretreated wild-type MSCs; e. ConA+IFNγ+TNFα+IL-17A pretreated wild-type MSCs; f. ConA+auf1$^{-/-}$-MSCs; g. ConA+IFNγ+TNFα pretreated auf1-MSCs; h. ConA+IFNγ+TNFα+IL-17A pretreated auf1$^{-/-}$-MSCs.

(FIG. 16A) Construction of an inducible mouse nitric oxide synthase (iNOS) promoter-driven human indoleamine 2,3-dioxygenase (IDO) expression system in mesenchymal stem cells (MSCs). (FIG. 16B) Plasmid construction. (B) iNOS−/− MSCs, empty vector-transfected and human IDO-transfected iNOS−/− MSCs were stimulated with (+) and without (−) recombinant mouse inflammatory cytokines IFNγ and TNFα. The human IDO expression was measured by western blotting.

(FIG. 17A) Type I IFN (IFN α) inhibited IFN γ+TNF α-induced iNOS protein expression in MSCs, without affecting the related transcriptional factors in STAT1 and NFκB pathways. (FIG. 17B) Supplement of type I IFNs: IFNα or β strikingly inhibited MSC-mediated immunosuppression in MSC+splenocyte+anti-CD3 system. (FIG. 17C) FGF-2 (FGF B) inhibited the NO production which was induced by IFN γ+TNF α or IFN γ+IL-β in MSCs, reflected by nitrate content in the culture supernatants. (FIG. 17D) supplement of FGF-2 significantly reduced the immunosuppressive effect of MSCs in MSC+splenocyte+anti-CD3 system.

(FIG. 18A) To determine the efficiency of transduction, transduced cells were analyzed for GFP expression by flow cytometry. (FIG. 18B) MSC-GFP and MSC-IFNα were cultured at 5×10$^5$ per ml for 48h. Supernatants were collected and IFNα concentration was measured by IFNα Elisa Kit (PBL, NJ). (FIG. 18C) To test whether IFNα released by transduced cells had any biological functions, the surface expression of H-2Kb on MSC-GFP, MSC-GFP treated with recombinant IFNα (ebiosience, CA) or supernatant of MSC-IFNα and MSC-IFNα was examined by flow cytometry after staining with APC-H-2Kb (ebiosience, CA).

FIGS. 19A, 19B, 19C, 19D, 19E and 19F. (FIG. 19A). 1×10$^6$ B16 tumor cells with or without 1×10$^6$ MSC-GFP or MSC-IFNα were injected into C57BL/6 mice intramuscularly. Twelve days later, tumors were excised and weighed. (FIG. 19B) 1×10$^6$ B16 cells were intramuscularly with different numbers of MSC-IFNα: 1×10$^6$ (1:1), 1×10$^5$ (1:10), 1×10$^4$ (1:100), 1×10$^3$ (1:1000), 1×10$^2$ (1:10000) or no MSC-IFNα. Twelve days later, tumors were excised and weighed. (FIG. 19C). 1×10$^6$ B16 tumor cells with or without MSC-IFNα were injected into C57BL/6 mice intramuscularly. Mice survival was monitored for one hundred days after tumor inoculation. (FIGS. 19D and 19E) 1×10$^6$ B16 tumor cells were injected into C57BL/6 mice intramuscularly. After three (FIG. 19D) or four (FIG. 19E) days, 1×10$^6$ MSC-GFP or MSC-IFNα was inoculated intramuscularly. Twelve days after tumor inoculation, tumors were excised and weighed. (FIG. 19F). 1×10$^6$ B16 tumor cells were inoculated into C57BL/6 mice intramuscularly. Three days later, PBS, 5 μg recombinant IFNα or 1×10$^6$ MSC-IFNα were injected intramuscularly. After another nine days, tumors were excised and weighed. These experiments are repeated 2 to 3 times. Error bars, mean±s.d. for all plots. Statistical significance was assessed by unpaired two-tailed Student's t test.

(FIG. 20A) $1\times10^6$ luciferase labeled MSC-IFNα were intramuscularly injected into C57BL/6 mice together with $1\times10^6$ B16 cells. At D0, D3, D7, D15 and D21 after injection, MSC were detected by live imaging. Briefly, mice were anaesthetized, and 150 mg/kg of D-luciferin (Caliper Lifescience, MA) was given intraperitoneally 15 mins before imaging. BLI data was acquired with Berthod NC100 imaging system. (FIG. 20B). Luciferase signal intensities were calculated and presented (Error bars, mean±s.d.). (FIG. 20C) $1\times10^6$ B16 tumor cells with or without $1\times10^6$ MSC-IFNα were injected into C57BL/6 mice intramuscularly. Twelve days later, tumors were 0 collected. For HE and Ki-67 (Abcam, MA) staining, tumor samples were fixed in 10% formalin at room temperature for one week and paraffin sections were prepared. For TUNEL assay, tumors were embedded in OCT, frozen immediately, and sections were prepared for TUNEL assay with in situ cell death detection kit (Roche, Basel, Switzerland) following the producer's protocol.

(FIG. 21A). 1 000 B16 cells were seeded per well in 96-well plate with 0 ng/ml, 10 ng/ml or 100 ng/ml recombinant mouse IFNα. Three days later, cells were incubated for two hours with 10 ul CCK8 (Dojindo, Shanghai, China), and O.D.(450 nm) was measured. (FIGS. 21B and 21C) $1\times10^6$ B16 tumor cells with or without $1\times10^6$ MSC-GFP or MSC-IFNα were injected into C57BL/6 mice (FIG. 21B) or NOD-SCID (FIG. 21C) mice intramuscularly. Twelve days later, tumors were excised and weighed. (FIGS. 21D and 21E) $1\times10^6$ B16 tumor cells with $1\times10^5$, $1\times10^4$ MSC-IFNα or no MSC-IFNα were injected into C57BL/6 mice (FIG. 21D) or NOD-SCID mice (FIG. 21E) intramuscularly. Twelve days later, tumors were excised and weighed. (FIG. 21F). $1\times10^6$ B16 tumor cells with or without $1\times10^4$ MSC-IFNα were injected into C57BL/6 mice. NK cells-specific depletion antibody anti-asialo GM1 (Wako, Osaka, Japan) or vehicle control were i.v injected every four days from the day before tumor cell inoculation. Twelve days later, tumors were excised and weighed. (FIG. 21G) $1\times10^6$ B16 tumor cells with or without $1\times10^4$ MSC-IFNα were injected into C57BL/6 mice or β2m-deficient mice. Twelve days later, tumors were excised and weighed. These experiments are repeated 2 to 3 times. Error bars, mean±s.d. for all plots. Statistical significance was assessed by unpaired two-tailed Student's t test.

DETAILED DESCRIPTION OF INVENTION AND PREFERRED EMBODIMENTS

Figure 1:
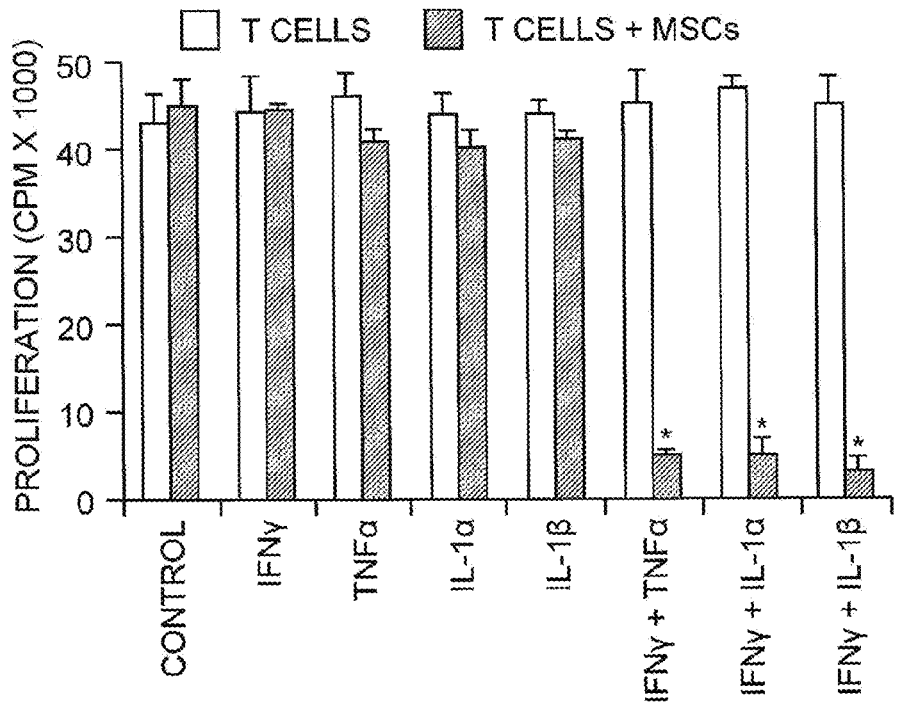
FIG. 1. is a graph showing that immunosuppression by MSCs is induced by proinflammatory cytokines. Cloned MSCs were supplemented with the indicated combinations of recombinant cytokines (20 ng/ml each) for 8 hours, then co-cultured with CD4+ T cell blasts at a 1:20 ratio (MSC:T cells), and proliferation assessed after an additional 8 hours. Values represent means±SD of five wells from a representative of three experiments with different clones. * p<0.001.

Unless defined otherwise, all technical and scientific terms used herein have the same meaning as is commonly understood by one of skill in the art to which this invention belongs and shall be understood to have the meanings described below. All publications and patents referred to herein are incorporated by reference in their entirety. In the case of conflict, the present specification, including definitions, will control. In addition, the materials, methods and examples are illustrative only and are not intended to be limiting.

As used herein, the term "about" will mean up to plus or minus 5% of the particular term.

As used herein, the phrase "consisting essentially of" refers to excluding other active ingredients or any other ingredient that can materially affect the basic characteristic of a composition, formulation or structure, but generally including excipients.

As used herein, invention an "effective amount" refers to that amount of stem cells, cytokines, or a therapeutic composition containing both, that is sufficient to modulate, attenuate, or induce an immune response (i.e., suppression of T cell responses or promotion of an immune response) in the subject thereby reducing at least one sign or symptom of the disease or disorder under treatment.

As used herein, the terms "treat," "treating," or "treatment" and the like refers to alleviating signs or symptoms of the disease accomplished by a administering a composition to a patient in need of such treatment. Such alleviation can occur prior to signs or symptoms of the disease appearing, as well as after their appearance, therefore it encompasses prophylactic and active treatment. In addition, "treat," "treating" or "treatment" does not require complete alleviation of signs or symptoms, or a cure. At a cellular level it may include reduction of diseased or target cellular population by at least 10%, 25%, 50%, 75%, 80%, 85%, 90%, 95%, or 99% as compared to untreated cells or cells treated with control or a comparative agent.

As used herein, the terms "administration" or "administering" or "treatment regimen" within the scope of the present invention includes a single therapeutic delivery, or multiple or repeated deliveries, or a control delivery therapeutic of any of the individual components of the present invention or in combination. Such terms are further meant to include modes of deliveries such as locally, systemically, intravascularly, intramuscularly, intra-peritoneally, inside the blood-brain barrier, organ-specific interventional injection or via other various routes.

Generally speaking, the present invention describes composition, methods, and kits employing inflammatory cytokines such as IL-1 α, interleukin beta (IL-1 B), TNF α, IL-17 A, IFN-I, TGF β, FGF to pretreat MSCs to augment their immunomodulating effects such as immunosuppressive or immune inducing effects, in prevention and treatment of various diseases such as multiple sclerosis, arthritis, lupus, sepsis, hepatitis, cirrhosis, Parkinson's disease, chronic infections, GvHD, and even cancer and solid tumors.

Immunosuppression is elicited by inflammatory cytokine, produced during an immune response. In the absence of inflammatory cytokines, MSCs do not gain their immunosuppressive properites. At least one aspect of the present invention describes the addition of inflammatory cytokines to prime and train MSCs for achieving a potent and long lasting inhibitory function toward immune response. Such affect could manifest particularly by the proliferation of activated T cells, or other immune response parameters including activated macrophages and other immune cells, serum levels of inflammatory cytokines such as IFNγ or TNFα.

The crucial role of inflammatory cytokines has been by in vivo studies on graft-versus-host disease (GvHD), experimental autoimmune encephalomyelitis, autoimmune hepatitis, chronic infections, liver cirrhosis, lung cirrhosis, and rheumatoid arthritis. In at least one aspect of the invention, genetically-modified MSCs are described that can reversely boost the immune response, owning to the secretion of a large amount of chemokines and growth factors by MSCs in the absence or reduced NO or IDO. Therefore, the present invention offers powerful suppressive and augmentative strategies to control the immune response.

At least one aspect of the invention is directed to a population of primed or trained stem cells that are obtained by a process of (i) obtaining multipotent progenitor cells from a cell source, (ii) culturing said multipotent cells in a suitable medium, (iii) separating mesenchymal stem cells from differentiated cells in said medium, (iv) activating at least a subset of said separated mesenchymal stem cells with IFNγ and at least one cytokine in effective amounts selected from the group consisting of IL-1 α, IL-1 β, IL-17A, TGF α, FGF, IFN-I (IFN α, β), TNF α, and any combinations thereof. In one embodiment of the present invention, a subset of these trained stem cells produced by such process enhance, boost, improve or induce immune response when administered to a subject in need thereof. In at least one embodiment, the subject is a mammal, preferably a human, or a human patient suffering from a disease. In another embodiment, another subset of trained stem cells are able to suppress, diminish or attenuate immune response at a site of interest.

At least one aspect of the invention is a process of making a population of primed or trained stem cells following the steps of (i) obtaining multipotent progenitor cells from a cell source, (ii) culturing said multipotent cells in a suitable medium, (iii) separating mesenchymal stem cells from differentiated cells in said medium, (iv) activating at least a subset of said separated mesenchymal stem cells with IFNγ and at least one cytokine in effective amounts selected from the group consisting of IL-1 α, IL-1 β, IL-17A, TGF α, FGF, IFN-I (IFN α, β), TNF α, and any combinations thereof. In one embodiment of the present invention, the process employs a specific medium that can achieve the optimal MSC properties. In another embodiment, the process includes a filteration or extraction step wherein all residual cytokines are substantially separated from the produced trained stem cells. Trained stem cells used herein refers to the stem cells produced by the process described herein and can consist of clonal, non-clonal or both types of stem cells.

In one embodiment, subsets of trained stem cells are able to suppress, diminish or attenuate immune response at a site of interest. In another embodiment, the present invention describes pharmaceutical reagents that block the immunosuppressive properties of other treatment or biological regimens such as interferon or vaccines. In another embodiment, the present invention describes compositions that block immunosuppressive properties of tumor associated MSCs to enhance immunity to immunosuppressive diseases such as cancer. Accordingly, MSC trained cells can be adjunctive to or be use in combination with other standard tumor immune therapy protocols to boost immune response under stress. Such immune therapy can include vaccines and cancer immunotherapies using genetically, biologically and pharmaceutically-modified MSCs, vaccines, protein or gene therapies as immune adjuvants.

In another aspect of the invention, a method for stimulating immune response is described in a subject in need thereof according to the steps of (a) administering to the subject an effective amounts of a composition containing an inhibitor to inducible nitric oxide synthase, an inhibitor to indoleamine 2, 3-dioxygenase, a population of inducible nitric oxide synthase (iNOS)-deficient mesenchymal stem cells, a population of indoleamine 2,3-dioxygenase (IDO)-deficient mesenchymal stem cells or any combinations thereo and (b) inhibiting the production of one or more of nitrogen oxide (NO), indoleamine 2, 3 dioxygenase (IDO), or prostaglandin E 2 (PGE2). In one embodiment, At least another aspect of the invention is directed to a composition including (a) a population of isolated mesenchymal stem cells produced by a method comprising the steps of: (i) obtaining multipotent progenitor cells from a cell source; (ii) culturing said multipotent cells in a medium to produce a subpopulation of mesenchymal stem cells and a subpopulation of differentiated cells; (iii) separating mesenchymal stem cells from differentiated cells in said medium, (iv) activating at least a subset of said separated mesenchymal stem cells with IFNγ and at least one cytokine in effective amounts selected from the group consisting of IL-1 α, IL-1 β, TGF β, FGF, IFN-I (IFN α, β), TNF α, and any combinations thereof; and optionally (b) a pharmaceutically acceptable carrier. In this aspect of the invention, the composition obtained induces the immune response of the subject receiving such composition. In another embodiment, such composition may be substantially free of any cytokines used during the expanding phase. The term substantially free as used herein is meant to be have less than 5%, 4%, 3%, 2%, 1%, 0.5%, 0.25% or 0.1% per weight of the composition. In another embodiment, the cell population may further contain cloned or non-cloned mesenchymal stem cells, differentiated cells, or a mixture thereof.

In another embodiment, the activation step of the MSCs is accomplished by presenting at least a subset of MSCs to IFNγ and at least one cytokine in effective amounts selected from the group consisting of IL-1 α, IL-1 β, IL-17 A, TNF α, and any combinations thereof for sufficient period of time to illicit the desired immunosuppressive properties. In this embodiment, the composition obtained contains isolated MSCs that suppress or attenuate the immune response in the subject receiving such composition both systemically or locally. In another embodiment, the composition is substantially free of any residual cytokines. In such embodiment, the composition suppresses local immune T-cell proliferation. In another embodiment, the cell population may further contain cloned or non-cloned mesenchymal stem cells, differentiated cells, or even a mixture thereof, wherein at least 50%, 60%, 70%, 75%, 80% or 90% of said population of cells are made of cloned MSCs.

In another aspect of the present invention, the inventors describe methods for activating, enhancing, boosting or inducing immune response in a patient in need thereof wherein a population of isolated MSCs are primed or trained by exposure to (a) isolated IFNγ and (b) at least one cytokine in effective amounts selected from the group consisting of IL-1 α, IL-1 β, TGF β, FGF, IFN-I (IFN α, β), TNF α, and any combinations thereof for sufficient period of time. As used herein, the phrase "sufficient period of time" within the scope of the present invention includes a time period necessary to train the MSCs to exhibit the desired properties. Such period of time ranges from at least 1 hour to about 4 week, including 12 hours, 24 hours, 36 hours, 48 hours, 72 hours and so on. In another embodiment, the cell population may further contain cloned or non-cloned mesenchymal stem cells, differentiated cells, or even a mixture thereof, wherein at least 50%, 60%, 70%, 75%, 80% or 90% of said population of cells are made of cloned MSCs.

In another embodiment, the population of isolated MSCs are administered separately or as a mixture with the isolated IFNγ and/or other cytokines. In at least another embodiment, the patient in need may be suffering from any one of an autoimmune disorder, allergy, sepsis, cirrhosis, cancer, viral infections and organ transplant.

In another aspect of the invention, the method of inducing immunosuppression employs a population of trained mesenchymal stem cells that are obtained by a specific process of (i) obtaining multipotent progenitor cells from a cell source such as a bone marrow, (ii) culturing such cells including the differentiated and multipotent stem cells in a suitable medium, (iii) separating mesenchymal stem cells from differentiated cells in said medium, (iv) activating at least a subset of said separated mesenchymal stem cells by exposing it for sufficient period of time to IFNγ and at least one cytokine selected from the group consisting of IL-1 α, IL-1 β, IL-17A, and TNF α. In at least one embodiment, the medium used to activate the mesenchymal stem cells are free of any other cytokine source.

In a preferred embodiment, the method of treating the subject in need includes administering effective amounts of a composition containing the trained mesenchymal cells locally to a site afflicted with a condition for treatment.

Another aspect of the present invention is directed to methods of inducing the expression of NO synthases (iNOS), indoleamine 2,3-dioxygenase (IDO) in at least a subset of said mesenchymal stem cells. In this aspect of the invention, increasing the concentration of NO, IDO metabolites at the site of treatment improves the clinical outcome.

In another aspect of the present invention, a population of MSCs is successfully transduced to release functional IFN α. In at least one embodiment, methods of using IFN α secreting MSC are described for treating cancer and controlling tumor growth.

In yet another aspect of the present invention, populations of trained stem cell are described in a therapeutic kit for use in a clinical setting. In at least one embodiment, the therapeutic kit further contains IFNγ and at least one cytokine such as IL-1 α, IL-1 β, IL-17A, IFN-I, TGF β, FGF, TNF α, and any combinations thereof. In particular embodiments, therapeutic kits may be assembled to be used for immunosuppression or immune-enhancement with appropriate instruction to trigger such immune response respectively. In one embodiment, the kit may consist essentially of trained MSCs, IFNγ and at least another second cytokine, but free of any other active ingredients that would materially alter the behavior of the trained MSCs.

In one embodiment, the therapeutic kit for immunosuppression contains a population of trained stem cells, IFNγ and at least one cytokine such as IL-1 α, IL-1 β, IL-17A, TNF α, and any combinations thereof. In another embodiment, the therapeutic kit for immune enhancement contains a population of trained cloned stem cells, IFNγ and at least one cytokine such as IL-1 α, IL-1 β, IFN-I, TGF, TNF α, and any combinations thereof. In another embodiment, the cytokines are isolated type. In another embodiment, the instructions for using the kit articulate the steps for triggering the desired clinical outcome.

In yet another embodiment, a method for stimulating immune response in a patient in need suffering for example from cancer or a viral infection is described. In such embodiment, patients are administered effective amounts of a composition comprising an inhibitor to inducible nitric oxide synthase, an inhibitor to indoleamine 2, 3-dioxygenase, a population of inducible nitric oxide synthase (iNOS)-deficient mesenchymal stem cells, a population of indoleamine 2,3-dioxygenase (IDO)-deficient mesenchymal stem cells or any combinations thereof. In a preferred embodiment, the method cause inhibition of the production of one or more of nitrogen oxide (NO), indoleamine 2, 3 dioxygenase (IDO), or prostaglandin E 2 (PGE2), 1-MT, 1400W, L-NMMA or other suitable agents. In this embodiment, the above mentioned inhibitors of iNOS or IDO are administered individually or as a mixture. In this aspect of the invention, the patient's status is post receiving a regimen of immune therapy including a regimen including the trained or primed MSCs described herein, or another immune therapy regimen which can include treatment with indicated interferons, antibody, cell therapy or other therapies that modulate immune response.

Another aspect of the present invention describes methods for screening reagents or drugs to inhibit or increase IDO activity in mammal MSCs, including human or mouse MSCs, by construction of human IDO-expressing mouse iNOS-deficient cells in which IDO protein consisting of the amino acid sequence encoded by the human IDO gene under the control of mouse iNOS promoter, thereby improve the immunosuppressive function of MSCs. This aspect of the invention describes methods to screen reagents or drugs to enhance or inhibit IDO activity in mouse model with human IDO expression controlled by mouse iNOS promoter, such that said administration regulates IDO activity, thereby treat the disease involved in IDO abnormal expression in cancer or infections, especially in combination with immune therapies.

The human mesenchymal stem cells can be derived from a number of cell source, for example, from placental derivatives or from bone marrow, or obtained from a number of different sources, including plugs of femoral head cancellous bone pieces, obtained from patients with degenerative joint disease during hip or knee replacement surgery, and from aspirated marrow obtained from normal donors and oncology patients who have marrow harvested for future bone marrow transplantation. Although the harvested marrow is generally prepared for cell culture separation by a number of different mechanical isolation processes depending upon the source of the harvested marrow (i.e., the presence of bone chips, peripheral blood, etc), the critical step involved in the isolation processes is the use of a specially prepared medium that contains agents that allow for not only mesenchymal stem cell growth without differentiation, but also for the direct adherence of only the mesenchymal stem cells to the plastic or glass surface area of the culture dish.

By producing a medium that allows for the selective attachment and survival of the desired mesenchymal stem cells, which are present in the marrow samples in very minute amounts, it is possible to separate the mesenchymal stem cells from the other cells (i.e., red and white blood cells, fibroblasts, other differentiated mesenchymal cells, etc.) present in the bone marrow. Other sources of human MSCs include umbilical cord, fat tissue and tooth root. MSC are multipotent progenitors for a variety of cell types of mesenchymal cell lineage, including bone, cartilage, fat, tendon, nerve tissue, fibroblasts and muscle cells. Mesenchymal stem cells can be isolated and purified form tissue such as bone marrow, blood (including peripheral blood), periosteum, and dermis, and other tissues which have mesodermal origins. In this regard, it has been found that although these progenitor cells are normally present in bone marrow, for example, in very minute amounts and that these amounts greatly decrease with age (ie. From about 1/10,000 cells in a relatively young patient to as few as 1/2,000,000 in an elderly patient), human mesenchymal stem cells can be isolated from various tissues and purified when cultured in a specific medium by their selective attachment, termed "adherence" to substrates.

Mesenchymal stem cells are typically identified based upon the expression or lack of expression of particular markers. For example, MSCs are CD34−, CD1 1 b, CD11c−, CD45−, MHC class II, CD44+, Sca-1+, and MHC class I low. In addition, MSCs can be identified by their ability to differentiate into various mesenchymal cell types. In vitro experiments have demonstrated that culture conditions, additives, growth factors and cytokines can precisely induce MSC to develop into a selected mesenchymal cells. For example, dexamethasone in combination with isobutilmethylxanthine or insulin or a mixture of isobutilmethylxanthine, insulin and indomethacin has been shown to push the MSCs toward differentiating into adipocytes. Similarly, MSCs can differentiate into skeletal muscle cells when stimulated with 5-azacytidine. 13-VGF has been shown to cause mesenchymal stem cells to differentiate into cardiac muscle cells.

While the invention is not limited to the use of MSCs obtained by any particular method, MSCs can be isolated from bone marrow and umbilical cord, purified and culturally expanded by any methodology acceptable in the art. Plugs or aspirates of bone marrow cells (consisting predominantly of red and white bold cells, and a very minute amount of mesenchymal stem cells) are passed through syringes to dissociate the tissue into single cells. In a preferred embodiment a population multipotent progenitor cells are obtained from a suitable source such as bone marrow, umbilical cord or fat tissue, further cultured and expanded in a suitable medium typically containing glutamine. Then mesenchymal stem cells are identified and from differentiated cells and further expanded in a medium containing IFNγ and at least one cytokine selected from the group consisting of IL-1 α, IL-1 β, IL-17A, IFN-I, TGF, FGF, TNF α, and any combinations thereof. In another embodiment, the clonal mesenchymal stem cells are identified and from differentiated cells and further expanded in a medium containing IFNγ and at least one cytokine selected from the group consisting of IL-1 α, IL-1 β, IL-17A, IFN-I, TGF, FGF, TNF α, and any combinations thereof. In either case, the meshenchymal stem cells expanded in such medium are trained and programed to suppress or enhance immune response in particular clinical setting.

In one embodiment, the multipotent progenitor cells are cultured in suitable medium such as complete medium (e.g., MEM medium with 10% fetal bovine serum) and humidified atmosphere. The media is not changed for at least one day to allow the cells to attach to the culture dish. Thereafter the media is replaced every 3-4 days. When the cells have grown to confluence, the cells are detached from the culture dish, preferably with trypsin. Cells can be subcultured in serum-free media after removal or inactivation of the trypsin. Additional methods for isolating and culturing mesenchymal stem cells are provided in U.S. Patents Application Nos. 20070160583 and 20070128722 incorporated herein in their entirety. MSCs can also be isolated from Wharton's jelly of the umbilical cord using similar methods.

In one embodiment, the isolated mesenchymal stem cells of this invention can be a subset of a heterogeneous cell population including certain differentiated cells. In another embodiment, the isolated mesenchymal stem cells are homogeneous composition containing only trained clonal MSCs. In another embodiment, the MSCs can be a mixed cell population enriched in MSCs. In this regard, an isolated population of MSCs is composed of at least about 75% MSCs, or at least about 83%, 84%, 88%, 89%, 90%, 91%, 93%, 95%, 96%, 97%, or 98% cloned MSCs, while the rest can include differentiated cells, progenitor cells, blood cells, or any other suitable cells that would enhance the clinical outcome.

In effective amount refers to that amount of MSCs and cytokines that is sufficient to attenuate an immune response (i.e., suppression of T cell responses) in the subject thereby reducing at least one sign or symptom of the disease or disorder.

The mesenchymal stem cells used in accordance with the invention are, in order of preference, autologous, allogenic or xenogeneic, and the choice can largely depend on the urgency of the need for treatmen The cytokines of the present invention can be obtained by conventional purification methods, by recombinant technologies or from commercial sources. For example, the amino acid sequence of interferon-gamma (IFNγ) is provided under GENBANK Accession Nos. NP 000610 (human) and NP 032363 (mouse). Commercial sources of IFN protein include, e.g., INTERMUNE (Brisbane, Calif.) and PeproTech, Inc. (Rocky Hill, N.J.). Likewise, tumor necrosis factor-alpha (TNFα, cachexin or cachectin) is provided under GENBANK Accession Nos. NP 000585 (human) and NP 038721 (mouse) and commercially available from sources such as ProSpec Bio (rehovot, Israel) and Pepro-Tech, Inc. Similarly, human interleukin 1-alpha (IL1α) and interleukin 1-beta (IL1β) are known under Accession Nos. P01583 and P01584, respectively, and are available from commercial sources such as ProSpec Bio and PeproTech, Inc. Interleukin 17A (IL17A) known under Accession Nos. BC067505 (human) and NM 010552 (mouse). When used in accordance with this invention, the cytokines are "isolated", i.e., either homogenous (100%) or near homogenous (90 to 99%). In particular embodiments, the cytokines are recombinant proteins.

Interleukin 17A is one of the key inflammatory cytokines, primarily produced by IL-17 producing CD4$^+$ T cells (Th17) cells which is a well-known cytokine for its proinflammatory functions in inflammatory and autoimmune responses. IL-17A signals through a heteromeric receptor complex, IL-17RA and IL-17RC. Upon IL-17A binding, IL17RA recruits Act 1, a critical downstream mediator of the IL-17A-induced signaling process. Although much is known about IL-17A-induced signaling pathways and the role of IL-17A in inflammatory and autoimmune diseases, its cellular targets and mode of action remain elusive.

The present invention employs IL-17A alone or in combination with other cytokines to facilitate trained MSCs that cause immune suppression. The above-referenced MSCs and cytokines can be in the form of a composition, e.g., a pharmaceutical composition suitable for administration to a subject in need of treatment with the same. The compositions of the invention can be administered by any conventional method including parenteral (e.g., subcutaneous or intramuscular) or intravenous injection, intravenous infusion, specific organ intervention or topical application. The treatment can be composed of a single dose or a plurality of doses over a period of time.

The pharmaceutical composition typically contains at least one acceptable carrier. The carrier must be "acceptable" in the sense of being compatible with the MSCs and cytokines and not deleterious to the recipients thereof. Typically, the carrier can be a suitable isotonic solution such as phosphate-buffered saline, culture media, such as DMEM, physiological saline with or without albumin, 5% aqueous dextrose, and/or mixtures thereof, and other suitable liquids known to those skilled in the art.

In a preferred embodiment for use therapeutically, the pharmaceutical composition of the invention can also be provided as a kit. A kit of the invention can contain only a pharmaceutically acceptable carrier; an isolated population of mesenchymal stem cells stimulated or trained with isolated IFN γ isolated IL-1α; and isolated IL17A and further instructions for using the kit in a method for attenuating an immune response. In this aspect of the invention, the cells stimulated with cytokine components of the kit can be administered. The kit also optionally may include a means of administering the cells, for example by injection. In an optional embodiment, the compositions of this invention suitable for parenteral administration can further contain antioxidant(s) in combination with one or more pharmaceutically-acceptable sterile isotonic aqueous or nonaqueous solutions, suspensions or in the form of sterile lyophilized powders which may be reconstituted into sterile injectable solutions or dispersions just prior to use, which may contain the combination of the antioxidants, minerals and vitamins, buffers, solutes which render the final formulation isotonic.

The present invention further provides a composition comprising a population of isolated cloned MSCs, isolated IFNγ, isolated IL-1 α or β, and isolated IL-17A in admixture with a pharmaceutically acceptable carrier. In another embodiment, the present invention provides a composition comprising a population of isolated MSCs, isolated IFNγ, isolated TNF α, and isolated IL-17A in admixture with a pharmaceutically acceptable carrier. In an embodiment, the composition also comprises isolated IL-1 α or β. The methods of use of such kits provide for attenuating an immune response following the steps of administering an effective amount of MSCs, isolated IFNγ, isolated IL-1 α, TNF α, and isolated IL-17A to a subject in need of a treatment thereby attenuating the subject's immune response.

The present invention provides a method for attenuating an immune response comprising administering an effective amount of isolated mesenchymal stem cells, isolated IFNγ, isolated IL-1 α, and isolated IL-17A to a subject in need of a treatment thereby attenuating the subject's immune response. In an embodiment, the method further comprises isolated TNF-α.

In another embodiment, the treatment is directed towards multiple sclerosis, arthritis, lupus, sepsis, hepatitis, cirrhosis, Parkinson's Disease, chronic infections and graft-versus-host disease. In another embodiment, the MSCs are provided as a pharmaceutical composition, wherein the MSCs are formulated with a cytokine cocktail prior to administration. In another embodiment, the MSCs and cytokines are administered as individual components. A subject in need of treatment can be a mammal (e.g., a human, monkey, cat, dog, horse, etc.) with a particular disease or disorder associated with an adverse immune response. In particular embodiments, the subject is human.

Effectiveness can also be determined by monitoring iNOS, IDO, and/or chemokine expression. Subjects benefiting from attenuation of an adverse immune response include subjects having or suspected of having an autoimmune disorder (e.g., rheumatoid arthritis, diabetes mellitus type 1, systemic lupus erythematosus, scleroderma, GvHD, cirrhosis or psoriasis), allergy (e.g., hay fever), or sepsis. In addition, because inflammation orchestrates the microenvironment around tumors, contributing to proliferation, survival and migration, certain cancer patients may also benefit from the present composition.

In organ transplant and bone marrow transplant, T cells of donor origin can recognize the recipient's MHC and lead to the development of GvHD. This often fatal disease is frequently unresponsive to various immunosuppressive therapies but new approaches targeting immune modulatory molecules show great promise in treating GvHD. Most recently, MSCs have been shown to be highly effective in the treatment of GvHD in pre-clinical and clinical trials. The analysis presented herein further demonstrates that MSC activity is mediated via the production of NO or IDO after stimulation with pro-inflammatory cytokines. Accordingly, the composition of this invention finds use in organ transplantation or treatment of GvHD.

In vivo determination of suitable doses can be accomplished using art-accepted animal models such as the DTH and GvHD models described herein. However, as the present involves treatment under the care of a physician or veterinarian, adjustments can be made to the amount and timing of treatment during the course of treatment, based on the evaluation of the effectiveness of the treatment, which can vary from subject to subject. In addition, treatment can be provided at particular stages of immune responses in patients as described by the physician or veterinarian.

The present invention also provides a method for enhancing the efficacy of an immune therapy of cancer by administering to a subject receiving an immune therapy treatment and effective amount of an NOS and/or IDO inhibitor. In particular embodiments, the inhibitors are IDO and iNOS-selective inhibitors, e.g., as disclosed herein. An effective amount of such an inhibitor is an amount which provides at least a 50%, 60%, 70%, 80%, 90%, 95%, or 97% decrease in the amount of NO production and/or IDO activity upon administration of the immune therapy as compared to a subject not receiving the inhibitors. In a particular embodiment, the method provides enhancing the therapeutic effectiveness of an interferon treatment (e.g. IFNγ) using an IDO and/or iNOS-selective inhibitor.

The present invention provides a method for modifying MSCs with inflammatory cytokines prior to administration into patients. This method would dramatically enhance the efficacy of MSCs in clinical settings. In at least one aspect critical roles of iNOS and chemokines in the immunosuppressive effect of MSCs, with the co-presence of IFNγ and another cytokine, either TNFα, IL-1α or IL-1β as the requisite are described. In another aspect, MSCs has been shown to switch to promote immune responses when inflammatory cytokines IFNγ and TNFα were inadequate to induce sufficient immunosuppression.

At least in one embodiment, the role of IL-17A to change the dynamic of the interaction between MSCs and inflammatory cytokines is described. The present inventors have discovered that IL-17A enhances the immunosuppressive function of MSCs, even in the presence of low dose of inflammatory cytokines IFNγ and TNFα. Unlike its traditional role of promoting immune responses, as shown herein, IL-17A plays an important role in immunosuppression in the presence of MSCs. Thus, in certain circumstances, blocking the activity of IL-17A can induce or enhance immune response. In at least one embodiment, the pathophysiological roles of IL-17A is described.

IL-17A is critical in promoting inflammation and autoimmunity. Those of ordinary skill in the art can appreciate that for the first time the role of IL-17A in enhancing immunosuppression in MSCs is substantiated. Previously, IL-17A have been widely reported to exacerbate disease progress in multiple autoimmune diseases, including rheumatoid arthritis (RA), multiple sclerosis (MS) and inflammatory bowel disease (IBD), in which the IL-17A level is dramatically elevated. In addition, disease progression slows down when IL-17A is genetically ablated or IL-17A blocking antibody is administered.

However, IL-17A not always promotes immune responses, since past reports suggest that IL-17A has a protective function in gut inflammatory disorders. Genetic ablation or neutralization of IL-17A can actually aggravate disease progress in the dextran-sulphate-sodium (DSS) induced colitis model. In such context, those of ordinary skill in the art can appreciate that at least one aspect of the present invention provides that IL-17A enhance the immunosuppressive property of MSCs. In at least one embodiment, it is contemplated that MSCs may not suppress immune responses effectively without IL-17A.

In yet another aspect of the present invention, the inventors demonstrated a new function of IL-17A in enhancing immunosuppression through a novel cell target, mesenchymal stem cells. Similarly it has been shown that IL-17A exerts these effects by reversing the suppression of gene expression conferred by mRNA decay factor AUF1.

In at least one embodiment of the present invention, Concanavalin A ("ConA") induced liver injury in mice is employed for investigating the pathophysiological process of autoimmune or viral fulminant hepatitis, in which T cell responses play a pivotal role in mediating liver damage. As suppression of T cells responses can dramatically attenuate ConA induced liver injury and adipose tissue derived stromal cells have been shown to reduce ConA induced liver damage; the present inventors used bone marrow derived MSCs and investigated the role of IL-17A in modulating MSC-mediated treatment of liver injury. Thus, at least one aspect of the present invention provide that IL-17A can dramatically enhance the immunosuppressive effects of MSCs.

The present invention further provides that MSCs can only marginally affect the progression of ConA-induced liver injury, because the immunosuppressive capacity of MSCs requires stimulation by inflammatory cytokines. Although many cytokines can be produced after ConA administration in vivo, these cytokines may only remain at high levels for a short time and not able to stimulate MSCs effectively when administered at a later time. Therefore, naive MSCs are not effective in attenuating ConA induced liver injury.

Accordingly, at least one aspect of the invention provides the new and novel function of IL-17A in enhancing immunosuppression through a novel cell target, mesenchymal stem cells. It is further contempelated that IL-17A may exert these effects by reversing the suppression of gene expression conferred by mRNA decay factor AUF1. As described herein, IL-17A is a factor for enhancing MSC-mediated immunosuppression.

In certain cases, the inventors have found the need to control such immunosuppressive effect in vitro and in vivo, either positively or negatively. In one embodiment the inventors screened the available growth factors and cytokines, and found among them, there were two factors strikingly down-regulating MSC-mediated immunosuppression: type I interferons and fibroblast growth factor (FGF-2).

Figure 16:
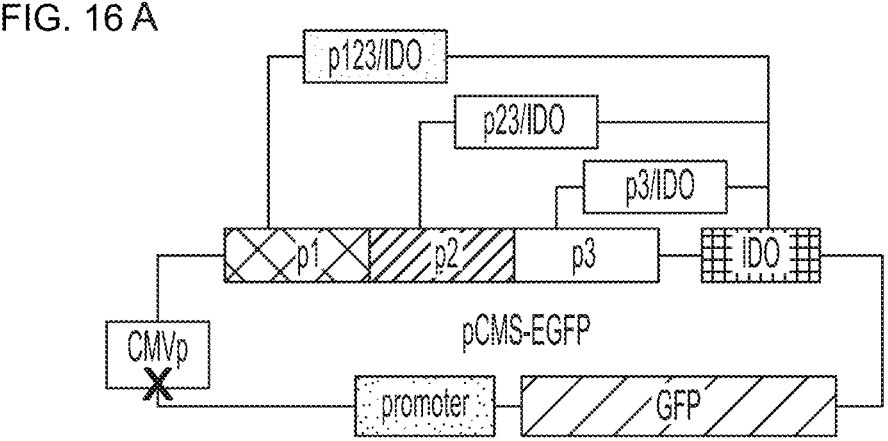
FIGS. 16A and 16B.
Figure 16:
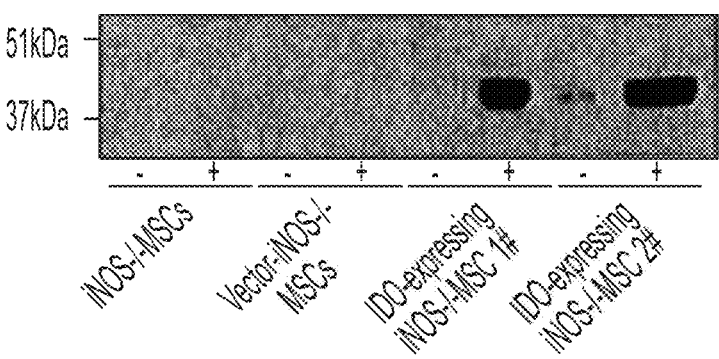
Figure 17A:
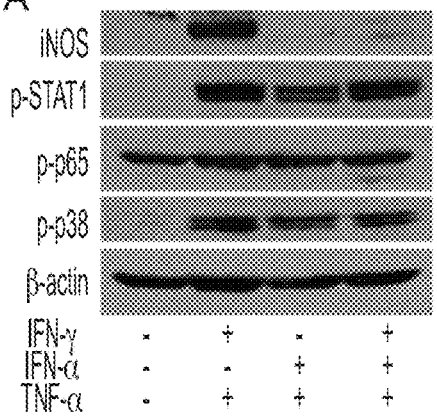
FIGS. 17A, 17B, 17C and 17D. Type I interferons and FGF-2 down-regulate the immunosuppressive effect of MSCs through attenuation NO production.
Figure 17B:
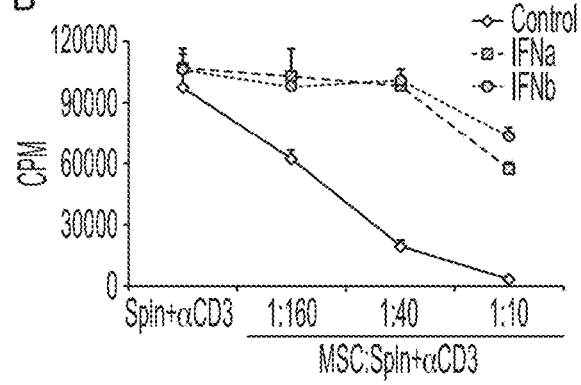
Figure 17C:
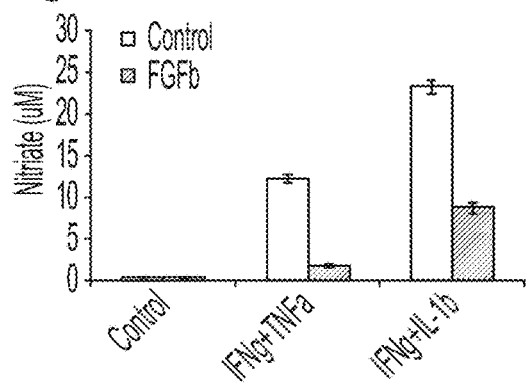
Figure 17D:
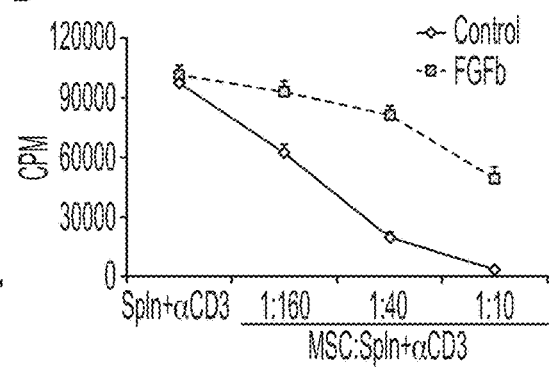

Type I interferons (IFNs), are a family of cytokines which render the host immunity to eradicate viruses and other intracellular infections, whereas FGF-2 (FGF-β, basic fibroblast growth factor) belongs to a family of genes encoding heparin-binding proteins with growth, antiapoptotic, and differentiation activity. However, no studies have related these two cytokines with regulation of immunosuppression. Type I interferons and fibroblast growth factor (FGF-2) serve as negative regulators on MSC-mediated immunosuppression through down-regulation of iNOS expression. As described herein, inventors found that these two factors could potentially inhibit the immunosuppressive effect of MSCs towards T-cell proliferation (FIGS. 16A, 16B). Further analysis revealed that, supplement of either of these cytokines was able to strikingly reduce the expression of iNOS protein and NO production (FIGS. 17A-D).

The following non-limiting examples are provided to further illustrate the present invention.

EXAMPLES

Example 1

Materials and Methods

Mice. Male C57BL/6, C3H/HeJCr and F1 (C57BL/6xC3H) mice, 6-8 weeks old, were from the National Cancer Institute (Frederick, Md.). IFNγ-R1$^{-/-}$ mice and iNOS-mice were from Jackson Laboratory (Bar Harbor, Me.). Mice were maintained in the Robert Wood Johnson Medical School Vivarium. Animals were matched for age and gender in each experiment, all approved by the Institutional Animal Care and Use Committee.

Reagents. Recombinant mouse IFNγ and TNFα, IL-1α, and IL-1β monoclonal antibodies against mouse TNFα, IL-1 α, IL-1β, and CCR5, FITC-conjugated anti-mouse CD11b, and PE-conjugated anti-mouse F4/80 were from eBiosciences (La Jolla, Calif.). Recombinant mouse M-CSF and antibodies against IL-10 and TGF-β. were from R&D Systems (Minneapolis, Minn.). Anti-IFNγ was from Harlan (Indianapolis, Ind.). Anti-CXCR3 was from Invitrogen (Carlsbad, Calif.). Indomethacin, 1-methyl-DL-tryptophan (1-MT), and N G-monomethyl-L-arginine (L-NMMA) were from Sigma-Aldrich (St. Louis, Mo.).

Cells. MSCs were generated from bone marrow of tibia and femur of 6-10 week old mice. Cells were cultured in α MEM medium supplemented with 10% FBS, 2 mM glutamine, 100 U/ml penicillin, and 100 μg/ml streptomycin (all from Invitrogen). Non-adherent cells were removed after 24 hours, and adherent cells were maintained with medium replenishment every three days. To obtain MSC clones, cells at confluence were harvested and seeded into 96-well plates by limited dilution. Individual clones were then picked and expanded. Cells were used at 5th to 20th passage.

T cell blasts were generated from CD4$^+$ T cells purified by negative selection with CD4$^{-/-}$ T cell subset isolation kits (R&D Systems). Cells (1×10$^6$ cells/ml) were activated by plastic-bound anti-CD3 and soluble anti-CD 28 for 48 hours, then cultured with IL-2 (200 U/ml) alone for 48 hours. All T cell cultures were maintained in RPMI-1640 medium supplemented with 10% heat-inactivated FBS, 2 mM glutamine, 100 U/ml penicillin, 100 μ·g/ml streptomycin, and 50 mMβ-ME (complete medium).

Activated splenocyte supernatant was harvested from 48 hour-cultures of splenocytes (2×10$^6$/ml) activated by plastic-bound anti-CD3, then filtered with a 0.1 μm filter and frozen.

Detection of Cytokines, Chemokines, and NO. Culture supernatants were assayed for 20 different cytokines and chemokines with a multiplex bead array kit (Invitrogen, Carlsbad, Calif.) using Luminex Technology (Bio-Plex System, Bio-Rad, Hercules, Calif.). IFNγ was assayed by ELISA (BD Biosciences, San Jose, Calif.). NO was detected using a modified Griess reagent (Sigma-Aldrich). Briefly, all NO3 was converted into NO2 by nitrate reductase, and total NO2 detected by the Griess reaction (Miranda, et al. (2001) Nitric Oxide 5:62-71).

Real-Time PCR. RNA was isolated from cell pellets using an RNEASY Mini Kit. First-strand cDNA synthesis was performed using SENSISCRIPT RT Kit with random hexamer primers (all kits from Qiagen, Valencia, Calif.). mRNA of the genes of interest were quantified by real-time PCR (MX-4000 from Stratagene, La Jolla, Calif.) using SYBR Green Master Mix (Applied Biosystems, Foster City, Calif.). Total amount of mRNA was normalized to endogenous .beta.-actin mRNA. Primers sequences for iNOS were: forward, 5'-CAG CTG GGC TGT ACA AAC CTT-3' (SEQ ID NO:1); reverse, 5'-CAT TGG AAG TGA AGC GTT TCG-3' (SEQ ID NO:2). Other primers were from the RT2 PRO-FILER™ PCR Array Mouse Chemokines & Receptors kit (Superarray, Frederick, Md.).

Chemotaxis Assay. Chemotaxis was tested with the NeuroProbe CHEMOTX Chemotaxis System (NeuroProbe, Gaithersburg, Md.), as described (Shi, et al. (1993) J. Immunol. Meth. 164:149-154). The lower chambers of the 96-well plate were filled with supernatant from MSCs stimulated with IFNγ plus TNFα (20 ng/ml each or Sup.CD3-act (1:2 dilution). A polyvinylpyrrolidine-free polycarbonate membrane with 5 µm pores was then overlaid. T cell blasts ($1.25 \times 10^5$) were added to the top chambers. After a 3-hour incubation, cells that had migrated through pores and into bottom wells were quantified using MTT assay (Shi, et al. (1993) supra). A chemotaxis index was calculated as the ratio of the number of T cell blasts migrated in response to MSCs compared to the number migrating to medium alone.

The immunosuppression resulting from T cell migration toward inflammatory cytokine-activated MSCs was examined in a similar set-up. MSCs ($2 \times 10^4$) were added to the lower chamber with or without stimulation with IFNγ and TNFα (20 ng/ml each) for 24 hours. Activated T cell blasts were then added to the upper chamber, as above. IL-2 was added to both chambers. After 3 hours, both chambers were pulsed with $^3$H-thymidine, and cell proliferation assessed 6 hours later.

GvHD Induction and Modulation by MSCs. C57BL/6× C3H F1 mice at 8-weeks old were lethally irradiated (13 Gy) and after 24 hours were infused by tail vein injection with nucleated bone marrow cells ($5 \times 10^6$) and splenocytes ($5 \times 10^6$) isolated from C57BL/6 parent mice. On days 3 and 7 following bone marrow transplantation, the recipients were administered with $0.5 \times 10^6$ MSCs derived from C57BL/6 wild-type, IFNγ R1$^{-/-}$, or iNOS$^{-/-}$ mice via the tail vein. Some wild-type MSC groups were also injected i.p. with the iNOS inhibitor, NG-monomethyl L-arginine (L-NMMA, 500 µg/mouse), anti-IFNγ (400 µg/mouse), or a cocktail of three antibodies against TNFα, IL-1α and IL-1β (200 µg each/mouse) daily for 7 days starting immediately after the first MSC administration. As negative controls, the F1 mice were injected with F1 bone marrow cells. Mice were observed daily for GvHD signs (wasting, ruffled hair, and hunched back) and euthanized upon becoming moribund, thus marking survival time. On day 14, various tissues were collected and 5 µm paraffin sections prepared and stained with hematoxylin/eosin (H&E).

Induction of DTH Response and Histology Analysis. C57BL/6 mice (6-8 weeks old) were immunized by tail base injection of ovalbumin (OVA, 10 µg in 50 µl saline) emulsified with 50 ul complete Freund's adjuvant. DTH was tested after 5 days, by challenging with 200 µ·g aggregated OVA in 30 µl saline injected into the right hind footpad. The left footpad was injected with 30 ul of saline as a negative control. After 24 hours, antigen-induced footpad thickness increment was measured using a caliper and calculated as: (Rimm-Limm)–(R.unimm-L.unimm), where R and L are thickness of right and left footpads.

Statistical Analysis. Significance was assessed by unpaired two-tailed Student's t-test or analysis of variance (ANOVA).

Example 2

Immunosuppressive Function of MSCs is Induced by Proinflammatory Cytokines.

To identify the underlying mechanisms, clones of mouse MSCs were employed. The stem cell characteristics of these clones were defined by their ability to differentiate into adipocytes or osteoblasts and by their expression of surface markers: CD34; CD11b; CD11c; CD45; MHC class II; CD44$^+$; Sca-1$^+$; MHC class II$^{low}$. All results presented herein were replicated using at least three different MSC clones.

Since most reported studies of immunosuppression by MSCs are based on their effects on T cell proliferation and cytokine production, the effect of MSCs was first examined on the IL-2-driven proliferation of T cell blasts. Fresh CD4$^+$ T cell blasts were generated from splenocytes by activation with anti-CD3 followed by expansion with IL-2 for several days (Devadas, et al. (2006) Immunity 25:237-247; Radvanyi, et al. (1996) Cell Immunol. 170:260-273). T cell blasts were added at a 1:20 ratio (MSC:T cells) along with IL-2 (200 U/ml). Cell proliferation was assessed by $^3$H-Tdr incorporation after 8 hours. Surprisingly, it was found that the IL-2 driven proliferation of these T cell blasts was unaffected by the addition of MSCs. MSCs also had no effect on the proliferation of T hybridoma A1.1 cells. These T cells blasts and T hybridoma cells, however, produce no cytokines unless reactivated through the TCR (Fotedar, et al. (1985) J. Immunol. 135(5):3028-33). Thus, in the absence of T cell cytokines, MSCs were unable to suppress T cell proliferation.

To examine the possibility that cytokines induce the immunosuppressive capacity of MSCs, these culture conditions were reproduced by combining MSCs and fresh splenocytes at graded ratios in the presence of anti-CD3. The results of this analysis indicated that T cell proliferation was completely blocked when MSCs were added at a ratio as low as 1:60 (MSC to splenocyte). Importantly, to exert their immunosuppressive effect, MSCs do not have to be syngeneic. A similar effect was found on purified CD4$^+$ or CD8$^+$ T cells activated by plastic-bound anti-CD3 antibody and anti-CD28 using MSCs from between the 5th and 20th passage. Thus, under conditions in which MSCs and T cells are in co-culture during T cell activation, the resultant T cell response was strongly suppressed by MSCs, indicating that T cell-produced cytokines may have a role. The immunosuppressive capacity of MSC clones generated from different mouse strains was also examined. It was observed that those clones that exhibited better differentiation potential had a greater capacity for immunosuppression.

To determine whether cytokines secreted by activated T cells are responsible for the induction of immunosuppression by MSCs, mixed co-cultures of MSCs with T cell blasts (as described above) were supplemented with supernatant from a culture of anti-CD3-activated splenocytes. The resultant T cell proliferation was greatly inhibited. It was also observed that the proliferation of A1.1 cells in co-culture with MSCs was inhibited by supplementation with the activated splenocyte supernatant. These experiments indicate that some product(s) of activated T cells is required to induce immunosuppression by MSCs. To identify the culpable cytokine(s), the activated splenocyte supernatant was treated with neutralizing antibodies against various cytokines before addition to the co-cultures. This analysis indicated that neutralization of IFNγ completely reversed the inhibition of proliferation of T cell blasts co-cultured with MSCs supplemented with the anti-CD3 activated splenocyte supernatant. These results implicate IFNγ as a key cytokine in this process, and reveal that under certain conditions this major proinflammatory cytokine can instead mediate immunosuppression.

The effect of IFNγ was then tested directly by adding isolated recombinant IFNγ (20 ng/ml) instead of activated splenocyte supernatant to the mixed co-cultures of MSC+ T cell blasts or MSC+A1.1 cells. Surprisingly, IFNγ alone did not induce immunosuppression. Several other proinflammatory cytokines were then added (20 ng/ml each) and it was found that concomitant addition of either TNF α, IL-1α, or IL-1β along with IFNγ was required to achieve suppression of T cell proliferation in co-cultures with MSCs (1:20 ration MSC:T cells) (FIG. 1). Therefore, induction of the immunosuppressive function of MSCs by anti-CD3-activated splenocyte supernatant may be due to IFNγ acting in concert with either TNFα; IL-1α; or IL-1β on the MSCs. Thus, while IFNγ is absolutely required, this cytokine alone is not sufficient; proper immunosuppression signaling in MSCs requires the concerted action of IFNγ and any of the other three cytokines.

Neutralizing antibodies against TNFα; IL-1α; or IL-1β, individually or together, were added to the activated splenocyte supernatant before addition to mixed co-cultures of MSCs and T cell blasts. While individual antibodies had no effect, simultaneous blockade of all three cytokines completely reversed the inhibition of T cell proliferation. Other cytokines, such as GM-CSF (Granulocyte-macrophage colony-stimulating factor) and IL-6 (Interleukin-6), had no effect. The data herein indicate that the combination of the IFN with any of the other three proinflammatory cytokines, TNFα, IL-1α or IL-1β is fully responsible for inducing the ability of MSCs to inhibit T cell proliferation, and that TNFα, IL-I α, and IL-I β are interchangeable in acting together with IFNγ.

It is contemplated that MSCs must encounter some level of IFNγ arising from initial T cell activation. Indeed, it was found that MSCs do not affect the initial T cell response when present during their anti-CD3-induced activation, as demonstrated by normal increases in CD69 expression. As further evidence that IFNγ released from splenocytes after initial activation was key to inducing immunosuppression by MSCs, it was observed that MSCs derived from mice deficient in IFNγ receptor 1 (IFNγ R1−/−) were incapable of immunosuppression. Several clones of these IFNγ R1−/− MSCs were derived (all capable of differentiation into adipocytes and osteoblast-like cells), and none of the five clones tested were able to suppress anti-CD3-induced splenocyte proliferation, supporting the understanding that IFNγ is essential in the induction of the immunosuppressive function of MSCs.

These results indicate that the initial production of IFNγ and other cytokines by cells in close proximity to MSCs are critical to induce the immunosuppressive capacity. Indeed, anti-IFNγ (20 µg/ml) also completely blocked the suppressive effect of MSCs in this setting. In addition, although antibodies against TNFα, IL-1α, and IL-1β (20 µg/ml each) were ineffective individually, immunosuppression was prevented when all three antibodies were added together, similar to their effect when added to activated splenocyte supernatant. Therefore, the concomitant action of locally produced IFNγ along with TNFα, IL-1α, and IL-1β is sufficient to induce MSCs to become immunosuppressive.

Example 3

Immunosuppression by MSCs Requires Nitric Oxide

To identify the mechanism through which immunosuppression by cytokine-exposed MSCs is effected, the response of anti-CD3-activated splenocytes co-cultured with MSCs (1:20, MSC:splenocytes) in a TRANSWELL system was examined in various configurations. When separated by a permeable membrane (0.4 µm pore membrane) in the two chambers of the well, MSCs had almost no effect on T cell proliferation, indicating that a cell membrane-associated protein or other local acting factor(s) was critical for the suppression of T cell proliferation by cytokine-primed MSCs. While a recent report (Sato, et al. (2007) supra) showed that PGE-2, but not IDO, is required, it was found that PGE-2 was not involved. In fact, no effect was found on immunosuppression by MSCs by indomethacin (10 µM, a PGE-2 blocker), anti-IL-10 (20 µg/ml), anti-TGFβ (20 µg/ml) or 1-methyl-DL-tryptophan (1-MT, 1 mM, an IDO inhibitor), thereby ruling out these factors.

Nitric oxide (NO) at high concentrations is known to inhibit T cell responses. It diffuses quickly from its source, but the concentration of the active form drops off within about 100 µm. Therefore, NO can act only in close proximity to the cells producing it, which is consistent with the predicted characteristics of the factor that mediates immunosuppression by MSCs. To determine whether NO had such a role, its production was shut down using a selective inhibitor of iNOS activity, N G-monomethyl-L-arginin (L-NMMA). When added to mixed co-cultures of MSCs and splenocytes in the presence of anti-CD3, L-NMMA completely restored normal splenocyte proliferation. Other iNOS inhibitors such as 1400 W and L-NAME showed the same effect. Furthermore, MSCs derived from mice deficient in iNOS (iNOS−/−) had almost no effect on splenocyte proliferation. In addition, of five clones of iNOS−/− MSCs derived (all capable of differentiation into adipocytes and osteoblast-like cells), none were immunosuppressive. These results indicate that the activity of NO produced by MSCs in response to cytokine-induction mediates their suppression of T cell responses.

The analysis herein indicates that immunosuppression by MSCs is induced by IFNγ and proinflammatory cytokines and is mediated through NO. Accordingly, it was contemplated that MSCs could upregulate their expression of iNOS and produce NO after exposure to these cytokines. To examine this, MSCs were treated with activated splenocyte supernatant and the level of iNOS mRNA assayed by real-time PCR and compared to β-actin. The results of this analysis indicated that iNOS was significantly upregulated in MSCs by 4 hours after stimulation, with high-level expression sustained for at least 48 hours. At 12 hours post-stimulation, the level of iNOS mRNA was more than 7 times greater than β actin message, indicative of extremely high expression. A similar effect was observed when IFNγ and TNFα (20 ng/ml each) were added together, while either alone was ineffective.

In addition, IL-1α and IL-1β were again interchangeable with TNFα in this regard. When antibodies were added to neutralize cytokine activities in anti-CD3-activated splenocyte supernatant, it was observed that anti-IFNγ alone, or the 3-antibody combination against TNFα, IL-1α, and IL-1β, prevented iNOS upregulation by MSCs. When antibodies against TNFα, IL-1α or IL-1β were used singly or doubly, there was no effect. Therefore, the same cytokines that induce immunosuppression are also potent inducers of iNOS expression by MSCs.

To determine whether iNOS expression in cytokine-treated MSCs indeed leads to NO production, two stable breakdown products of NO, nitrate (NO3) and nitrite (NO2), were measured in conditioned medium from MSCs treated with anti-CD3-activated splenocyte supernatant. The amount of NO2 produced by MSCs after treatment was at least 10 times greater than that from similarly treated $CD11b^+F4/80^+$ macrophages, which are known to be abundant producers of NO. These results are consistent with the high levels of iNOS mRNA expression described herein. Thus, upregulation of iNOS expression by MSCs in response to proinflammatory cytokines leads to production of NO, which can act on T cells in close proximity.

In the present study, with T cell activation or when exogenous inflammatory cytokines are added, the T cells first enter cell cycle arrest and then die within 24 hours. It was also observed that this apoptosis was dependent on NO, since T cell apoptosis was not observed when iNOS inhibitors were used. Apoptosis was also absent when $iNOS^{-/-}$ or $IFN\gamma\ R1^{-/-}$ MSCs were used. Therefore, NO-induced cell cycle arrest and apoptosis of T cells are part of the mechanism of immunosuppression mediated by inflammatory cytokine-activated MSCs. Differences between species in inflammatory cytokine-induced expression of iNOS has been noted in macrophages (Schneemann & Schoedon. 2002) Nat. Immunol. 3(2):102). NO was found to be induced by inflammatory cytokines in macrophages of mouse, rat, and bovine origin, but not caprine, lapin, porcine, and human macrophages (Schneemann & Schoedon (2002) supra; Jungi, et al. (1996) Vet. Immunol. Immunopathol. 54:323-330). Thus, the roles of IDO and NO in the inhibition of T cell proliferation by MSCs from mouse and human were analyzed in a side-by-side comparison. It was found that inhibition of NO by L-NMMA completely reversed immunosuppression by mouse MSCs, whereas the inhibition of peripheral blood mononuclear cell proliferation by human MSCs was reversed by 1-MT, indicating that MSCs from humans utilize IDO as the major effector of immunosuppression, in comparison to mouse MSCs which utilize NO (Ren G, Su J, Zhang L, Zhao X, Ling W, L'huillie A, Zhang J, Lu Y, Roberts A I, Ji W, Rabson A B, Shi Y. Species variation in the mechanisms of mesenchymal stem cell-mediated immunosuppression. *Stem Cells* 2009, 27:1954-1962).

Example 4

Chemoattractive Property of MSCs is Induced by Proinflammatory Cytokines

In several studies, effective immunosuppression by MSCs in vivo has been achieved with as few as one to five MSCs per million somatic cells and often endures for months, with complete cure of immune disorders in some instances. Considering that MSCs are immobile after settling in tissues, and that immunosuppression is mediated by NO, which acts only very locally near its source, this immunosuppressive effect is astonishing. It was contemplated that cytokine-induced MSCs might have a mechanism to attract immune cells to their vicinity, where the locally high concentrations of NO could act effectively on the target T cells. To explore this, co-cultures of MSCs and splenocytes were monitored over time under the microscope.

Upon anti-CD3-stimulation, the splenocytes were observed to actively migrate toward the spindle-shaped MSCs. In contrast, no migration occurred in the absence of anti-CD3 stimulation. Since splenocytes have limited viability, the lack of locomotion toward MSCs in the absence of stimulation might be due to the poor health of these cells in vitro. To exclude this, activated-splenocyte-supernatant-primed MSCs were examined for their ability to attract A1.1 T hybridoma cells, which survive well even in the absence of IL-2. Under these conditions, time-lapse microvideography revealed brisk migration of T cells toward MSCs within 1.5 hours of co-culture initiation. Without priming of MSCs, however, there was no net movement of T cells toward the MSCs. Therefore, MSCs promote the migration of T cells only after MSCs having been exposed to proinflammatory cytokines.

To examine the role of various cytokines in enabling MSCs to attract T cells, MSCs were pretreated with various combinations of recombinant cytokines and the resultant migration of pre-activated T cells in co-cultures was observed. This analysis indicated that the same T cell cytokine pairs (i.e., IFN$\gamma$ and TNF$\alpha$; IFN$\gamma$ and IL-1$\alpha$ or IFN$\gamma$ and IL-1$\beta$) that had induced the immunosuppressive function of MSCs also caused them to attract T cells. Likewise, using antibody neutralization of specific cytokines, it was found that migration toward MSCs was prevented by anti-IFN$\gamma$ alone, or by blocking TNF$\alpha$, IL-1$\alpha$ and IL-1$\beta$ as a threesome, identical to their effects on activated-splenocyte-supernatant-induced MSC suppression of T cell proliferation. Therefore, the cytokine-induced immunosuppressive function of MSCs is likely to depend on the migration of lymphocytes into proximity with MSCs, where NO levels are highest.

Example 5

Proinflammatory Cytokines Induce MSCs to Produce Chemokines that are Critical for Immunosuppression The robust migration of activated T cells toward cytokine-primed MSCs indicated that the MSCs secrete potent chemoattractants, such as chemokines. Accordingly, the production of leukocyte chemokines by MSCs cultured under various conditions was determined by assaying the supernatant. No significant chemokine production was observed for MSCs cultured alone without cytokines, corroborating the findings that MSCs in their innate form are unable to attract T cells. When co-cultured with anti-CD3-activated splenocytes, however, MSCs produced several chemokines in large amounts, including CXCL-9 (MIG) at 1.5 ng/ml (12 ng/ml in another experiment) and CXCL-10 (IP-10) at 50 ng/ml at a MSC: splenocyte ratio of 1:60. These are potent T cell-specific chemokines; it has been shown that concentrations of only 1 to 10 ng/ml of either chemokine alone drive significant chemotaxis in vitro (Loetscher, et al. (1998) Eur. J. Immunol. 28:3696-3705; Meyer, et al. (2001) Eur. J. Immunol. 31:2521-2527). The production of CXCL-9 and CXCL-10 was inhibited by antibody neutralization of IFN$\gamma$ alone, or all three cytokines TNF$\alpha$; IL-1.$\alpha$, and IL-1$\beta$, similar to the effects on immunosuppression induction. Chemokine production was similarly induced by adding recombinant IFN$\gamma$ and TNF$\alpha$ (20 ng/ml each) to MSCs alone, with TNF$\alpha$ again being interchangeable with IL-1$\alpha$ and IL-1$\beta$. Therefore, these cytokines are sufficient to induce MSC expression of chemokines, which are likely to be responsible for driving T cell chemotaxis toward MSCs. Thus, once they have migrated into close proximity with MSCs, activated T cells would be expected to secrete cytokines that induce the production of additional chemokines by the MSCs, thus creating a positive feedback loop to attract still more T cells to the vicinity of MSCs.

To systematically examine the chemokine expression profile of MSCs, the expression of 84 different genes encoding chemokines and their receptors was examined in MSCs treated with supernatant from naive or anti-CD3-activated splenocytes. Total RNA was analyzed by real-time PCR using the Mouse Chemokines and Receptors RT2 PRO-FILER™ PCR Array kit, and chemokine mRNA levels compared to that of β actin (Table 1). The some human cytokine combination also induced similar chemkine in human MSCs. production

TABLE 1

Induction of Expression of Chemokines and Related Genes in MSCs Treated with Supernatant from activated T cells (β-actin defined as $1 \times 10^7$ units)

| Gene Symbol | Description | Naive Spin Sup | Activated Spin Sup | Fold Increase |
|---|---|---|---|---|
| Cxcl9 | Chemokine (C-X-C motif) ligand 9, MIG | 4 | 8,963,294 | 2,025,082 |
| Cxcl5 | Chemokine (C-X-C motif) ligand 5, ENA-78 | 2 | 4,302,867 | 1,978,890 |
| Cxcl2 | Chemokine (C-X-C motif) ligand 2, Groβ | 2 | 2,711,838 | 1,681,250 |
| Ccl7 | Chemokine (C-C motif) ligand 7. MCP-3 | 0 | 24,269 | 1,111,786 |
| Cxcl10 | Chemokine (C-X-C motif) ligand 10, IP-10 | 111 | 19,719,159 | 177,864 |
| Cxcl1 | Chemokine (C-X-C motif) ligand 1, Gro α | 47 | 5,170,437 | 110,278 |
| Ccl5 | Chemokine (C-C motif) ligand 5, RANTES | 215 | 8,022,162 | 37,344 |
| Ccl2 | Chemokine (C-C motif) ligand 2, MCP-1 | 3,252 | 11,653,869 | 3,584 |
| Cxcl11 | Chemokine (C-X-C motif) ligand 11, ITAC | 5 | 17,370 | 3,534 |
| Ccrl2 | Chemokine (C-C motif) receptor-like 2 | 110 | 56,765 | 518 |
| Ccl17 | Chemokine (C-C motif) ligand 17, TARC | 294 | 23,212 | 79 |
| Cx3cl1 | Chemokine (C-X3-C motif) ligand 1, fractalkine | 69,309 | 2,349,699 | 34 |
| Cmkor1 | Chemokine orphan receptor 1 | 32,965 | 617,300 | 19 |
| Ccl8 | Chemokine (C-C motif) ligand 8, MCP-2 | 628 | 10,070 | 16 |
| Ccl9 | Chemokine (C-C motif) ligand 9 | 182 | 2,193 | 12 |
| Ccr9 | Chemokine (C-C motif) receptor 9 | 999 | 3,860 | 4 |
| Cxcl13 | Chemokine (C-X-C motif) ligand 13, BCA-1 | 19,067 | 48,073 | 3 |
| Cxcr6 | Chemokine (C-X-C motif) receptor 6 | 4,943 | 7,516 | 2 |
| Cmklr1 | Chemokine-like receptor 1 | 49,839 | 47,340 | 1 |
| Ccbp2 | Chemokine binding protein 2 | 0 | 9,015 | N/A |
| Actb | β-actin | 10,000,000 | 10,000,000 | 1 |

MSCs ($1 \times 10^6$/T-25 flask in 5 ml of complete medium) was stimulated with supernatant from naive or activated T cells (50% of the final volume) for 12 hr. Chemokine and chemokine receptor gene expression were assayed by real-time PCR.

It was found that, except for low levels of CX3CL-1 (fractalkine) and CXCL13 (Chemokine (C-X-C) ligand 13, BCA-1), mRNA levels in MSCs exposed to naive splenocyte supernatant were insignificant. Strikingly, treatment of MSCs with activated splenocyte supernatant resulted in a more than one million-fold increase in some chemokines, such as CXCL2 (Chemokine (C-X-C) ligand 2, Groβ), CXCL5 (Chemokine (C-C) ligand 5, RANTES), CXCL9 (Chemokine (C-X-C) ligand 9, MIG), CXCL10 (Chemokine (C-X-C) ligand 10, IP-10) and CCL7 (Chemokine (C-C) ligand 7, MCP-3). In absolute terms, some chemokines reached the same level of expression as β-actin, or even higher. For example, CXCL10 showed twice the mRNA copy number as β-actin. The chemokines that were most highly induced are extremely potent inducers of leukocyte chemotaxis and are likely to play an important role in immunosuppression by MSCs. In fact, it was observed that antibody blockade of CXCR3, a receptor for the T cell chemokines CXCL9, CXCL10 and CXCL11 (Lazzeri & Romagnani, (2005) Curr. Drug Targets Immune Endocr. Metabol. Disord. 5:109-118), which were all highly induced in MSCs, inhibited the chemotaxis of T cell blasts toward MSCs and reverted the suppression of their proliferation.

To directly examine the chemotaxis-driving capacity of proinflammatory cytokine-induced MSC supernatant, the CHEMOTX Chemotaxis System (NeuroProbe) was employed. This system is composed of upper and lower chambers separated by a polyvinylpyrrolidine-free polycarbonate membrane (5 μm pore size). Supernatant from MSC cultures was placed in the lower chambers and activated CD4+ or CD8+ T cell blasts were added to the upper chambers in the presence of IL-2. Chemotaxis was quantified after 3 hours. It was found that dramatic chemotaxis by both CD4+ and CD8+ T cells occurred in response to culture supernatant from MSCs treated with IFNγ plus TNFα or with IFNγ plus IL-1. Similar results were obtained with supernatant from MSCs treated with medium conditioned by activated splenocytes.

In contrast, negative control supernatants from untreated MSCs or activated splenocytes alone were non-chemotactic, as was the direct addition of IFNγ plus TNFα without MSCs. Importantly; this chemotactic activity could be blocked by antibodies against CXCR3 and CCR5, two of the most important T cell-specific chemokine receptors, especially when both antibodies were added together. In addition to recruiting T cells, cytokine-activated MSCs also attracted bone marrow-derived dendritic cells, macrophages, and B cells.

The CHEMOTX system was also used to examine the role of chemotaxis in the inhibition of T cell proliferation. In this assay, MSCs were added to the lower wells, with or without addition of IFNγ plus TNFα, and T cell blasts (with IL-2) were added to the upper wells. In this set-up, chemokines produced by MSCs in the lower wells should induce T cell migration through the membrane and into the lower wells, where NO produced by MSCs could thus inhibit their proliferation. After a 3-hour incubation, both the upper and lower wells were pulsed with 3H-thymidine for an additional 6 hours and cells in both wells harvested for determination of proliferation. Proliferation levels of both CD4+ and CD8+ T cell blasts were significantly inhibited by MSCs in the presence of IFNγ and TNFα. Again, blocking antibodies against the T cell chemokine receptors, CXCR3 and CCR5, significantly reversed this effect. These data further indicate that T cell chemotaxis is critical in MSC-mediated immunosuppression.

Taken together, these results indicate that when MSCs are exposed to pro-inflammatory cytokines during an immune reaction, they produce large amounts of several chemokines, especially those specific for T cells, which thus attract T cells into close proximity to MSCs, where high concentrations of NO act to suppress T cell function.

Example 6

Figure 2:
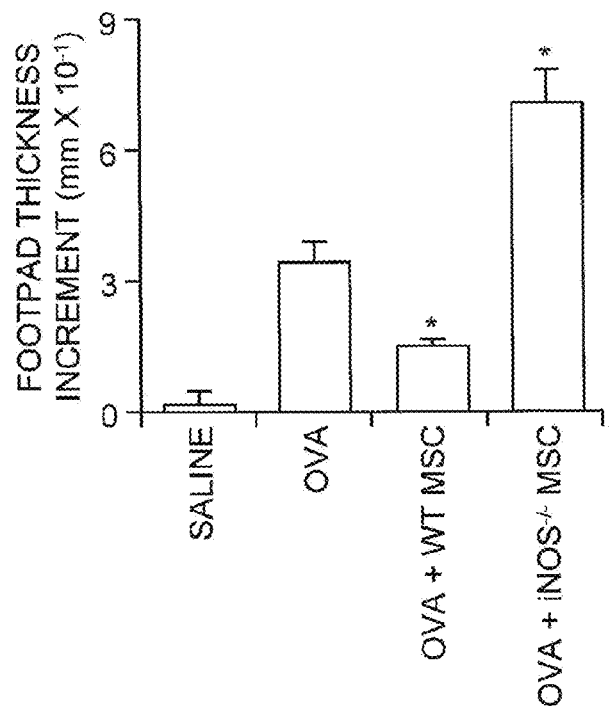
FIG. 2. is a graph showing that iNOS-Deficient MSCs Boost DTH. C57BL/6 mice were immunized with OVA in complete Freund's adjuvant by tail base injection. Mice were challenged in the footpad with 200 μg aggregated OVA administered with or without wild-type or iNOS$^{-/-}$ MSCs ($2.5 \times 10^5$ cells) on day 7. Footpad thickness increment was determined after 24 hours as a measure of DTH. Data shown are means±SD of a representative of three experiments. * p<0.005 vs. OVA alone.

Prevention of Delayed-Type Hypersensitivity (DTH) and Graft-Versus-Host Disease (GvHD) by MSCs is Dependent on Inflammatory Cytokines and NO Production Mice were injected in the footpad with OVA alone or OVA and MSCs from iNOS-deficient or wild-type mice. The mice were then challenged in the footpad with OVA and the resultant DTH response measured by footpad swelling. The results of this analysis indicated that administration of wild-type MSCs resulted in reduced inflammation in the DTH response. In sharp contrast, iNOS-deficient MSCs not only did not reduce inflammation, but also actually enhanced the DTH response in comparison to challenged mice not injected with MSCs (FIG. 2). Histological analysis of the footpads showed reduced indicators of inflammation in skin from animals co-injected with wild-type MSCs, while those co-injected with iNOS$^{-/-}$MSCs had increased fluid and leukocyte infiltration at the site of inflammation. This experiment not only demonstrates the requirement for NO in the suppression of an immune response, but also shows that, in the absence of NO production, MSC-mediated chemotaxis enhances inflammation, and could be used to boost local immune responses such as to promote the efficacy of vaccines or provoke effective immune responses to tumors using inhibitors to iNOS and IDO.

One of the striking effects of immunosuppression by MSCs is the ability to suppress graft-versus-host disease (GvHD) (Le Blanc, et al. (2004) supra; Le Blanc & Ringden (2006) supra). To investigate whether cytokine-induced NO production by MSC results in immunosuppression in vivo, $5\times10^6$ nucleated bone marrow cells and $5\times10^6$ splenocytes from C57BL/6 mice were injected into lethally irradiated F1 (C57BL/6×C3H) mice to established the mouse GvHD model. All recipient positive-control mice developed extensive GvHD (wasting, ruffled hair, and hunched back) between days 15 and 22, while the negative controls that received syngeneic F1 bone marrow were unaffected.

Figure 3:
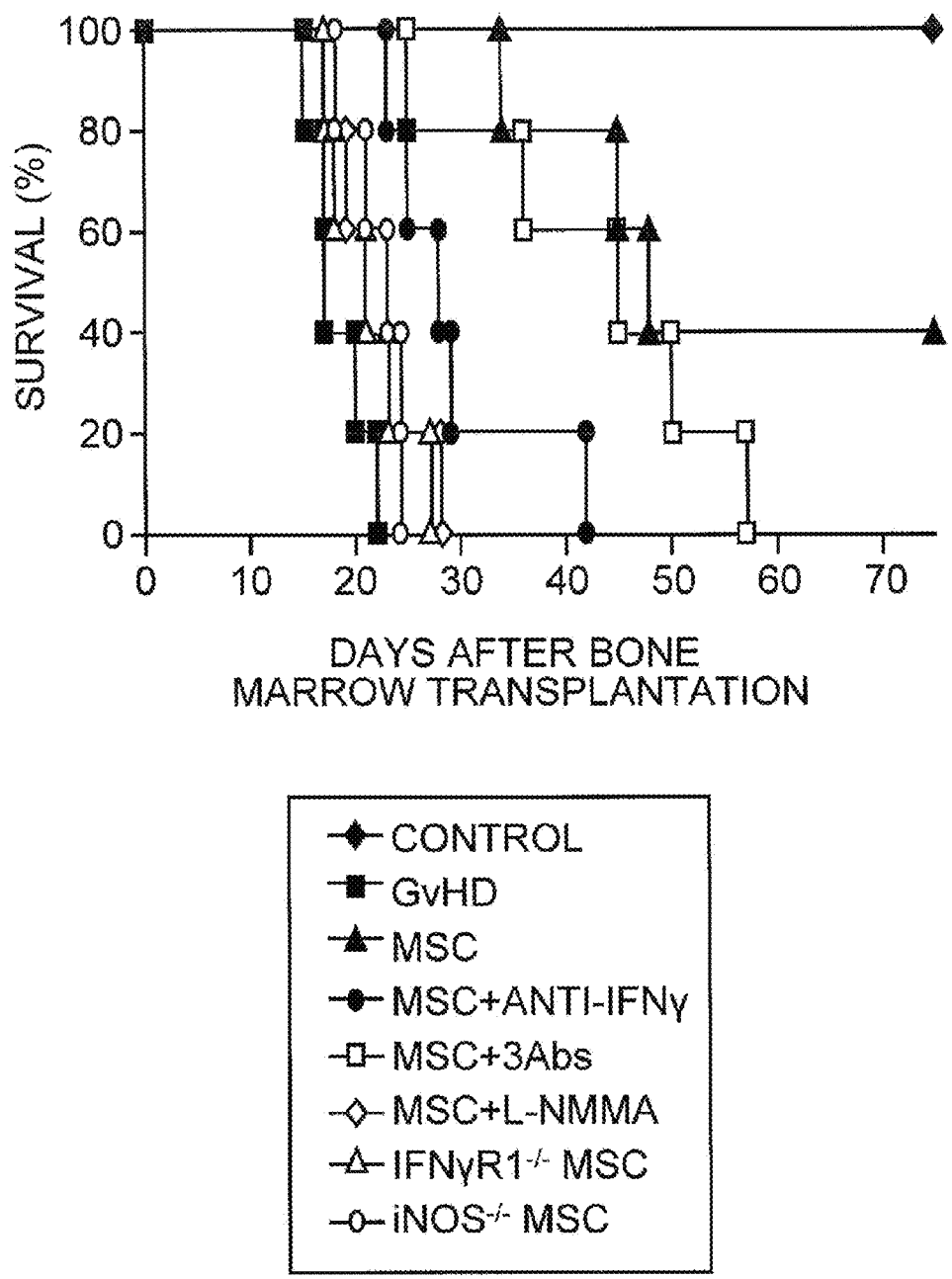
FIG. 3. is a graph showing that MSCs Prevent GvHD in a Manner Dependent on Inflammatory Cytokines and NO. Recipient mice (C57BL/6xC3H, F1) were lethally irradiated and injected i.v. with C57BL/6 bone marrow cells plus spleenocytes. On days 3 and 7 after bone marrow transplantation, recipients were administered with the indicated MSCs. For some wild-type MSC groups, L-NMMA, anti-IFNγ or a 3-antibody cocktail against TNFα, IL-1α, and IL-1β, (3 Abs) were injected i.p. Survival was monitored daily for 12 weeks.

When F1 mice were treated with MSCs ($0.5\times10^6$ cells derived from donor mice injected i.v. on days 3 and 7) after bone marrow transplantation, there was significant protection from GvHD; all MSC-treated mice survived for at least 33 days and some for more than 75 days. In contrast, F1 mice treated with MSCs derived from iNOS$^{-/-}$ or IFN$\gamma$ R1$^{-/-}$ mice were not protected, as their survival was not different from untreated positive controls (FIG. 3). This lack of protection by MSCs deficient in IFN$\gamma$ R1 or iNOS indicates that IFN$\gamma$ and NO production are essential for MSC-mediated immunosuppression in vivo.

Since in vitro results indicated that IFN$\gamma$ acts together with either one of the three cytokines, TNF$\alpha$, IL-1$\alpha$, or IL-1$\beta$ to induce the immunosuppressive function of MSCs, the role of these cytokines was examined in MSC-mediated protection from GvHD. Mice were injected with neutralizing antibodies against these cytokines or L-NMMA for 7 days after wild-type MSC infusion, and GvHD was allowed to develop. Both anti-IFN$\gamma$ and L-NMMA caused significant reversal of MSC-mediated protection from GvHD (FIG. 3), while negative control mice showed no adverse effect in response to these treatments.

Figure 4:
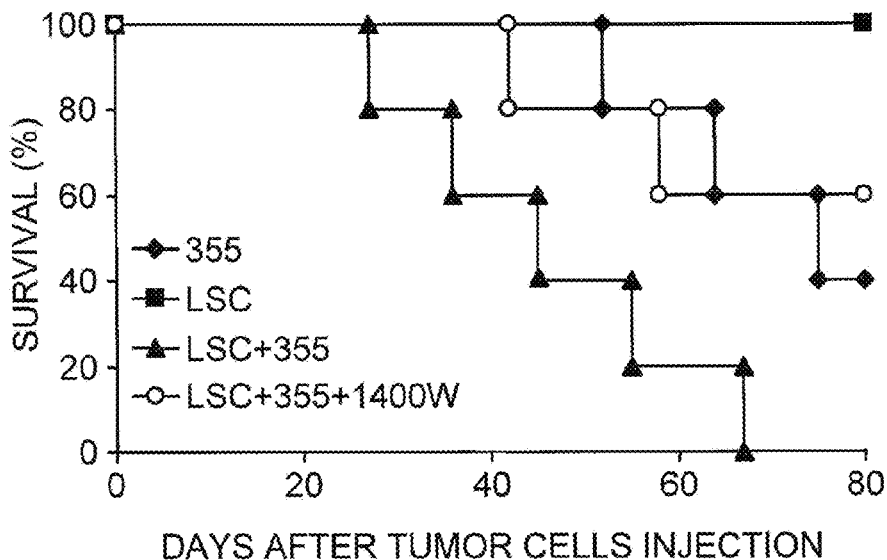
FIG. 4. is a graph showing that lymphoma stromal cells (LSCs) promote lymphoma development in a NO-dependent manner. 355 B-cell lymphoma cell line (C3H-gld/gld background, $0.5 \times 10^6$ cells/mouse) was co-injected with gld/gld mice-derived lymphoma stromal cells (C3H background, P5, $0.25 \times 10^6$ cells/mouse) by tail-vein i.v. on day 0.1400 W (NOS inhibitor, 0.1 mg/mouse) was injected on day 0, 2, 4, 8, 12, 16, 20, 24, and 28 by i.p. Mice survival was recorded when mice were moribund.

The effect of a 3-antibody cocktail against TNF$\alpha$, IL-1$\alpha$, and IL-1$\beta$ was less dramatic, not reaching statistical significance (FIG. 4). This result further implicates IFN$\gamma$ and NO production, but is equivocal for the other cytokines. It is important to recognize, however, that besides synergizing with IFN$\gamma$ to induce immunosuppression by MSCs, TNF$\alpha$ and IL-1 are also important factors in the normal pathogenesis of GvHD. In fact, it has been reported that neutralization of either TNF$\alpha$ or IL-1 can lessen the severity of GvHD (Hattori, et al. (1998) Blood 91:4051-4055; Mccarthy, et al. (1991) Blood 78:1915-1918). Therefore, it was somewhat expected that protection from GvHD was not reversed to a greater extent by these antibodies.

Histological examination of the severity of inflammation in various organs from these mice was also examined 14 days after bone marrow transplantation. The extent of observed leukocyte infiltration correlated well with the survival results; GvHD-induced mice showed increased numbers of lymphocytes in the liver, lungs, and skin, while they were nearly absent in those treated with MSCs. In addition, protection by MSC was almost completely reversed by anti-IFN$\gamma$ and L-NMMA, while the 3-antibody cocktail against TNF$\alpha$, IL-1$\alpha$ and IL-11 were less effective. Together, the findings from these GvHD experiments, as well as those from the DTH studies, clearly indicate a role for IFN$\gamma$ and NO in MSC-mediated immunosuppression in vivo.

Example 7

Tumor-Derived MSC-Like Lymphoma Stromal Cells are Immunosuppressive

Since the tumor cells in lymphoma are not adherent, it is possible to isolate tumor stromal cells from lymphomas developed in p53+/− mice. It was observed that these cells can be passaged in vitro and can be differentiated into adipocytes and osteoblast-like cells. Interestingly, like bone marrow derived MSCs, these tumor stromal cells are also immunosuppressive and can effectively inhibit the proliferation of ant-CD3-activated splenocytes. This immunosuppressive effect was also dependent on IFN$\gamma$+TNF $\alpha$ and NO, since anti-IFN$\gamma$ IFN$\gamma$ and iNOS inhibitors could reverse the immunosuppressive effect.

Example 8

Lymphoma Stromal Cells (LSCs) Promote Lymphoma Development in a NO-Dependent Manner To examine the effect of lymphoma stromal cells on tumor growth, 355 B-cell lymphoma cell line (C3H-gld/gld background, $0.5\times10^6$ cells/mouse) was co-injected with gld/gld mice-derived lymphoma stromal cells (C3H background, P5, $0.25\times10^6$ cells/mouse). It was observed that co-injection of stromal cells significantly enhanced the mortality. Interestingly, administration of 1400 W (NOS inhibitor, 0.1 mg/mouse on day 0, 2, 4, 8, 12, 16, 20, 24, and 28) significantly reverted the effect (FIG. 4). Therefore, the tumor stromal cells could significantly promote tumor growth.

Example 9

Combination of NOS Inhibitor with IFN$\gamma$ Promotes Mouse Melanoma Therapy

Figure 5:
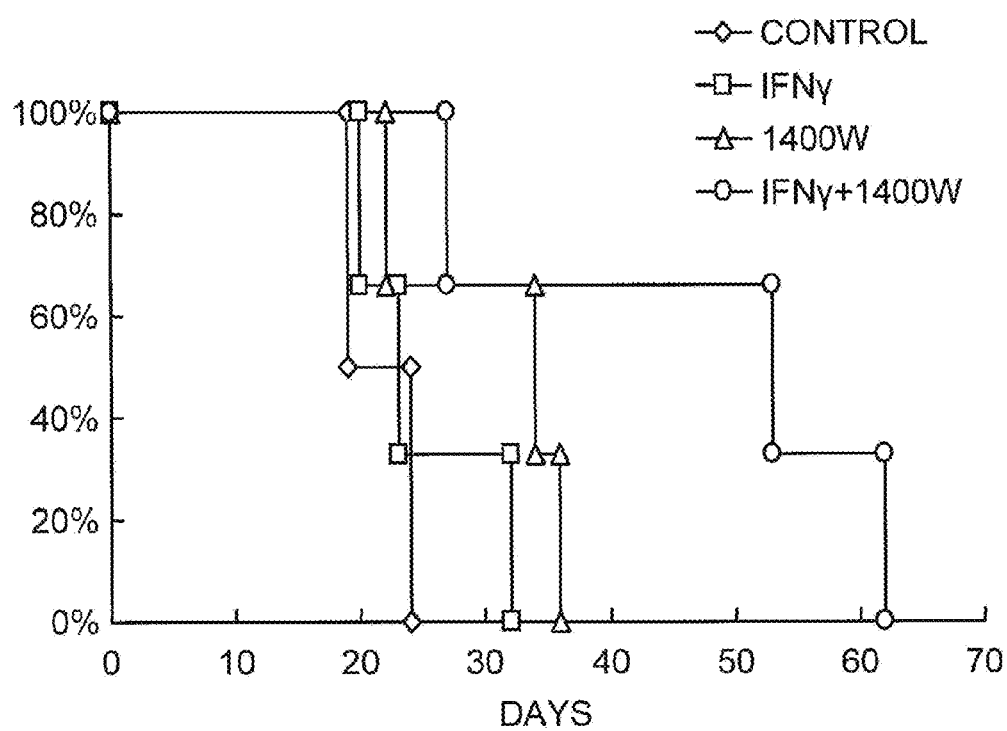
FIG. 5. is a graph showing that the combination of NOS inhibitor with IFNγ promotes mouse melanoma therapy. B16-F0 melanoma cells were injected into C57BL/6 mice on day 0 by i.v. (0.5×10 6 cells/mouse). IFNγ (250 ng/mouse) and 1400 W (NOS inhibitor, 0.1 mg/mouse) were administrated by i.p. injection on day 4, 8, 12, 16, 20. Mice survival was recorded when mice were moribund.

To test the role of tumor stromal cell-produced NO on tumor immunotherapy, B16-F0 melanoma cells were injected into C57BL/6 mice on day 0 ($0.5\times10^6$ cells/mouse). IFN$\gamma$ (250 ng/mouse) or 1400 W (NOS inhibitor, 0.1 mg/mouse) were administrated by i.p. injection on day 4, 8, 12, 16, 20. Mice survival was recorded when mice were moribund. It was observed that the combined therapy dramatically promoted mouse survival (FIG. 5). Thus, IFN$\gamma$ has dual roles in tumor development; one is to prevent tumor development by producing some angiostatic factors or blocking some angiogenesis factor production, the other is to induce immunosuppression by tumor stromal or other environmental cells through producing factors like NO, IDO, or PGE2. Thus, inhibition of one or more of NO, IDO or PGE2 can dramatically enhance cancer treatment. Therefore, when immunotherapies such as those based on cytokines, vaccination, antibodies, dendritic cells, or T cells, are used to treat cancer, the tumor stromal cells might be responsible for the inability of these treatment to completely eradicate tumors in most cases. The combined used of inhibitors to iNOS and IDO with immunotherapies could provide effective ways to eradicate tumors.

Example 10

IL-17A Synergizes with IFN γ and TNFα to Induce a High Expression of the Immunosuppressive Effector Molecule iNOS in Mouse Bone Marrow Mesenchymal Stem Cells (BM-MSCs).

Mouse MSC-mediated immunosuppression is dependent on inflammatory cytokines. Without these cytokines, MSCs do not possess the immnosuppressive effect, unless in the presence of inflammatory cytokines IFN γ with TNFα or IL-1, MSCs are stimulated to express the immunosuppressive effector nitric oxide (NO), which is catalyzed by inducible NO synthase (iNOS), and several helper molecules-chemokines and adhesion molecules. Chemokines and adhesion molecules retain T-cells and other immune cells in the vicinity of MSCs, where high amount of NO suppress the function of the immune cells.

Since the in vivo inflammatory environment contains various kinds of inflammatory cytokines and growth factors in addition to the three types of cytokines that we mentioned before, the in situ functions of MSCs in the sites with tissue damage should be impacted by various cytokines in particular microenvironment niches, the present inventors examined other cytokines especially those express at high levels in autoimmune diseases and tissue injury.

Figure 6:
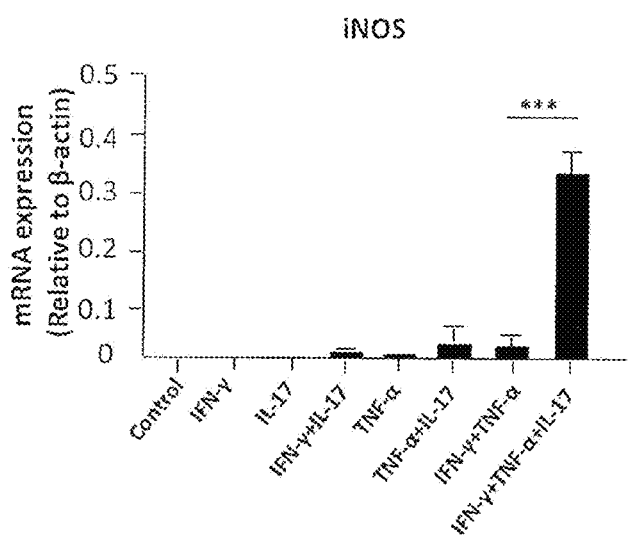
FIG. 6. IL-17A greatly enhances inflammatory cytokine-induced iNOS expression in mouse BM-MSCs at both mRNA and protein levels. BM-MSCs were treated with the indicated cytokines. The iNOS gene expression was measured by real-time PCR.

Among several cytokines tested, IL-17A was found to greatly enhance iNOS expression in the presence of IFNγ and TNFα. IL-17A is a critical proinflammatory cytokines found in many pathological conditions, however, little is known about how it influences the biology of MSCs. As shown in FIG. 6, at both mRNA and protein levels, IL-17A greatly enhanced the expression of iNOS. This finding indicated that further supplement of IL-17A could be a potential strategy to enhance the immunosuppressive activity of MSCs.

Example 11

IL-17A Enhances BM-MSC-Mediated Immunosuppression on T-Cell Proliferation.

Figure 7:
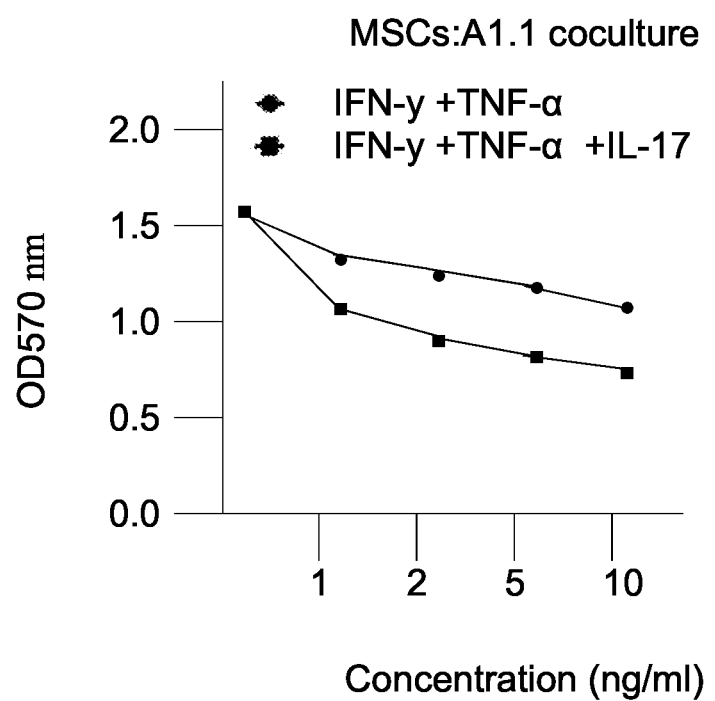
FIG. 7. IL-17A significantly promoted MSC-mediated immunosuppressive effect. MSC cells and T-cell hybridoma A1.1 cell line were co-cultured at a ratio of 1:20. The co-cultures were supplemented with IFNγ+ TNF α, or IL-17A+IFNγ+TNFα. Cell proliferation was measured by the cell density indicated by O.D. 570 nm.
Figure 8A:
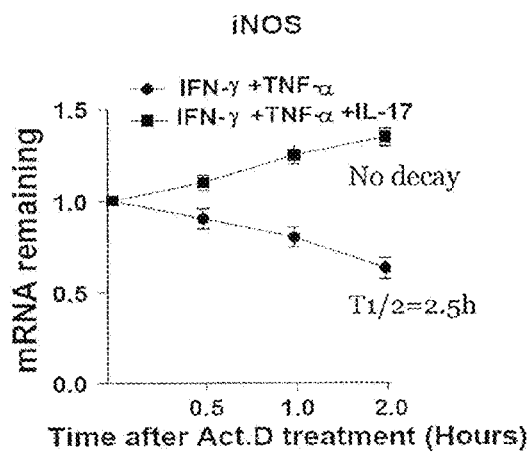
FIGS. 8A and 8B. IL-17A prevented the decay of iNOS mRNA, (FIG. 8A) the iNOS mRNA stability was measured at different time points after actinomycin D treatment in IFNγ+TNFα and IFNγ+TNFα+IL-17A treatment groups.
Figure 8B:
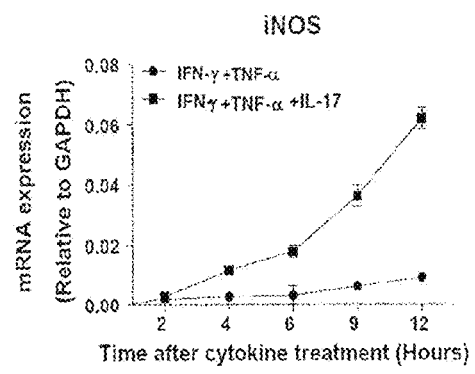

To test if the IL-17A enhanced iNOS expression is functional or not, a MSC-T cell co-culture system was performed to evaluate the immunosuppressive activity of MSCs. As shown in FIG. 7, supplementation with IFNγ and TNFα could decrease T-cell proliferation in a cytokine concentration dependent manner. Strikingly, addition of IL-17A enhanced the suppression of MSCs on T-cell proliferation. Therefore, IL-17A is functional in the enhancement of MSC-mediated immunosuppression.

Example 12

Materials and Methods

Reagents and Mice

Recombinant mouse IFNγ, TNFα, IL-17A, and antibodies against IL-17A were from eBiosciences (La Jolla, CA). Recombinant mouse IL-2 was from R&D Systems (Minneapolis, MN). Antibodies against β-actin, GAPDH, iNOS, p-IκBα, p-P65, p-JNK, and p-ERK1/2 were from Cell Signaling Technology (Danvers, MA). Antibody against Act1 was from Santa Cruz Biotechnology (Dallas, TX). PMSF and actinomycin D were purchased from Sigma-Aldrich (St. Louis, MO).

C57BL/6 mice were maintained under specific pathogen-free conditions in the vivarium with water and food provided ad libitum. All animal protocols are approved by our Institutional Animal Care and Use Committee.

Cells-MSCs were generated using the protocol as described in example 1. Briefly, tibia and femur bone marrow of 6-8 week old wild-type or auf1−/− mice was harvested. Cells were cultured in DMEM medium supplemented with 10% FBS, 2 mM glutamine, 100 U/ml penicillin, and 100 μg/ml streptomycin (complete medium, all from Invitrogen, Carlsbad, CA). All nonadherent cells were removed after 24 hours (hr), and adherent cells were maintained. Medium was changed every 2-3 days. To obtain MSC clones, cells at confluence were harvested and seeded into 96-well plates by limited dilution. Individual clones were then picked and expanded. MSCs were capable of differentiating into adipocytes and osteocytes under the respective differentiation conditions. Cells were used before the 15th passage.

T cell blasts were generated from naive splenocytes isolated from C57BL/6 mice, and cultured in RPMI-1640 medium supplemented with 10% heat-inactivated FBS, 2 mM glutamine, 100 U/ml penicillin, 100 μg/ml streptomycin, and 50 μM β-ME. Splenocytes ($1\times10^6$ cells/ml) were activated with anti-CD3 and anti-CD28 for 48 hr, and harvested, with supernatant filtered (0.1 μm) and frozen. The cells were then cultured with IL-2 (200 U/ml) alone for 48 hr.

Proliferation assay—To assay T cell proliferation, 0.5 μCi of 3H-thymidine was added to each well of 96-well plates 6 hr before termination of the cultures by freezing. Plates were then thawed, cells were harvested, and incorporated 3H-Tdr was assessed with a Wallac Microbeta scintillation counter (Perkin-Elmer, Waltham, MA).

Messenger RNA decay assays-Messenger RNA decay assays were performed essentially. MSCs were incubated with cytokine combinations for 6 hr. Actinomycin D (Act.D) was added into the medium at a final concentration of 5 μg/ml to stop transcription. At various time points after addition of Act.D, cells were harvested for extraction of total RNA.

Levels of iNOS, CXCL1, CCL2, CXCL10 and IL-6 mRNAs were measured at each time point by quantitative RT-PCR and normalized to levels of β-actin mRNA. Percentages of mRNA remaining for each time point were plotted versus time after Act.D addition. First order decay constants, k, were determined by nonlinear regression. The associated mRNA half-lives, t1/2, were calculated with the equation $t1/2=\ln2/k$.

RNA isolation and gene expression assay-Total RNA was isolated with the RNAprep Pure Cell/Bacteria Kit. First-strand cDNA synthesis was performed with a cDNA synthesis kit. The levels of mRNAs were measured by quantitative RT-PCR (7900 HT; Applied Biosystems, Foster City, CA) with SYBR Green Master Mix and normalized to the level of β-actin mRNA. Sequences of forward and reverse primer pairs are as follows:

iNOS, forward

5'-CAGCTGGGCTGTACAAACCTT-3' (SEQ ID NO: 1)
and reverse

5'-CATTGGAAGTGAAGCGTTTCG-3'; (SEQ ID NO: 2)

β-actin: forward

5'-CCACGAGCGGTTCCGATG-3' (SEQ ID NO: 3)
and reverse

5'-GCCACAGGATTCCATACCCA-3'; (SEQ ID NO: 4)

IL-6: forward

5'-GAGGATACCACTCCCAACAGACC-3' (SEQ ID NO: 5)
and reverse

5'-AAGTGCATCATCGTTGTTCATACA-3'; (SEQ ID NO: 6)

CXCL1: forward

5'-CTGCACCCAAACCGAAGTC-3' (SEQ ID NO: 7)
and reverse

5'-AGCTTCAGGGTCAAGGCAAG-3'; (SEQ ID NO: 8)

CCL2: forward

5'-TCTCTCTTCCTCCACCACCATG-3' (SEQ ID NO: 9)
and reverse

5'-GCGTTAACTGCATCTGGCTGA-3'; (SEQ ID NO: 10)

CCL5: forward

5'-TTTCTACACCAGCAGCAAGTGC-3' (SEQ ID NO: 11)
and reverse

5'-CCTTCGTGTGACAAACACGAC-3'; (SEQ ID NO: 12)

CXCL9: forward

5'-AGTGTGGAGTTCGAGGAACCCT-3' (SEQ ID NO: 13)
and reverse

5'-TGCAGGAGCATCGTGCATT-3'; (SEQ ID NO: 14)

CXCL10: forward

5'-TAGCTCAGGCTCGTCAGTTCT-3' (SEQ ID NO: 15)
and reverse

5'-GATGGTGGTTAAGTTCGTGCT-3'. (SEQ ID NO: 16)

Western blotting analysis-Cells were washed twice with ice-cold PBS, harvested and lysed in the RIPA buffer (Millipore, Temecular, CA) containing a cocktail of protease inhibitors (Roche, Natley, NJ) and PMSF (Sigma) for 30 min on ice. Lysates were clarified by centrifugation at 16,000 g for 15 minutes. Protein concentration of the supernatant was determined by the Bradford assay (Bio-Rad, Hercules, CA).

Protein samples were diluted in 5×SDS loading buffer (250 mM Tris-HCl, pH6.8, 10% SDS, 0.5% bromophenol blue, 50% glycerol, 5% β-mercaptoethanol) and fractionated in a 10% SDS-polyacrylamide gel. Proteins were electroblotted onto a nitrocellulose membrane (Whatman Inc., Clifton, NJ) and incubated for 1 hr in 5% nonfat dry milk dissolved in TBST (150 mM NaCl, 50 mM Tris-HCl, pH 7.5, 0.05% Tween 20) at room temperature. The blotting membranes were incubated with primary antibodies overnight at 4° C., extensively washed in TBST, incubated with HRP-conjugated secondary antibody (Cell Signaling) for 1.5 hr at room temperature, and washed again with TBST. The blotting membranes were developed with chemiluminescent reagents (Millipore, Billerica, MA) according to the instructions provide by the manufacturer.

Immunofluorescence detection of IL-17A receptor—Cultured MSCs were first washed with PBS and fixed with ice-cold methanol at −20° C. for 10 min. After a 10 min incubation with 0.3% Triton X-100 in PBS, cells were blocked with 5% BSA for 1 hr at room temperature and incubated with primary antibody anti-IL-17RA (Santa Cruz) overnight at 4° C. After washed by PBS, cells were incubated with Alexa Fluor 594 conjugated goat anti-rabbit secondary antibody and DAPI (Invitrogen) for 1 hr at room temperature. Cells were then washed with PBS before photographing.

ConA-induced liver injury in mice—C57BL/6 mice (8-10 week old) were intravenously injected with ConA (Vector Labs, Burlingame, CA) in PBS at 15 mg/kg to induce liver injury. MSCs (5×105) derived from wild-type mice or auf1−/− mice were treated with or without IFNγ, TNFα in the presence or absence of IL-17A (10 ng/ml for each cytokine) for 12 hr, and then intravenously administrated into mice that have been treated with ConA for 30 minutes. Mice were euthanized and serum and liver tissues were sampled after another 7.5 hr. Serum alanine aminotransferase (ALT) activity was determined by an ALT detection. Formalin-fixed liver histological sections were stained with hematoxilin & eosin (H&E).

Liver mononuclear cells isolation and flow cytometry analysis—Liver mononuclear cells (MNCs) were purified by a 40%/70% gradient and stained with anti-CD3-PE, anti-CD4-PerCP/Cy5.5, and anti-CD8a-APC (eBiosciences) for 30 min at 4° C. in staining buffer (PBS, 3% FCS). For detection of surface expression of IL-17RA in cloned MSCs, cells were stained with anti-IL-17RA-PE (eBiosciences) and analyzed by flow cytometry on a FACS Calibur flow cytometer (Becton Dickinson, San Jose, CA).

Statistical analysis-Nonlinear regression and statistical analyses were performed with PRISM v5 software (GraphPad Software, Inc.). Comparisons between samples were performed with the unpaired t test. Differences with $P<0.05$ were considered significant. (*, $P<0.05$; , $P<0.01$; *, $P<0.001$).

Results-IL-17A Enhances the Immunosuppressive Effect of MSCs

The instant example provides that the immunosuppressive function of MSCs is not innate but induced by proinflammatory cytokines in a concentration-dependent fashion. A combination of IFNγ and one of three other inflammatory cytokines-TNFα, IL-1α, or IL-1β—is required to enable the immunosuppressive effects of MSCs. IL-17A is a pleiotropic proinflammatory cytokine known for its critical roles in the pathogenesis of various inflammatory and autoimmune diseases. Interestingly, IL-17A is also known to synergize with certain cytokines to promote gene expression programs required for inflammation. Therefore, the present inventors examined whether IL-17A could synergize with suboptimal concentrations of IFNγ and TNFα to induce the immunosuppressive property of MSCs.

MSCs were cultured with various combinations of recombinant cytokines IFNγ, TNFα, and IL-17A at low concentrations (2 ng/ml each) for 12 hr; CD4+ T cell blasts were added to the cultures at a 1:20 ratio (MSC:T cells), together with IL-2, and T cell proliferation was assessed by 3H-thymidine incorporation (it is noted that T cell blasts proliferate in the presence of IL-2, but they do not produce cytokines without further TCR activation). It was then concluded that any of the three cytokines alone cannot induce immunosuppression in MSCs.

MSCs were first treated with the indicated combinations of recombinant cytokines IFNγ, TNFα, IL-17A (2 ng/ml each) for 12 hr, then cocultured with CD4+ T cell blasts at a 1:20 ratio (MSC:T cells), and proliferation was assessed by $^3$H-thymidine incorporation after an additional 12 hr. Accordingly, T cell proliferation is suppressed in the presence of IFNγ and TNFα, and this suppression can be markedly enhanced by IL-17A (FIG. 9 A), demonstrating a novel immunomodulatory function of IL-17A, a potent proinflammatory cytokine.

The mRNA expression of IL-17 receptor family members in MSCs or Raw 264.7 (Macrophages) were then examined by RT-PCR. NC: No RT. As such, IL-17A signals through IL-17RA and IL-17RC, expression of both receptors in MSCs was confirmed by RT-PCR (FIG. 9B), in which a mouse macrophage cell line Raw 264.7 was used as a positive control; cell surface expression of IL-17RA was also confirmed by indirect immunofluorescence microscopy and flow cytometry (FIG. 9C, upper and lower panels, respectively).

Figure 9D:
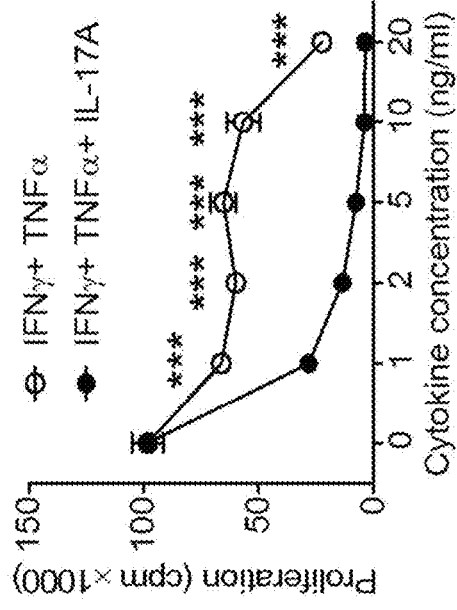
Figure 9E:
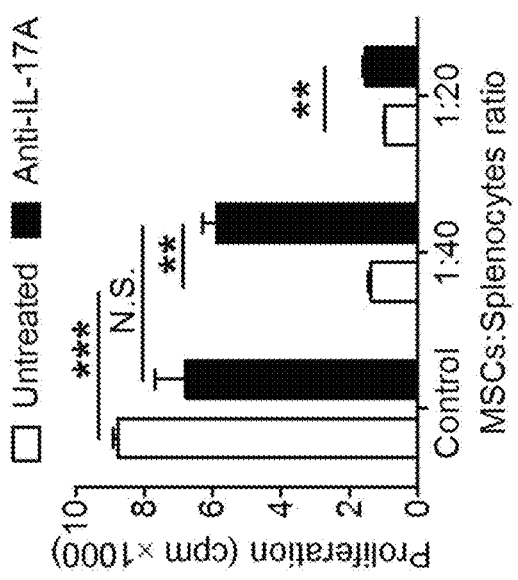
Figure 9F:
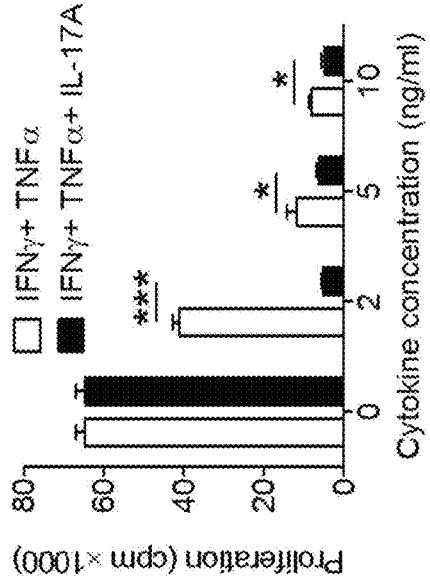

Since the concentrations of inflammatory cytokines vary at different stages of an inflammatory response, the concentration dependence of IFNγ and TNFα on IL-17A-enhanced immunosuppression was further assessed. MSCs were cultured with the indicated concentrations of IFNγ and TNFα, without or with 10 ng/ml IL-17A. MSCs were then cocultured with CD4+ T cell blasts or the A1.1 T cell hybridoma to assess the effects on T cell proliferation. IL-17A was able to enhance the immunosuppressive effect of MSCs on T cells at IFNγ and TNFα concentrations as low as 1-2 ng/ml each (FIG. 9D, 9E).

Even at higher concentrations of IFNγ and TNFα (i.e., 10-20 ng/ml), IL-17A still improved immunosuppression, though the effect was less pronounced. Nonetheless, MSCs were treated with IFNγ and TNFα (2 ng/ml) with graded concentrations of IL-17A, for 12 hr, and then cocultured with T cell hybridoma A1.1 cells at a ratio of 1:10 for 12 hr. Accordingly, the low concentrations of IFNγ and TNFα (2 ng/ml each), as little as 0.5 ng/ml IL-17A was sufficient to elicit a dramatic decrease in T cell proliferation (p<0.05; FIG. 9 F).

Figure 9G:
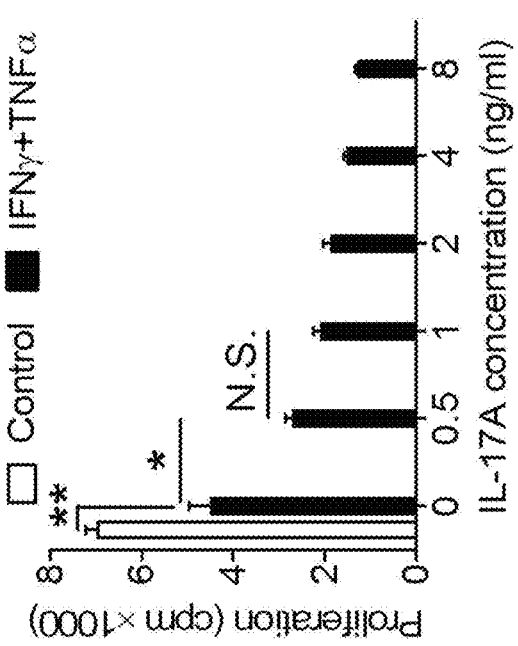

This observation provides MSCs can suppress proliferation of activated primary splenocytes depending on the inflammatory cytokines secreted by T cells. Activation of T cells lead to the production of many cytokines, including IL-17A. To confirm that IL-17A contributes to the immunosuppressive effect of MSCs, antibody against IL-17A was used to neutralize it in a MSC-activated splenocyte co-culture system. While proliferation of activated splenocytes was markedly inhibited by MSCs, this inhibition was partially reversed upon addition of antibody against IL-17A, i.e., proliferation increased in the presence of antibody (FIG. 9G). The optimal effect of antibody occurred with a MSC:splenocyte ratio of 1:40. With a MSC:splenocyte ratio of 1:20, the reversal was less pronounced, but still statistically significant (p<0.01). Taken together, these results indicated that IL-17A can enhance the immunosuppressive effects of MSCs, particularly when they are cultured in lower concentrations of IFNγ and TNFα.

IL-17A Synergizes with Inflammatory Cytokines to Induce the Expression of Immune Modulatory Genes in MSCs Nitric oxide (NO) and chemokines, acting in concert, are the key molecules mediating the immunosuppressive effects of MSCs. Chemokine and iNOS genes in MSCs are induced by IFNγ and TNFα. However, IL-17A enhanced immunosuppression by MSCs cultured with IFNγ and TNFα (FIG. 9 D, 9 E). This study was then designed to show that IL-17A synergizes with IFNγ and TNFα to induce the expression of iNOS and chemokines in MSCs. To test this hypothesis, a population of MSCs were cultured with various combinations of IFNγ, TNFα, and/or IL-17A, and the effects on expression of selected immune modulatory genes were assessed.

Compared with MSCs cultured with single or double combinations of cytokines, addition of IFNγ, TNFα, and IL-17A dramatically increased expression of iNOS, IL-6, and CXCL1 at the mRNA level (FIG. 10A); Western blot analysis confirmed an increase in iNOS protein levels as well (FIG. 10 B). However, the expression of other chemokines such as CCL5, CCL2, CXCL9, CXCL10, which play pivotal roles in the immunosuppressive effects of MSCs were all unaffected by addition of IL-17A (FIG. 10 C).

To confirm that the effects on gene expression were due to IL-17A, MSCs were cultured with supernatant from anti-CD3 and anti-CD28-activated splenocytes in the presence or absence of neutralizing antibody against IL-17A. Addition of anti-IL-17A to supernatants blocked induction of iNOS, IL-6, and CXCL1 gene expression without affecting CCL2, CCL5, CXCL9, or CXCL10 (FIG. 10D, 10E). Blocking signal transduction of IL-17A using Act1 knockdown MSCs further verified such conclusion.

Figure 11A:
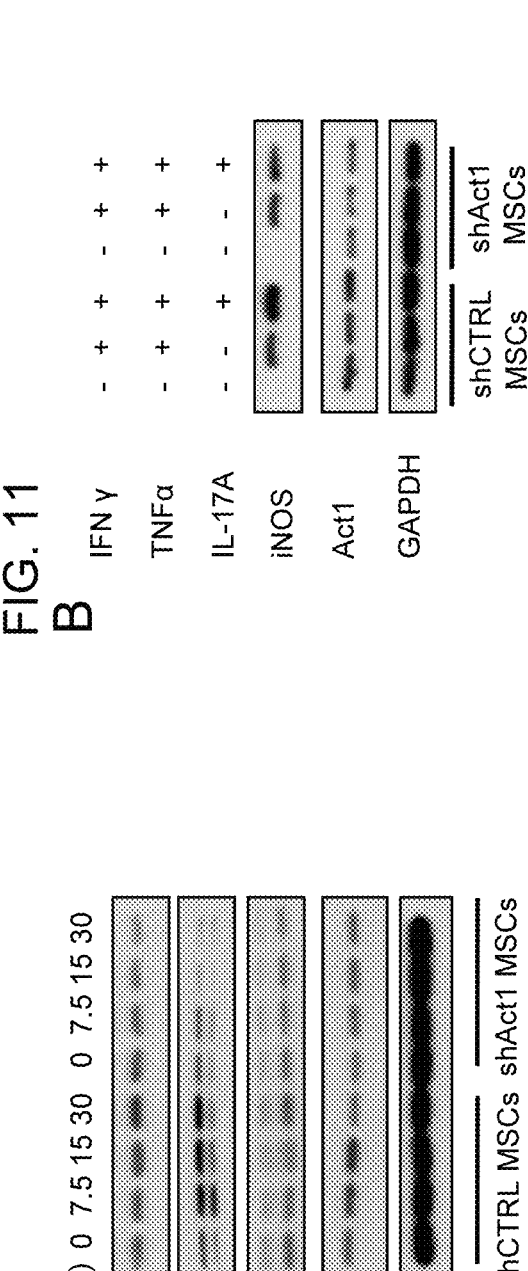
FIGS. 11A, 11B, 11C and 11D.
Figure 11B:
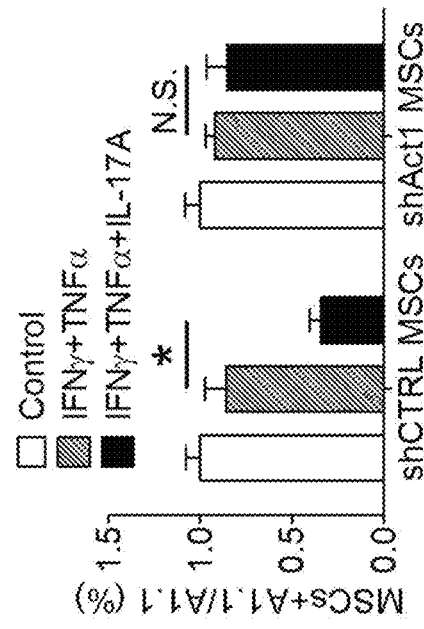
Figure 11C:
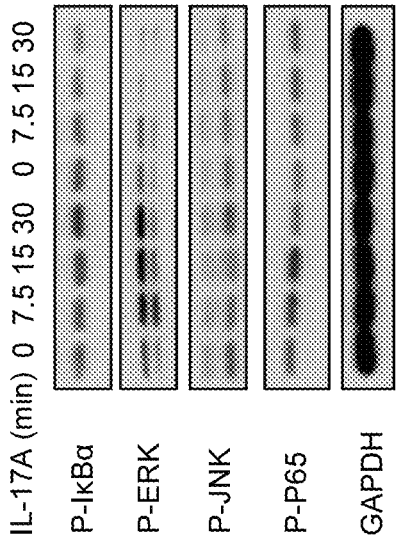
Figure 11D:
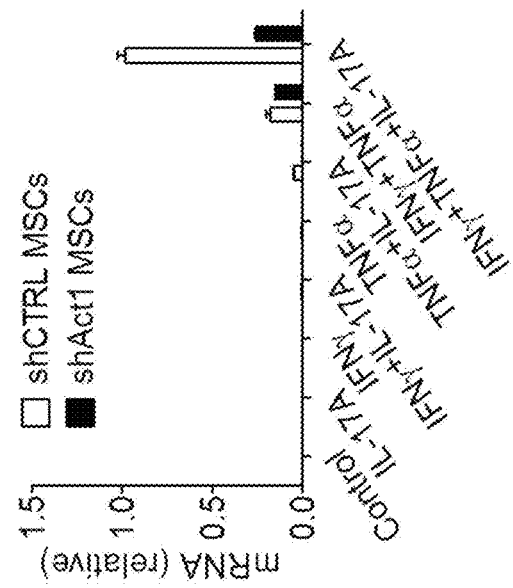

The recruitment of the adaptor protein Act1 to IL-17RA is linked to IL-17A dependent signaling. Since the phosphorylation of IκBα, ERK, p65, JNK were impaired in these Act1 knockdown MSCs (FIG. 11A), IL-17A could not upregulate IFNγ+TNFα induced iNOS expression in Act1 knockdown MSCs (FIG. 11B, 11C). Meanwhile, the enhancement of immunosuppression by IL-17A in MSCs was also not seen in absence of Act1 (FIG. 11D). Thus, the effects on gene expression were due to IL-17A. Together, these data indicated that IL-17A can synergize with IFNγ and TNFα to induce the expression of genes that contribute to the immunosuppressive function of MSCs.

IL-17A Reverses the Suppression of Gene Expression Imposed by RNA-Binding Protein AUF1

Messenger RNAs encoding iNOS and many cytokines/chemokines are rapidly degraded, which limits the abundance of both the mRNAs and proteins. Activation of signaling pathways, particularly during immune responses, stabilizes many of these mRNAs to increase their expression. Indeed, a major mechanism by which IL-17A induces expression of many inflammatory mediator genes is by stabilizing their mRNAs. Numerous proteins bind to specific RNA sequences, usually in the 3'-UTR, and target the mRNAs for rapid degradation. AU-rich elements (AREs) comprise one such family of mRNA degradation sequences. There are numerous proteins that bind AREs to elicit controlled expression of the mRNAs harboring them. These proteins include AUF1, HuR, KSRP, TIA-1/TIAR, and TTP. Some of the targets of these proteins include the ARE-mRNAs encoding iNOS, IL-6, and CXCL1. The ARE-binding protein AUF1 consists of four isoforms—p37, p40, p42, and p45—which bind and regulate degradation of iNOS and IL-6 mRNAs. It was thus hypothesized that AUF1 may act to limit the expression of iNOS and cytokine/chemokine mRNAs and that IL-17A may block this activity of AUF1 thereby increasing gene expression.

Figure 12A:
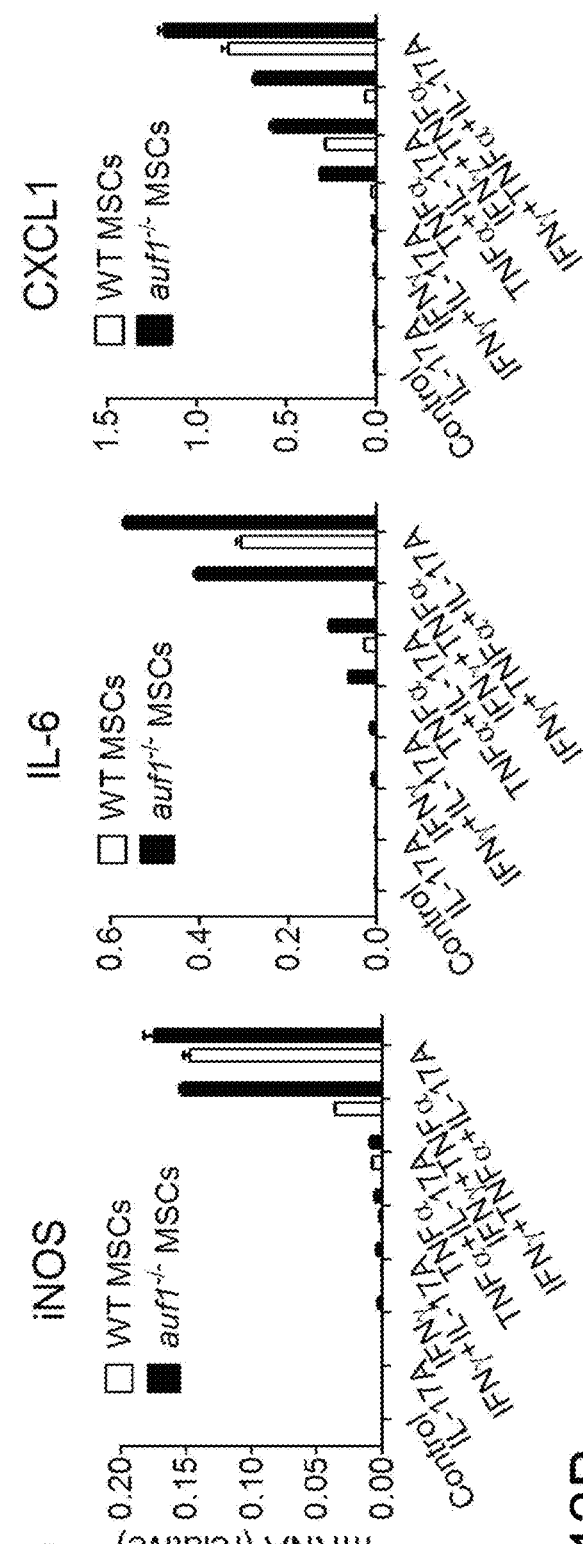
FIGS. 12A and 12B.
Figure 12B:
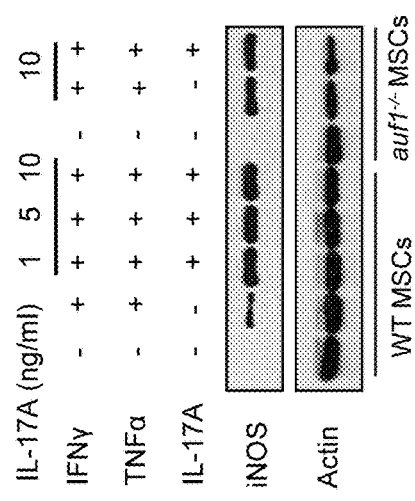

As such, cytokine-induced gene expression was compared between MSCs derive from bone marrow of auf1$^{-/-}$ mice and wild-type mice. Cells were cultured as before with combinations of cytokines, with or without IL-17A. While levels of iNOS, IL-6, and CXCL1 mRNAs were normally very low in wild-type MSCs, addition of IL-17A (together with IFNγ and TNFα) induced significant increases in these mRNAs (FIG. 12A; p<0.001). By contrast, levels of these three mRNAs were much higher in auf1$^{-/-}$ MSCs cultured with IFNγ+TNFα, and addition of IL-17A had little effect on mRNA levels (i.e., IL-17A increased their abundance less than twofold). Likewise, IFNγ and TNFα were sufficient to maximally induce iNOS protein in auf1$^{-/-}$ MSCs without the need for IL-17A, in contrast to wild-type MSCs (FIG. 12B, compare lanes 7 and 8 with lane 5).

Given the effects of AUF1 and IL-17A on gene expression, it was possible that knockout of AUF1 alone would be sufficient to provide the degree of mRNA stabilization, and increased gene expression, that would normally require IL-17A. Wild-type and auf1$^{-/-}$ MSCs were cultured with IFNγ+TNFα, with or without IL-17A. After 6 hr, Act.D was added to stop transcription.

At various time points, RNA was isolated from cells and levels of individual mRNAs were determined to assess mRNA decay kinetics. In wild-type MSCs, iNOS, IL-6, and CXCL1 mRNAs were relatively unstable with half lives of 4.3±1.4 hr, 0.7±0.1 hr, and 0.59±0.08 hr, respectively; IL-17A led to a twofold stabilization of all three mRNAs (FIG. 13A; p<0.05 for each). The CCL2 and CXCL10 mRNAs, which did not respond to IL-17A (see FIG. 13C), were not stabilized by IL-17A, as would be expected (FIG. 13A; t1/2=~ 2 hr for both mRNAs, with or without IL-17A).

In contrast to wild-type MSCs, knockout of AUF1 strongly stabilized iNOS, IL-6, and CXCL1 mRNAs (FIG. 13B; t1/2>10 hr for iNOS and IL-6; t1/2=4.3±0.6 hr for CXCL1). IL-17A had no effect on the half-lives of iNOS and IL-6 mRNAs (FIG. 13B), while it stabilized CXCL1 mRNA at least twofold (FIG. 13B; t1/2>10 hr versus 4.3±0.6 hr without IL-17A; see Discussion). These mRNA decay data indicated that, (i) AUF1 normally promotes degradation of iNOS, IL-6, and CXCL1 mRNAs in MSCs and IL-17A causes their stabilization; (ii) stabilization of these mRNAs by knockout of AUF1 is comparable in magnitude to the stabilizing effects of IL-17A on mRNAs in wild-type MSCs; and (iii) AUF1 knockout appears to obviate a requirement for IL-17A to induce iNOS/chemokine gene expression. Thus, AUF1 may serve as a control point through which IL-17A must act to elicit its effects on MSC gene expression, and possibly the ultimate immunosuppression, which is examined next.

Effects of AUF1 on Immunosuppression by MSCs In Vitro

Given that AUF1 knockout induced chemokine gene expression without the need for IL-17A (see FIG. 12 and FIG. 13), it was hypothesized that culturing auf1$^{-/-}$ MSCs with IFNγ+TNFα alone would be sufficient to phenocopy the immunosuppressive activity of wild-type MSCs cultured with all three cytokines. To address this hypothesis, wild-type and auf1$^{-/-}$ MSCs were cultured with IFNγ+TNFα, with or without IL-17A, and then co-cultured with the A1.1 T cell hybridoma for assays of T cell proliferation. IL-17A increased the immunosuppressive activity of wild-type MSCs compared with cells cultured without it; however, IFNγ+TNFα was sufficient to induce maximal immunosuppressive activity of auf1$^{-/-}$ MSCs and IL-17A did not further enhance the immunosuppressive effect (FIGS. 14A, 14B). These results, considered together, are consistent with observations that AUF1 limits iNOS and cytokine/chemokine gene expression; IL-17A reverses this effect to enhance immunosuppression by MSCs.

Figures 15A, 15B:
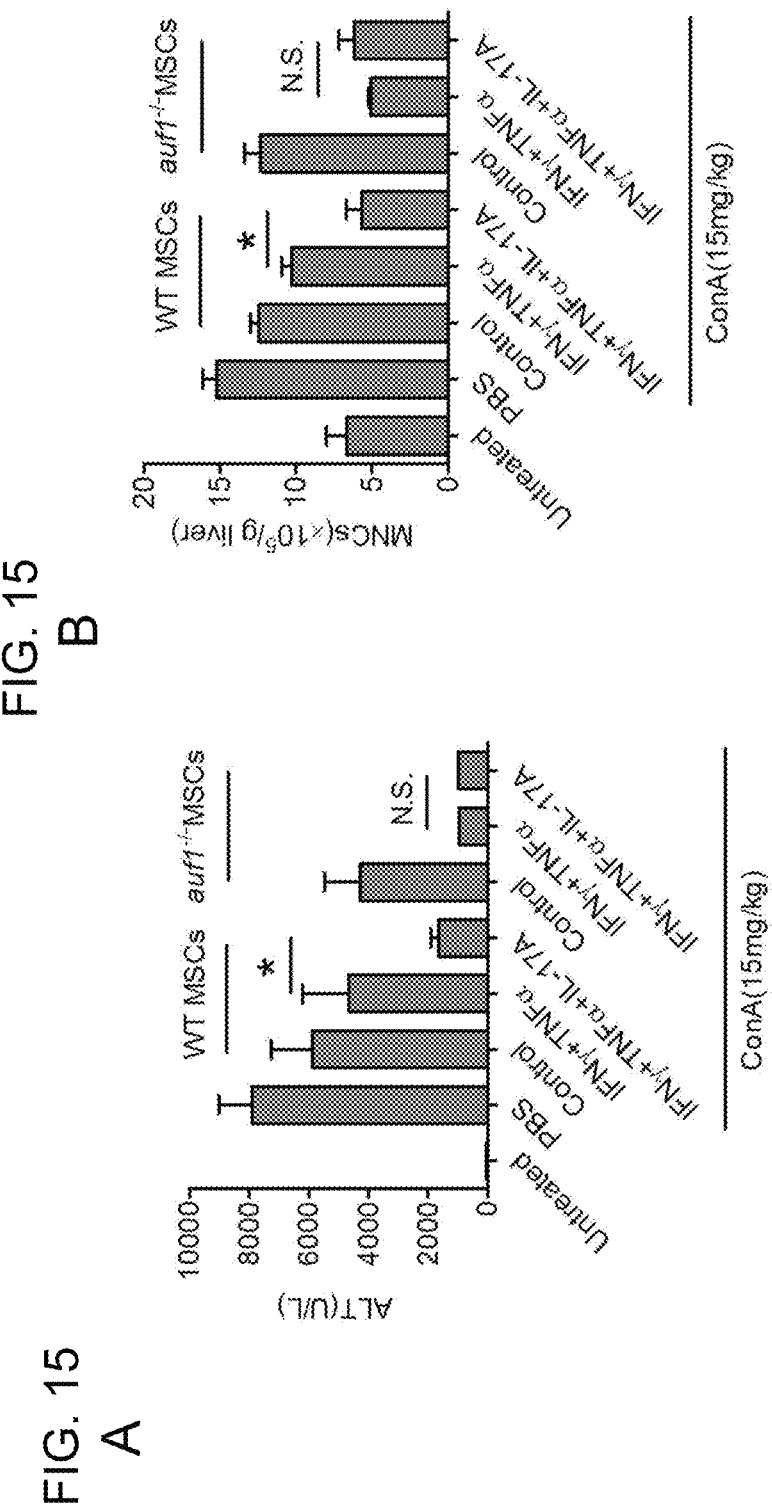
FIGS. 15A, 15B, 15C and 15D.
Figure 15:
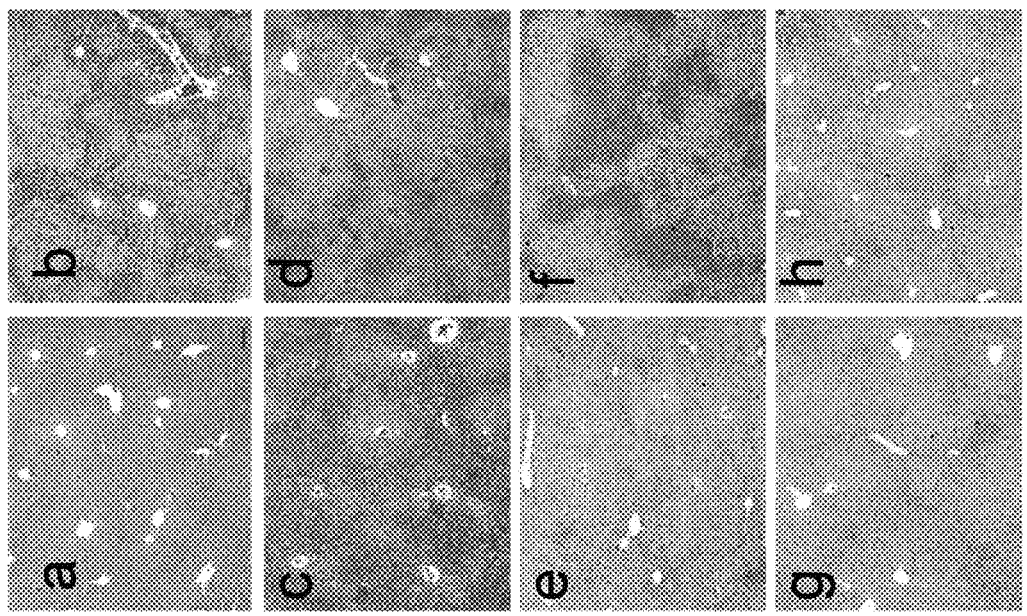
Figure 15:
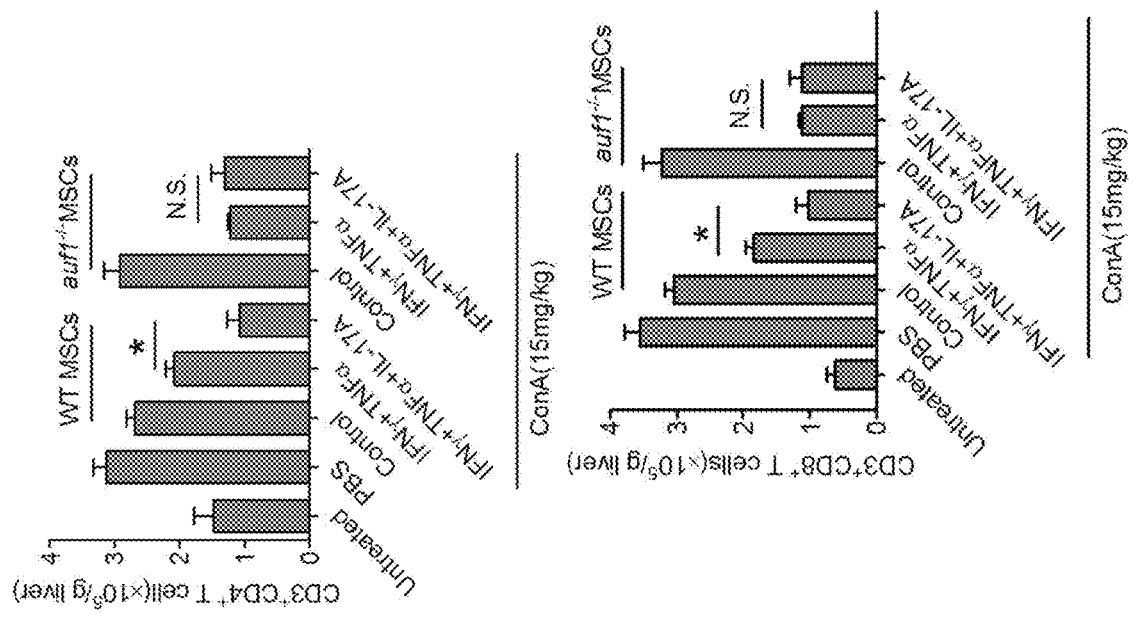

IL-17A Enhances the Therapeutic Effect of MSCs in Mice Suffering from ConA-Induced Liver Injury in an AUF1 Dependent Manner The inventors next examined the effects of IL-17A on immunosuppression in vivo by wild-type and auf1$^{-/-}$ MSCs. ConA-induced live injury in mice is a well-described in vivo model of autoimmune hepatitis mainly mediated by T cells. Since prior results showed that IL-17A can dramatically enhance the immunosuppressive effect of MSCs in an in vitro systems, it was expected that IL-17A could enable MSCs a better therapeutic effect in treating ConA-induced liver injury in mice. Accordingly, wild-type and auf1−/− MSCs with and without IFNγ+TNFα, in the presence or absence of IL-17A, for 12 hr were first treated and then intravenously injected into mice received ConA injection 30 min earlier. Compared with untreated or IFNγ+TNFα pre-treated wild-type MSCs, IFNγ+TNFα and IL-17A pretreated wild-type MSCs could substantially ameliorate liver damage with sharply reduced serum ALT activity and liver necrosis and inflammation (FIG. 15A, 15D). However, as for auf1$^{-/-}$ MSCs, only IFNγ+TNFα pretreatment will elicit maximal therapeutic effect in ConA induced liver injury, without the need for IL-17A (FIG. 15A, 15D). Consistent with the pattern of serum ALT activity, mononuclear cells as well as CD3+CD4+ and CD3$^+$CD8$^+$ T cells infiltration in liver were also dramatically decreased in mice administered by wild-type MSCs pretreated by IFNγ+TNFα with IL-17A, or auf1−/−MSCs pretreated by IFNγ+TNFα with or without IL-17A (FIG. 15B, 15C). Therefore, one of ordinary skill in the art can appreciate a new and novel therapy in treating ConA-induced liver damage, by utilizing MSCs pretreated by IFNγ+TNFα, together with IL-17A, and the effect of IL-17A was exerted in an AUF1 dependent manner.

Example 13

IL-17A Promoted the iNOS Expression Through Enhancing the mRNA Stability

To investigate the mechanism of how IL-17A enhances iNOS expression and immunosuppression by MSCs, the RNA stability of iNOS under cytokine induction was studied. As shown in FIG. 16A, iNOS mRNA half decay time is about 2.5 hours in the IFNγ+TNFα treatment group. Intriguingly, supplement with IL-17A completely protected iNOS mRNA within the time points tested.

In mammals, many mRNAs encoding inflammatory proteins could be destabilized by AU-rich elements (AREs) present in their 3'-untranslated regions. Rapid mRNA degradation occurs with the association of, ARE-binding proteins (AUBPs) with these mRNAs. AUFI, the ARE/poly(U)-binding/degradation factor 1, is one of the best-characterized AUBPs, which binds to many ARE-mRNAs to mediate degradation. It was suspected that AUFI is critical for the observations noted in IL-17A-mediated iNOS overexpression in MSCs.

To test this, AUF1 was knocked down with siRNA in MSCs and treated with IFNγ+TNFα with and without IL-17A. In wild type MSCs IL-17A strikingly induced the iNOS expression, whereas the absence of AUF1 largely abrogated this effect, indicating the importance of AUF1 in IL-17A-mediated iNOS expression in MSCs. Thus, IL-17A is capable of stabilizing iNOS mRNA in MSCs, which provide a novel method to effectively enhance the MSC-mediated therapy in clinical settings.

Type I Interferons and Fibroblast Growth Factor (FGF-2) Serve as Negative Regulators on MSC-Mediated Immunosuppression Through Down-Regulation of iNOS Expression.

As described above, IL-17A could be a potential factor to enhance MSC-mediated immunosuppression. However, in many cases, such immunosuppressive effect in vitro and invivo, either positively or negatively needs to be controlled. The available growth factors and cytokines were screened, and two factors were found strikingly down-regulating MSC-mediated immunosuppression: type I interferons and fibroblast growth factor (FGF-2).

These two factors could potentially inhibit the immunosuppressive effect of MSCs towards T-cell proliferation (FIGS. 16A, 16B). Further analysis revealed that, supplement of either of these cytokines was able to strikingly reduce the expression of iNOS protein and NO production (FIGS. 17A-D).

These findings substantiate methods to negatively control MSC-mediated immunosuppression. Accordingly, antibodies against type I interferons and FGF can be used to boost the immunosuppressive effect of MSCs.

Construction of Human IDO-Expressing Mouse iNOS-/- Cells (Humanized-IDO MSCs).

There is a species variation for MSC-mediated immunosuppression: NO is the effector molecule for mouse MSCs, whereas human and primate MSCs utilize indoleamine 2,3-dioxygenase (IDO) as the suppressive effector molecule.

Since mouse MSCs do not express indoleamine 2,3-dioxygenase (IDO) after inflammatory cytokine stimulation, it is hard to study the biological role of IDO in the mouse system. To circumvent this problem, mouse iNOS-/-MSCs were transfected with human IDO gene under the control of mouse iNOS promoter. This allowed the expression of IDO in mouse MSCs upon inflammatory cytokine stimulation. Stable human IDO expressing mouse iNOS-/-MSCs have been successfully generated, with the verification of the high IDO expression under the stimulation by mouse inflammatory cytokines. With these humanized-IDO MSCs, IDO is shown to be immunosuppressive in mouse MSCs in vitro and in vivo. Humanized-IDO mice were generated from iNOS-/-mice.

Human IDO gene is also being used to replace the mouse iNOS gene in normal mice in such the expressing of IDO is controlled by the mouse iNOS gene regulatory machineries, while the iNOS gene is silenced for further studying the pharmacology, cancer therapy, and assessing immune response and immune related pathogenesis.

Example 14

Transducing a Population of MSCs to Release Functional IFN α

In this example, inventors transduced MSCs with lentivirus encoding GFP (MSC-GFP) or GFP together with mouse IFNα (MSC-IFNα.). Over 90% cells were successfully transduced, as shown by GFP expression on flow cytometry (FIG. 18A). No apparent changes in morphology and proliferation rate between MSC-GFP and MSC-IFN α were observed. To examine the IFN production level of MSC-IFNα, levels of IFNα was quantified in the supernatant of MSCs cultured at $5 \times 10^5$ cells per ml for 48 h (FIG. 18 B).

ELISA analysis showed that there was 19 ng/ml of IFNα in the supernatant of MSC-IFNα while no IFN α was detected in the supernatant of MSC-GFP cultured under the same condition. To test whether IFN α released by MSC-IFNα possesses biological function, the expression of MHC I molecule H-2Kb on MSC surface was assessed by flow cytometry. IFN α increases the expression level of H-2Kb.

Figure 18B:
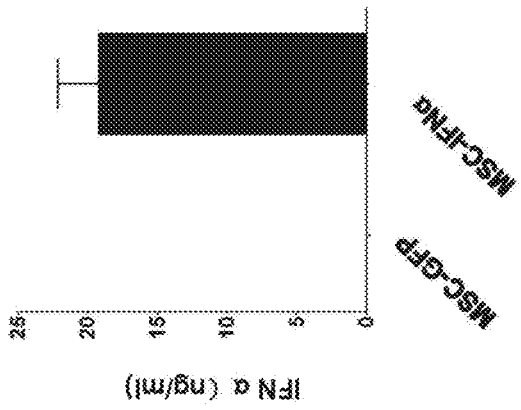
FIGS. 18A, 18B and 18C.
Figure 18A:
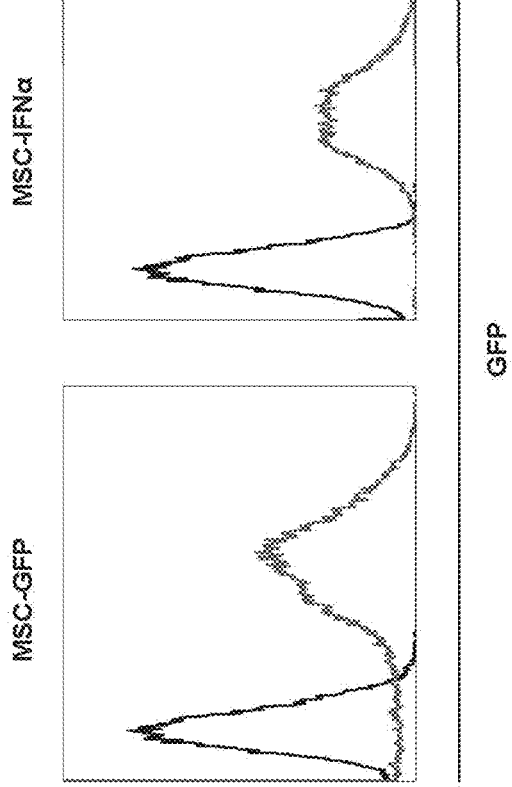
Figure 18C:
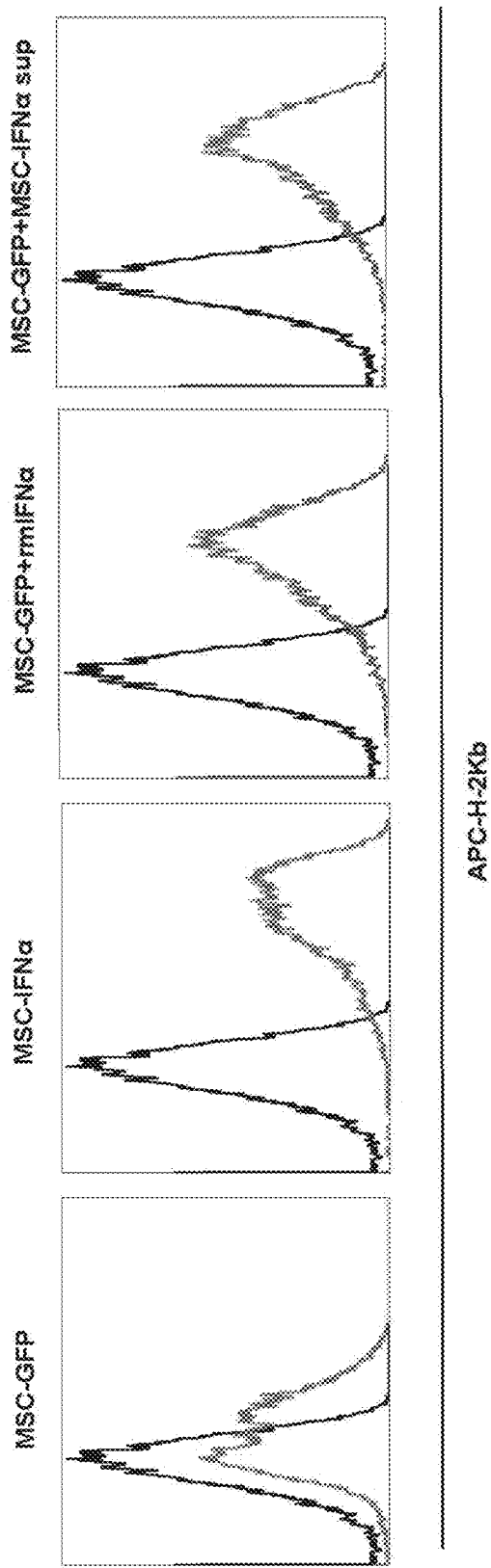

FIG. 18 C elaborates that the expression of H-2Kb was low in MSC-GFP, an intrinsic property of MSCs. However, surprisingly after treatment with recombinant IFN α, the expression of H-2Kb was dramatically increased in MSC-GFP. Similar increased expression of H-2b was also observed on cells treated with the supernatant of MSC-IFNα. Correspondingly, H-2Kb surface expression on MSC-IFNα was also increased to similar level as that of MSC-GFP treated with IFNα. These data demonstrated that MSC-IFN α produced biologically functional IFNα.

MSC-IFNα Exerted Potent Anti-Tumor Effect In Vivo.

To investigate the effect of MSC-IFN-α on tumor growth in vivo, mouse B16 melanoma model was employed. In this system, all cells and mice are in the C57BL/6 background. $1 \times 10^6$ B16 melanoma cells were inoculated alone, or with either $1 \times 106$ MSC-GFP or MSC-IFN-α intramuscularly, and tumors were removed and weighed twelve days later. It was unexpectedly observed that MSC-IFN α completely halted tumor growth, while MSC-GFP slightly enhanced umor growth (FIG. 19A). To examine the potency of the MSC-IFNα, $1 \times 10^6$ B16 melanoma cells with different numbers of MSC-IFNα were injected to the animals. Surprisingly, even $1 \times 10^4$ MSC-IFN α (at the ratio of MSC-IFNα: B16=1:100) could still potently prevent tumor growth in vivo (FIG. 19B). Moreover, all mice inoculated with tumor cells alone died within thirty days, while nearly half of mice received tumor cells together with MSC-IFNI survived for more than 100 days (FIG. 19C).

When MSC-IFNα cells were injected three or four days after B16 melanoma cell inoculation, tumor growth was also effectively inhibited (FIGS. 19D and 19E). To compare the anti-tumor capacity of MSC-IFNα with recombinant IFNα, mice with 5 µg recombinant IFNα (50,000 U) or $1 \times 10^6$ MSC-IFNα three days after B16 cell inoculation. Based on our in vitro assay, we roughly estimate that the $1 \times 10^6$ injected MSC-IFNα cells only produce around 19 ng of IFNα daily. This is far below the 5 µg recombinant IFNα injected. This observation is significant, as inventors observed that even with this low amount of IFN α produced (250 folds lower than the amount of recombinant IFNα injected), MSC-IFNα had much more potent anti-tumor effect than recombinant IFNα (FIG. 19F). Repeated IFN α administration further exerted potent anti-tumor affect in vivo (Supplemental FIG. 18). These data clearly demonstrated that IFNα-secreting MSCs possess highly potent anti-tumor activity in vivo.

MSCs Persisted in the Tumor, Decreased Tumor Cell Proliferation and Induced Tumor Cell Apoptosis.

To further investigate the mechanisms of the potent anti-tumor effect of MSC-IFN.α, the fate of the administered MSC-IFN α in vivo was tracked. Accordingly, MSC-IFN α was labeled with luciferase, whose activity was monitored in vivo with live imaging technology sing Berthod NC100 imaging system.

Figure 20B:
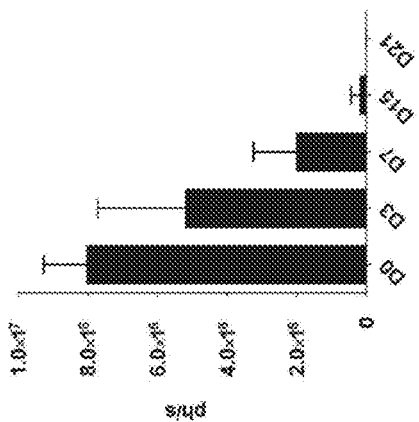
FIGS. 20A, 20B and 20C.
Figure 20A:
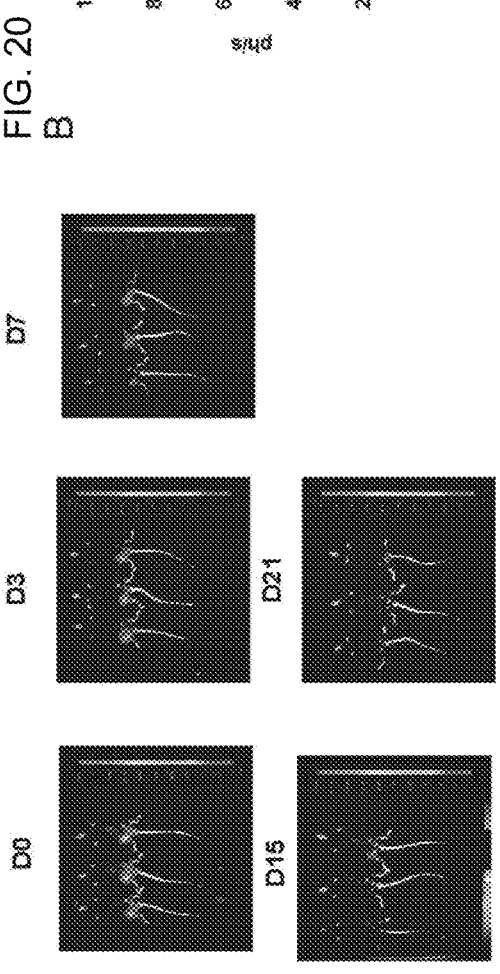

When co-injected with B16 cells, MSC-IFN α persisted only in tumors for over two weeks with gradual decrease (FIGS. 20A and 20B). Considering the potent anti-tumor effect of MSC-IFN α (still effective at the ratio of MSC-IFN α:B16=1:100), it is believed that SC-IFNα stay inside tumors and consecutively secret low but effective concentration of IFNα locally in the tumor for at least two weeks.

Those of ordinary skill in the art can appreciate the superiority of this affect to the short half-life and high dose requirement for administration of recombinant IFNα in vivo. When tumors were examined histologically, massive lymphocyte infiltration was found in the B16 plus MSC-IFNα Group.

Figure 20C:
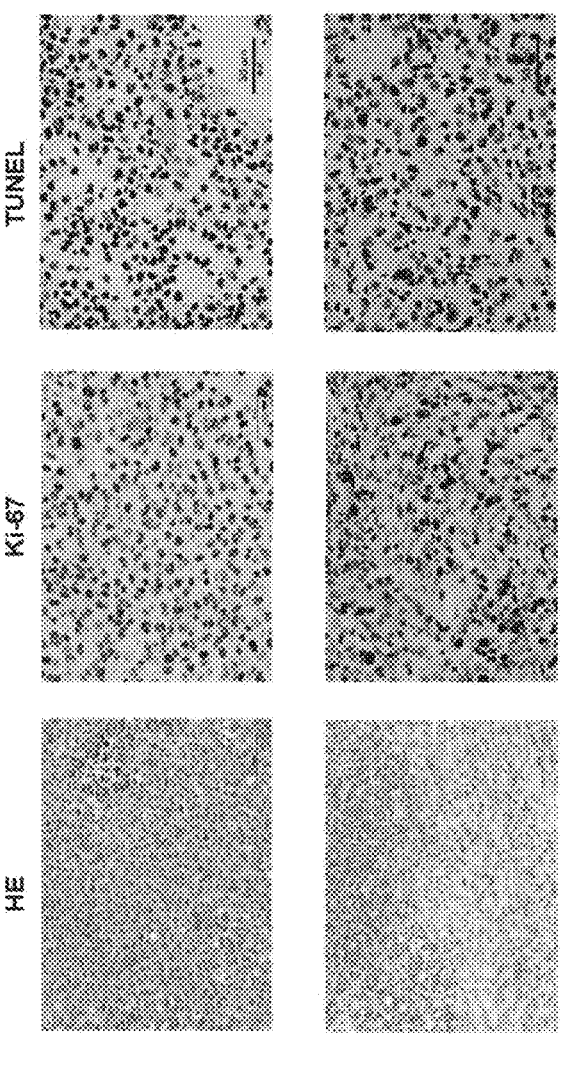

MSC-IFNα inhibited tumor cell proliferation as shown by the decreased ratio of Ki-67-positive cells and increased tumor cell apoptosis, as shown by TUNEL assay (FIG. 20C). The Anti-Tumor Activity of MSC-IFNα was Largely Immuno-Dependent.

Figures 21A, 21B, 21C, 21D, 21E, 21F, 21G:
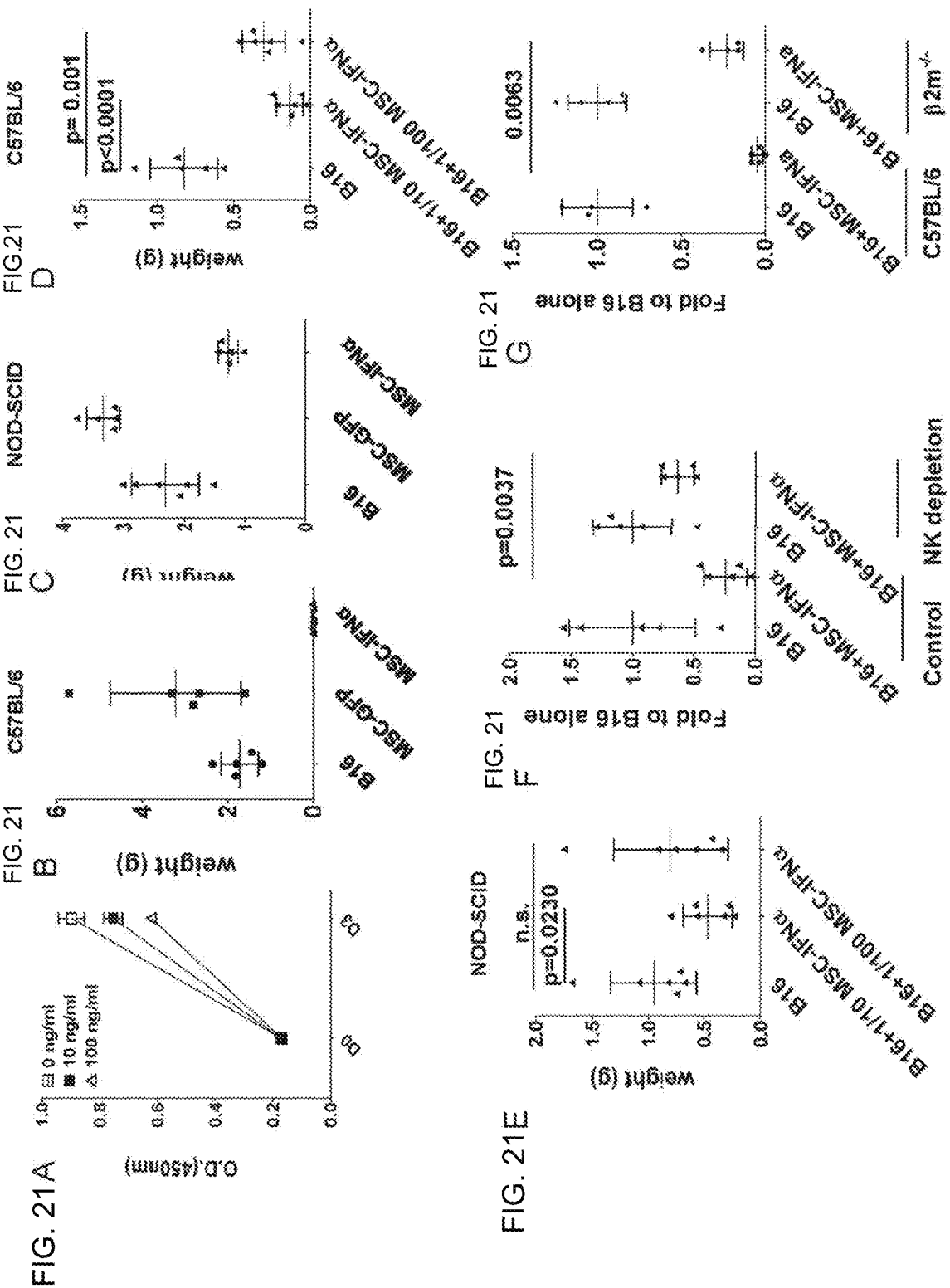
FIGS. 21A, 21B, 21C, 21D, 21E, 21F and 21G.

The direct effect of recombinant IFN α on tumor growth in vitro was studied. It is found that recombinant IFNα only inhibited B16 melanoma cells marginally even at high concentrations (up to 100 ng/ml, compared to 19 ng/ml produced by MSC-IFNα) (FIG. 21A). Therefore, considering the complete tumor growth inhibition observed in vivo by MSC-IFNα, inventors reasoned that there should be other mechanisms involved in addition to the direct inhibition of tumor growth.

To test whether the immune system played any roles in the anti-tumor effect of MSC-IFNα, B16 melanoma cells were inoculated alone, or with either MSC-GFP or MSC-IFNα into wild-type and immunodeficient NOD-SCID mice in parallel, and compared tumor growth in these mice. In wild-type mice, MSC-IFNα completely inhibited tumor growth (FIG. 21B), while in immunodeficient mice the tumor inhibition effect of MSC-IFNα was greatly abolished (FIG. 21C). To more clearly analyze the role of the immune system in the anti-tumor effect of MSC-IFN α, we injected less MSC-IFNα together with B16 tumor cells so as to minimize the contribution of direct tumor inhibition. When low numbers of MSC-IFN α (1/100 of tumor cells) were used, tumor growth was still effectively inhibited in wild type mice (FIG. 21D); however this effect completely disappeared in immunodeficient mice (FIG. 21E).

The inventors then tested whether NK cells were involved in the anti-tumor effect of MSC-IFNα by depleting NK cells with anti-asialo GM1 antibody. Surprisingly, tumor growth was effectively inhibited in control mice; however, this inhibition was greatly reversed in mice treated with NK cells depletion antibody (FIG. 21F). CD8+ T cells also contributed to the anti-tumor effect of MSC-IFNα, as shown by the diminished inhibition of tumor growth by MSC-IFNα in CD8+ T cells deficient mice, β2m knockout mice (FIG. 21G). These data clearly showed the immune system is critical in the anti-tumor effect of MSC-IFNα, in addition to its direct effect on tumor cells.

In this study, IFNα was delivered into tumor via MSCs in normal mice. In such immune competent mice, IFNα was found to exert its effect through promoting anti-tumor immunity. Even low number of IFNα-secreting MSCs had the ability to inhibit one-hundred folds more tumor cell growth in normal mice, but not in immunodeficient mice. Furthermore, both NK cells and CD8+ T cells were shown to play an important role in the anti-tumor effect of IFNα-secreting MSCs in vivo.

IFNα could overcome the immunosuppression of MSCs. Accordingly, it is contemplated that IFNα effectively reverses on the immunosuppressive property of MSCs induced by IFNγ and TNFα. The long-term existence of MSCs-IFNα in tumor avoided frequent injection as seen with IFNα. The low but effective level of IFNα released by MSCs-IFNα is unlikely to cause any side effects. Those of ordinary skill in the art can appreciate that MSCs engineered to express immune stimulating factors hold great promise for tumor therapy in the future.

While the invention has been described with references to specific embodiments, modifications and variations of the invention may be construed without departing from the scope of the invention, which is defined in the following claims.

---

What is claimed is:

1. A method for enhancing immunosuppression of an immune response mediated by activated T cells in a patient in need thereof comprising administering to said patient an effective amount of:
   (a) a population of isolated mesenchymal stem cells activated by culturing in a medium comprising interferon gamma (IFNγ), interleukin 17A (IL-17A), and tumor necrosis factor alpha (TNF α);
   (b) isolated IFNγ;
   (c) TNF α; and
   (d) IL-17A.

2. The method of claim 1, wherein said patient in need suffers from any one of the conditions selected from the group consisting of an autoimmune disorder, allergy, sepsis, cirrhosis, cancer, viral infections and organ transplant.

3. The method of claim 1, further comprising inducing the expression of indoleamine 2,3-dioxygenase (IDO) in at least a subset of said mesenchymal stem cells.

4. The method of claim 1, further comprising administering to said patient an effective amount of one or both of interleukin-1 alpha (IL-1 α) and interleukin-1 beta (IL-1 β).

5. A method of suppressing an immune response mediated by activated T cells comprising administering to a subject in need thereof an effective amount of a population of isolated mesenchymal stem cells prepared by a process comprising the steps of:
   (i) obtaining multipotent progenitor cells;
   (ii) culturing said multipotent progenitor cells in a medium;
   (iii) separating mesenchymal stem cells from differentiated cells in said medium; and
   (iv) activating at least a subset of said separated mesenchymal stem cells by culturing the cells in a medium comprising isolated interferon gamma (IFNγ), interleukin 17A (IL-17A), and tumor necrosis factor alpha (TNF α), for a sufficient period of time such that the activated mesenchymal stem cells are immunosuppressive.

6. The method of claim 5, wherein step (iv) further comprises exposing the at least a subset of said mesenchymal stem cells to one or both of IL-1 α and IL-1 β.

7. A method for suppressing an immune response mediated by activated T cells in a patient in need thereof comprising administering to said patient a composition comprising an effective amount of a population of isolated mesenchymal stem cells activated by culturing in a medium comprising interferon gamma (IFNγ), interleukin 17A (IL-17A), and tumor necrosis factor alpha (TNF α) for a sufficient amount of time.

8. The method of claim 7, wherein the population of isolated trained mesenchymal stem cells are activated by culturing in a medium comprising IFNγ, IL-17A, TNF α, and one or both of IL-1 α and IL-1 β for a sufficient amount of time.

* * * * *

SEQUENCE LISTING

```
<160> NUMBER OF SEQ ID NOS: 16

<210> SEQ ID NO 1
<211> LENGTH: 21
<212> TYPE: DNA
<213> ORGANISM: artificial
<220> FEATURE:
<223> OTHER INFORMATION: synthetic primer

<400> SEQUENCE: 1
cagctgggct gtacaaacct t                                              21

<210> SEQ ID NO 2
<211> LENGTH: 21
<212> TYPE: DNA
<213> ORGANISM: artificial
<220> FEATURE:
<223> OTHER INFORMATION: synthetic primer

<400> SEQUENCE: 2
cattggaagt gaagcgtttc g                                              21

<210> SEQ ID NO 3
<211> LENGTH: 18
<212> TYPE: DNA
<213> ORGANISM: artificial
```

```
<220> FEATURE:
<223> OTHER INFORMATION: synthetic beta-actin primer

<400> SEQUENCE: 3
ccacgagcgg ttccgatg                                                 18

<210> SEQ ID NO 4
<211> LENGTH: 20
<212> TYPE: DNA
<213> ORGANISM: artificial
<220> FEATURE:
<223> OTHER INFORMATION: synthetic beta-actin primer

<400> SEQUENCE: 4
gccacaggat tccataccca                                               20

<210> SEQ ID NO 5
<211> LENGTH: 23
<212> TYPE: DNA
<213> ORGANISM: artificial
<220> FEATURE:
<223> OTHER INFORMATION: synthetic il-6 primer

<400> SEQUENCE: 5
gaggatacca ctcccaacag acc                                           23

<210> SEQ ID NO 6
<211> LENGTH: 24
<212> TYPE: DNA
<213> ORGANISM: artificial
<220> FEATURE:
<223> OTHER INFORMATION: synthetic il-6 primer

<400> SEQUENCE: 6
aagtgcatca tcgttgttca taca                                          24

<210> SEQ ID NO 7
<211> LENGTH: 19
<212> TYPE: DNA
<213> ORGANISM: artificial
<220> FEATURE:
<223> OTHER INFORMATION: synthetic CXCL1 primer

<400> SEQUENCE: 7
ctgcacccaa accgaagtc                                                19

<210> SEQ ID NO 8
<211> LENGTH: 20
<212> TYPE: DNA
<213> ORGANISM: artificial
<220> FEATURE:
<223> OTHER INFORMATION: synthetic CXCL1 primer

<400> SEQUENCE: 8
agcttcaggg tcaaggcaag                                               20

<210> SEQ ID NO 9
<211> LENGTH: 22
<212> TYPE: DNA
<213> ORGANISM: artificial
<220> FEATURE:
<223> OTHER INFORMATION: synthetic CCL2 primer

<400> SEQUENCE: 9
tctctcttcc tccaccacca tg                                            22
```

<210> SEQ ID NO 10
<211> LENGTH: 21
<212> TYPE: DNA
<213> ORGANISM: artificial
<220> FEATURE:
<223> OTHER INFORMATION: synthetic CCL2 primer

<400> SEQUENCE: 10
gcgttaactg catctggctg a                                      21

<210> SEQ ID NO 11
<211> LENGTH: 22
<212> TYPE: DNA
<213> ORGANISM: artificial
<220> FEATURE:
<223> OTHER INFORMATION: synthetic CCL5 primer

<400> SEQUENCE: 11
tttctacacc agcagcaagt gc                                     22

<210> SEQ ID NO 12
<211> LENGTH: 21
<212> TYPE: DNA
<213> ORGANISM: artificial
<220> FEATURE:
<223> OTHER INFORMATION: synthetic CCL5 primer

<400> SEQUENCE: 12
ccttcgtgtg acaaacacga c                                      21

<210> SEQ ID NO 13
<211> LENGTH: 22
<212> TYPE: DNA
<213> ORGANISM: artificial
<220> FEATURE:
<223> OTHER INFORMATION: synthetic CXCL9 primer

<400> SEQUENCE: 13
agtgtggagt tcgaggaacc ct                                     22

<210> SEQ ID NO 14
<211> LENGTH: 19
<212> TYPE: DNA
<213> ORGANISM: artificial
<220> FEATURE:
<223> OTHER INFORMATION: synthetic CXCL9 primer

<400> SEQUENCE: 14
tgcaggagca tcgtgcatt                                         19

<210> SEQ ID NO 15
<211> LENGTH: 21
<212> TYPE: DNA
<213> ORGANISM: artificial
<220> FEATURE:
<223> OTHER INFORMATION: synthetic CXCL10 primer

<400> SEQUENCE: 15
tagctcaggc tcgtcagttc t                                      21

<210> SEQ ID NO 16
<211> LENGTH: 21
<212> TYPE: DNA
<213> ORGANISM: artificial
<220> FEATURE:
<223> OTHER INFORMATION: synthetic CXCL10 primer

```
<400> SEQUENCE: 16
gatggtggtt aagttcgtgc t                                             21
```